United States Patent
Ghislieri et al.

(10) Patent No.: US 12,203,114 B2
(45) Date of Patent: Jan. 21, 2025

(54) METHOD FOR THE PRODUCTION OF ACRYLIC ACID OR SALTS THEREOF

(71) Applicant: BASF SE, Ludwigshafen am Rhein (DE)

(72) Inventors: Diego Ghislieri, Ludwigshafen (DE); Tobias Joachim Zimmermann, Ludwigshafen (DE); Stefan Seemayer, Ludwigshafen (DE); Michael Breuer, Ludwigshafen (DE); Doreen Schachtschabel, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 17/286,328

(22) PCT Filed: Oct. 9, 2019

(86) PCT No.: PCT/EP2019/077369
§ 371 (c)(1),
(2) Date: Apr. 16, 2021

(87) PCT Pub. No.: WO2020/078798
PCT Pub. Date: Apr. 23, 2020

(65) Prior Publication Data
US 2021/0340518 A1    Nov. 4, 2021

(30) Foreign Application Priority Data

Oct. 18, 2018 (EP) ..................................... 18201085
Mar. 21, 2019 (EP) ..................................... 19164303

(51) Int. Cl.
C12N 9/78       (2006.01)
C12P 7/40       (2006.01)
C12P 7/60       (2006.01)

(52) U.S. Cl.
CPC .................. *C12N 9/78* (2013.01); *C12P 7/40* (2013.01); *C12Y 305/05001* (2013.01)

(58) Field of Classification Search
CPC ..................................... C12N 9/78; C12P 7/40
See application file for complete search history.

(56) References Cited

U.S. PATENT DOCUMENTS

| | | | |
|---|---|---|---|
| 5,565,350 A | 10/1996 | Kmeic | |
| 6,162,624 A | 12/2000 | Symes et al. | |
| 6,670,158 B2 | 12/2003 | Dicosimo et al. | |
| 6,998,258 B1 | 2/2006 | Kesseler et al. | |
| 7,026,530 B2 | 4/2006 | Benfey et al. | |
| 7,592,164 B2 | 9/2009 | Hughes et al. | |
| 9,217,164 B2* | 12/2015 | Chaplin | C12P 13/005 |
| 2003/0124698 A1 | 7/2003 | Desantis et al. | |
| 2021/0348200 A1 | 11/2021 | Ghislieri et al. | |

FOREIGN PATENT DOCUMENTS

| | | |
|---|---|---|
| CN | 1207770 A | 2/1999 |
| CN | 1886501 A | 12/2006 |
| EP | 3312286 A2 | 4/2018 |
| JP | 200655004 A | 3/2006 |
| RU | 2304165 C1 | 8/2007 |
| WO | 9706248 A1 | 2/1997 |
| WO | 9721805 A1 | 6/1997 |
| WO | 9858072 A1 | 12/1998 |
| WO | 0015815 A1 | 3/2000 |
| WO | 0132890 A1 | 5/2001 |
| WO | 0148175 A1 | 7/2001 |
| WO | 2001075077 A2 | 10/2001 |
| WO | 03106415 A1 | 12/2003 |
| WO | 2004076655 A1 | 9/2004 |
| WO | 2009059104 A1 | 5/2009 |

OTHER PUBLICATIONS

Studer. Residue mutations and their impact on protein structure and function: detecting beneficial and pathogenic changes. Biochem. J. (2013) 449, 581-594.*
Fransceus. J Ind Microbiol Biotechnol. May 2017;44(4-5):687-695.*
Sanavia. Computational and Structural Biotechnology Journal, vol. 18, 2020, pp. 1968-1979.*
"Candidatus Dadabacteria bacterium CSP1-2", Database UniParc [Online], retrieved from Database accession No. UPI00072535E8, XP002796674, 2015, 1 page.
"Ensifer shofinae", Database UniParc [Online], retrieved from Database accession No. UPI000826D89D, XP002796651, 2016, 1 page.
"Pseudomonas sp. RIT357/Pseudomonas sp. 2995-1", Database UniParc [Online], retrieved from Database accession No. UPI0004450DC8, XP002796672, 2014, 1 page.
"Pseudomonas sp/Rhodococcus rhodochrous", Database UniParc [Online], retrieved from Database accession No. UPI000044325C, XP002796673, 2004, 1 page.
Bhalla, et al., "Enzymes of Aldoxime-Nitrile Pathway for Organic Synthesis", Reviews in Environmental Science and Bio/Technology, vol. 17, Issue 2, Apr. 16, 2018, pp. 229-239.
Bhalla, et al., "Nitrile Metabolizing Enzymes in Biocatalysis and Biotransformation", Applied Biochemistry and Biotechnology, vol. 185, Issue 4, Jan. 30, 2018, pp. 925-946.
International Search Report for PCT Patent Application No. PCT/EP2019/077369, Issued on Jan. 17, 2020, 5 pages.
J. Goa, "A Micro Biuret Method for Protein Determination Determination of Total Protein in Cerebrospinal Fluid", Scandinavian Journal of Clinical and Laboratory Investigation, vol. 5, Issue 3, 1953, pp. 218-222.
Lavrov, et al., "Optimization of the Expression of Nitrilase from Alcaligenes denitrificans in Rhodococcus hodochrous to Improve the Efficiency of Biocatalytic Synthesis of Ammonium Acrylate", Applied Biochemistry and Microbiology, vol. 55, Issue 9, Dec. 5, 2019, pp. 861-869.

(Continued)

Primary Examiner — Yong D Pak
(74) Attorney, Agent, or Firm — Armstrong Teasdale LLP

(57) ABSTRACT

Described herein are methods for the production of ammonium acrylate or salts thereof from acrylonitrile using nitrilase as a catalyst.

6 Claims, No Drawings

Specification includes a Sequence Listing.

(56) References Cited

OTHER PUBLICATIONS

Li, et al., "Enhanced Catalytic Efficiency of Nitrilase from Acidovorax Facilis 72W and Application in Bioconversion of 3-Cyanopyridine to Nicotinic Acid", Journal of Molecular Catalysis B: Enzymatic, vol. 133, Supplement 1, Nov. 2016, pp. S459-S467.

Lowry, et al., "Protein Measurement with the Folin Phenol Reagent", Journal of Biological Chemistry, vol. 193, Issue 1, Nov. 1, 1951, pp. 265-275.

Marion M. Bradford, "A rapid and sensitive method for the quantitation of microgram quantities of protein utilizing the principle of protein-dye binding", Analytical Biochemistry, vol. 72, Issue 1-2, May 7, 1976, pp. 248-254.

Meinkoth, et al., "Hybridization of nucleic acids immobilized on solid supports", Analytical Biochemistry, vol. 138, Issue 2, May 1, 1984, pp. 267-284.

Needleman, et al., "A general method applicable to the search for similarities in the amino acid sequence of two proteins", Journal of Molecular Biology, vol. 48, Issue 3, Mar. 28, 1970, pp. 443-453.

Stueckler, et al., "Nicotinamide-independent asymmetric bioreduction of Cdouble bondC-bonds via disproportionation of enones catalyzed by enoate reductases", Tetrahedron, vol. 66, Issue 3, Jan. 16, 2010, pp. 663-667.

Sun, et al., "Ammonium acrylate biomanufacturing by an engineered Rhodococcus ruber with nitrilase overexpression and double-knockout of nitrile hydratase and amidase", Journal of Industrial Microbiology & Biotechnology, vol. 43, Issue 12, Dec. 1, 2016, pp. 1631-1639.

"SubName: Full=Aliphatic nitrilase {ECO:0000313|EMBL:KIC94389. 1}, SEQ ID No. 1", Database UniProt [Online], retrieved from EBI Database accession No. A0A0C1IV51, retrieved on May 26, 2023, 1 page.

"SubName: Full=Carbon-nitrogen family hydrolase (ECO:0000313|EMBL:EZP62862.1}, SEQ ID No. 1", Database UniProt [Online], retrieved from EBI Database accession No. A0A031IPA2, retrieved on Jun. 1, 2023, 1 page.

"SubName: Full=Nitrilase {ECO:0000313|EMBL:KRT65552.1}, SEQ ID No. 1", Database UniProt [Online], retrieved from EBI Database accession No. A0A0T5ZRV8, retrieved on Jun. 1, 2023, 1 page.

\* cited by examiner

SEQUENCE LISTING

```
<160> NUMBER OF SEQ ID NOS: 75

<210> SEQ ID NO 1
<211> LENGTH: 1011
<212> TYPE: DNA
<213> ORGANISM: Unknown
<220> FEATURE:
<223> OTHER INFORMATION: Unknown prokaryotic organism

<400> SEQUENCE: 1
atgaaagaag cgattaaagt ggcgtgcgtg caggcggcgc cgatttatat ggatctggaa     60
gcgaccgtgg ataaaaccat tgaactgatg gaagaagcgg cgcgcaacaa cgcgcgcctg    120
attgcgtttc cggaaacctg gattccgggc tatccgtggt ttctgtggct ggatagcccg    180
gcgtgggcga tgcagtttgt gcgccagtat catgaaaaca gcctggaact ggatggcccg    240
caggcgaaac gcattagcga tgcggcgaaa cgcctgggca ttatggtgac cctgggcatg    300
agcgaacgcg tgggcggcac cctgtatatt agccagtggt ttattggcga taacggcgat    360
accattggcg cgcgccgcaa actgaaaccg acctttgtgg aacgcaccct gtttggcgaa    420
ggcgatggca gcagcctggc ggtgtttgaa accagcgtgg gccgcctggg cggcctgtgc    480
tgctgggaac atctgcagcc gctgaccaaa tatgcgctgt atgcgcagaa cgaagaaatt    540
cattgcgcgg cgtggccgag ctttagcctg tatccgaacg cggcgaaagc gctgggcccg    600
gatgtgaacg tggcggcgag ccgcatttat gcggtggaag ccagtgcttt tgtgctggcg    660
agctgcgcgc tggtgagcca gagcatgatt gatatgctgt gcaccgatga tgaaaaacat    720
gcgctgctgc tggcgggcgg cggccatagc cgcattattg gcccggatgg cggcgatctg    780
gtggcgccgc tggcggaaaa cgaagaaggc attctgtatg cgaacctgga tccgggcgtg    840
cgcattctgg cgaaaatggc ggcggatccg gcgggccatt atagccgccc ggatattacc    900
cgcctgctga ttgatcgcag cccgaaactg ccggtggtgg aaattgaagg cgatctgcgc    960
ccgtatgcgc tgggcaaagc gagcgaaacc ggcgcgcagc tggaagaaat t             1011

<210> SEQ ID NO 2
<211> LENGTH: 337
<212> TYPE: PRT
<213> ORGANISM: Unknown
<220> FEATURE:
<223> OTHER INFORMATION: Unknown prokaryotic organism

<400> SEQUENCE: 2

Met Lys Glu Ala Ile Lys Val Ala Cys Val Gln Ala Ala Pro Ile Tyr
1               5                   10                  15

Met Asp Leu Glu Ala Thr Val Asp Lys Thr Ile Glu Leu Met Glu Glu
            20                  25                  30

Ala Ala Arg Asn Asn Ala Arg Leu Ile Ala Phe Pro Glu Thr Trp Ile
        35                  40                  45

Pro Gly Tyr Pro Trp Phe Leu Trp Leu Asp Ser Pro Ala Trp Ala Met
    50                  55                  60

Gln Phe Val Arg Gln Tyr His Glu Asn Ser Leu Glu Leu Asp Gly Pro
65                  70                  75                  80

Gln Ala Lys Arg Ile Ser Asp Ala Ala Lys Arg Leu Gly Ile Met Val
                85                  90                  95
```

```
Thr Leu Gly Met Ser Glu Arg Val Gly Gly Thr Leu Tyr Ile Ser Gln
            100                 105                 110

Trp Phe Ile Gly Asp Asn Gly Asp Thr Ile Gly Ala Arg Arg Lys Leu
        115                 120                 125

Lys Pro Thr Phe Val Glu Arg Thr Leu Phe Gly Glu Gly Asp Gly Ser
    130                 135                 140

Ser Leu Ala Val Phe Glu Thr Ser Val Gly Arg Leu Gly Gly Leu Cys
145                 150                 155                 160

Cys Trp Glu His Leu Gln Pro Leu Thr Lys Tyr Ala Leu Tyr Ala Gln
                165                 170                 175

Asn Glu Glu Ile His Cys Ala Ala Trp Pro Ser Phe Ser Leu Tyr Pro
            180                 185                 190

Asn Ala Ala Lys Ala Leu Gly Pro Asp Val Asn Val Ala Ala Ser Arg
        195                 200                 205

Ile Tyr Ala Val Glu Gly Gln Cys Phe Val Leu Ala Ser Cys Ala Leu
    210                 215                 220

Val Ser Gln Ser Met Ile Asp Met Leu Cys Thr Asp Asp Glu Lys His
225                 230                 235                 240

Ala Leu Leu Leu Ala Gly Gly His Ser Arg Ile Ile Gly Pro Asp
                245                 250                 255

Gly Gly Asp Leu Val Ala Pro Leu Ala Glu Asn Glu Glu Gly Ile Leu
            260                 265                 270

Tyr Ala Asn Leu Asp Pro Gly Val Arg Ile Leu Ala Lys Met Ala Ala
        275                 280                 285

Asp Pro Ala Gly His Tyr Ser Arg Pro Asp Ile Thr Arg Leu Leu Ile
    290                 295                 300

Asp Arg Ser Pro Lys Leu Pro Val Val Glu Ile Glu Gly Asp Leu Arg
305                 310                 315                 320

Pro Tyr Ala Leu Gly Lys Ala Ser Glu Thr Gly Ala Gln Leu Glu Glu
                325                 330                 335

Ile
```

<210> SEQ ID NO 3
<211> LENGTH: 942
<212> TYPE: DNA
<213> ORGANISM: Unknown
<220> FEATURE:
<223> OTHER INFORMATION: Unknown prokaryotic organism

<400> SEQUENCE: 3

```
atgggtgaat cggtgaagt taccctgggt gttgctcagg ctgctccggt ttacttcgac      60
cgtgaagctt ctaccgaaaa agctcgtggt ctgatccgtg aagctggtga aaaaggtgtt    120
gacctgctgg cttttcggtga aacctggctg accggttacc gtactggaa agacgctccg    180
tggtctcgtg aatacaacga cctgcgtgct cgttacgttg ctaacggtgt tatgatcccg    240
ggtccggaaa ccgacgctct gtgccaggct gctgctgaag ctggtgttga cgttgctatc    300
ggtgttgttg aactggaacc gggttctctg tcttctgttt actgcaccct gctgttcatc    360
tctcgtgaag gtgaaatcct gggtcgtcac cgtaaactga accgaccga ctctgaacgt    420
cgttactggt ctgaaggtga cgctaccggt ctgcgtgttt acgaacgtcc gtacggtcgt    480
ctgtctggtc tgaactgctg gaacacctg atgatgctgc cgggttacgc tctggctgct    540
cagggtaccc agttccacgt tgctgcttgg ccgaacatgg cttcttctgc ttctgaactg    600
ctgtctcgtg cttacgctta ccaggctggt tgctacgttc tgtgcgctgg tggtctgggt    660
```

```
ccggctccgg gtgaactgcc ggacggtatc gctgctgaat ctctggacca cctgaccggt    720
gaatcttgca tcatcgaccc gtggggtaaa gttatcgctg gtccggtttc ttgcgaagaa    780
accctgatca ccgctcgtgt ttctaccgct tctatctacc gtcgtaaatc tctgaccgac    840
gttggtggtc actactctcg tccggacgtt ttccgtttcg aagttgaccg ttctgaacgt    900
ccgcgtgttg ttttccgtga cggtgacgtt gacgaccgtg gt                      942
```

<210> SEQ ID NO 4
<211> LENGTH: 314
<212> TYPE: PRT
<213> ORGANISM: Unknown
<220> FEATURE:
<223> OTHER INFORMATION: Unknown prokaryotic organism

<400> SEQUENCE: 4

```
Met Gly Glu Phe Gly Glu Val Thr Leu Gly Val Ala Gln Ala Ala Pro
1               5                   10                  15

Val Tyr Phe Asp Arg Glu Ala Ser Thr Glu Lys Ala Arg Gly Leu Ile
            20                  25                  30

Arg Glu Ala Gly Glu Lys Gly Val Asp Leu Leu Ala Phe Gly Glu Thr
        35                  40                  45

Trp Leu Thr Gly Tyr Pro Tyr Trp Lys Asp Ala Pro Trp Ser Arg Glu
    50                  55                  60

Tyr Asn Asp Leu Arg Ala Arg Tyr Val Ala Asn Gly Val Met Ile Pro
65                  70                  75                  80

Gly Pro Glu Thr Asp Ala Leu Cys Gln Ala Ala Glu Ala Gly Val
                85                  90                  95

Asp Val Ala Ile Gly Val Val Glu Leu Glu Pro Gly Ser Leu Ser Ser
            100                 105                 110

Val Tyr Cys Thr Leu Leu Phe Ile Ser Arg Glu Gly Glu Ile Leu Gly
            115                 120                 125

Arg His Arg Lys Leu Lys Pro Thr Asp Ser Glu Arg Arg Tyr Trp Ser
        130                 135                 140

Glu Gly Asp Ala Thr Gly Leu Arg Val Tyr Glu Arg Pro Tyr Gly Arg
145                 150                 155                 160

Leu Ser Gly Leu Asn Cys Trp Glu His Leu Met Met Leu Pro Gly Tyr
                165                 170                 175

Ala Leu Ala Ala Gln Gly Thr Gln Phe His Val Ala Ala Trp Pro Asn
            180                 185                 190

Met Ala Ser Ser Ala Ser Glu Leu Leu Ser Arg Ala Tyr Ala Tyr Gln
        195                 200                 205

Ala Gly Cys Tyr Val Leu Cys Ala Gly Gly Leu Gly Pro Ala Pro Gly
    210                 215                 220

Glu Leu Pro Asp Gly Ile Ala Ala Glu Ser Leu Asp His Leu Thr Gly
225                 230                 235                 240

Glu Ser Cys Ile Ile Asp Pro Trp Gly Lys Val Ile Ala Gly Pro Val
                245                 250                 255

Ser Cys Glu Glu Thr Leu Ile Thr Ala Arg Val Ser Thr Ala Ser Ile
            260                 265                 270

Tyr Arg Arg Lys Ser Leu Thr Asp Val Gly Gly His Tyr Ser Arg Pro
        275                 280                 285

Asp Val Phe Arg Phe Glu Val Asp Arg Ser Glu Arg Pro Arg Val Val
    290                 295                 300

Phe Arg Asp Gly Asp Val Asp Asp Arg Gly
```

<210> SEQ ID NO 5
<211> LENGTH: 969
<212> TYPE: DNA
<213> ORGANISM: Flavihumibacter solisilvae

<400> SEQUENCE: 5

```
atgagccata gtaccaataa taacagcagc accgttgttc gtgcagcagc cgtgcagatt      60
agcccggttc tgtatagtcg cgaaggcacc acccagaaag tggtgaatac cattcgtgaa     120
ctgggtaaac agggcgtgca gtttgcagtg tttccggaaa cctttattcc gtattatccg     180
tattttagtt tcgttcagcc gccgtatatg caggcagaac agcatctgaa actgatggaa     240
gaagcagtga ccgttccgag tgccaccacc gatgcaattg gcgaagccgc cgtgaagcc      300
ggtattgttg ttagtattgg cgtgaatgaa cgtgatggtg gtagtctgta taatacccag     360
ctgctgtttg atgccgatgg taccctgatt cagcgccgtc gcaaaattac cccgacctat     420
catgaacgca tggtttgggg tcagggcgat ggtagcggcc tgcgcgctgt ggatagtaaa     480
gcaggccgta ttggccagct ggcatgttgg aacattata atccgctggc ccgttatgca     540
atgattgccg atggtgaaca gattcatgca gcaatgtatc cggcagcag ctttggcgaa      600
ctgtttagcc agcagattga agttagtgtt cgtcagcatg ccctggaaag tgccgccttt     660
gttgttagta gcaccgcatg gctggatgcc gatcagcagg cccagattat gaaagatacc     720
ggcagcccga ttggtccgat tagcggtggt aattttaccg ccattattgc cccggatggt     780
accattattg gcgaaccgat tcgtagcggc gaaggctttg tgattgcaga tttggatttt     840
aatctgattg agaaacgcaa acgtctgatg gatctgaaag ccattataa tcgcccggaa      900
ctgctgagtc tgctgattga tcgcaccccg gccgaatatg ttcaggaagt gaataagagt     960
gttagcgaa                                                              969
```

<210> SEQ ID NO 6
<211> LENGTH: 323
<212> TYPE: PRT
<213> ORGANISM: Flavihumibacter solisilvae

<400> SEQUENCE: 6

```
Met Ser His Ser Thr Asn Asn Ser Ser Thr Val Val Arg Ala Ala
1               5                   10                  15

Ala Val Gln Ile Ser Pro Val Leu Tyr Ser Arg Glu Gly Thr Thr Gln
            20                  25                  30

Lys Val Val Asn Thr Ile Arg Glu Leu Gly Lys Gln Gly Val Gln Phe
        35                  40                  45

Ala Val Phe Pro Glu Thr Phe Ile Pro Tyr Tyr Pro Tyr Phe Ser Phe
    50                  55                  60

Val Gln Pro Pro Tyr Met Gln Ala Glu Gln His Leu Lys Leu Met Glu
65                  70                  75                  80

Glu Ala Val Thr Val Pro Ser Ala Thr Thr Asp Ala Ile Gly Glu Ala
                85                  90                  95

Ala Arg Glu Ala Gly Ile Val Val Ser Ile Gly Val Asn Glu Arg Asp
            100                 105                 110

Gly Gly Ser Leu Tyr Asn Thr Gln Leu Leu Phe Asp Ala Asp Gly Thr
        115                 120                 125

Leu Ile Gln Arg Arg Arg Lys Ile Thr Pro Thr Tyr His Glu Arg Met
    130                 135                 140
```

Val Trp Gly Gln Gly Asp Gly Ser Gly Leu Arg Ala Val Asp Ser Lys
145                 150                 155                 160

Ala Gly Arg Ile Gly Gln Leu Ala Cys Trp Glu His Tyr Asn Pro Leu
            165                 170                 175

Ala Arg Tyr Ala Met Ile Ala Asp Gly Glu Gln Ile His Ala Ala Met
            180                 185                 190

Tyr Pro Gly Ser Ser Phe Gly Glu Leu Phe Ser Gln Ile Glu Val
        195                 200                 205

Ser Val Arg Gln His Ala Leu Glu Ser Ala Ala Phe Val Val Ser Ser
    210                 215                 220

Thr Ala Trp Leu Asp Ala Asp Gln Gln Ala Gln Ile Met Lys Asp Thr
225                 230                 235                 240

Gly Ser Pro Ile Gly Pro Ile Ser Gly Gly Asn Phe Thr Ala Ile Ile
            245                 250                 255

Ala Pro Asp Gly Thr Ile Ile Gly Glu Pro Ile Arg Ser Gly Glu Gly
            260                 265                 270

Phe Val Ile Ala Asp Leu Asp Phe Asn Leu Ile Glu Lys Arg Lys Arg
            275                 280                 285

Leu Met Asp Leu Lys Gly His Tyr Asn Arg Pro Glu Leu Leu Ser Leu
290                 295                 300

Leu Ile Asp Arg Thr Pro Ala Glu Tyr Val Gln Glu Val Asn Lys Ser
305                 310                 315                 320

Val Ser Glu

<210> SEQ ID NO 7
<211> LENGTH: 1107
<212> TYPE: DNA
<213> ORGANISM: Acidovorax facilis
<220> FEATURE:
<223> OTHER INFORMATION: Acidovorax facilis 72W

<400> SEQUENCE: 7

```
atggtttctt acaactctaa attcctggct gctaccgttc aggctgaacc ggtttggctg     60
gacgctgacg ctaccatcga caaatctatc ggtatcatcg aagaagctgc tcagaaaggt    120
gcttctctga tcgctttccc ggaagttttc atcccgggtt accgtactg gcttggctg     180 ggtgacgtta atactctct gtctttcacc tctcgttacc acgaaaactc tctggaactg    240
ggtgacgacc gtatgcgtcg tctgcagctg gctgctcgtc gtaacaaaat cgctctggtt    300
atgggttact ctgaacgtga agctggttct cgttacctgt ctcaggtttt catcgacgaa    360
cgtggtgaaa tcgttgctaa ccgtcgtaaa ctgaaaccga cccacgttga acgtaccatc    420
tacggtgaag gtaacggtac cgacttcctg acccacgact cgctttcgg tcgtgttggt    480 ggtctgaact gctgggaaca cttccagccg ctgtctaaat tcatgatgta ctctctgggt    540
gaacaggttc acgttgcttc ttggccggct atgtctccgc tgcagccgga cgttttccag    600
ctgtctatcg aagctaacgc taccgttacc gttcttacg ctatcgaagg tcagaccttc    660
gttctgtgct ctacccaggt tatcggtccg tctgctatcg aaaccttctg cctgaacgac    720
gaacagcgtg ctctgctgcc gcaggggttgc ggttgggctc gtatctacgg tccggacggt    780
tctgaactgg ctaaaccgct ggctgaagac gctgaaggta tcctgtacgc tgaaatcgac    840
ctggaacaga tcctgctggc taaagctggt gctgacccgg ttggtcacta ctctcgtccg    900
gacgttctgt ctgttcagtt cgaccgcgct aaccacaccc cggttcaccg tatcggtatc    960
gacggtcgtc tggacgttaa caccgttct cgtgttgaaa acttccgtct gcgtcaggct   1020
```

```
gctgaacagg aacgtcaggc ttctaaacgt ctgggtacca aactgttcga acagtctctg    1080
ctggctgaag aaccggttcc ggctaaa                                        1107
```

<210> SEQ ID NO 8
<211> LENGTH: 369
<212> TYPE: PRT
<213> ORGANISM: Acidovorax facilis
<220> FEATURE:
<223> OTHER INFORMATION: Acidovorax facilis 72W

<400> SEQUENCE: 8

```
Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350
```

-continued

Thr Lys Leu Phe Glu Gln Ser Leu Leu Ala Glu Glu Pro Val Pro Ala
        355                 360                 365

Lys

<210> SEQ ID NO 9
<211> LENGTH: 975
<212> TYPE: DNA
<213> ORGANISM: Pseudomonas sp
<220> FEATURE:
<223> OTHER INFORMATION: Pseudomonas sp. RIT357

<400> SEQUENCE: 9

```
atgaccagca acgtgaaaaa aaccgtggcc attgtgcaga tgccggcagc actgctggat      60
cgcgccgaaa gtatgcgccg cgcagccgaa catattaaga aagcagccct gcaagaagca     120
cagctggtta ttttccgga aacctggctg agttgttatc cggcctgggt gtttggtatg      180
gccggttggg atgatgcaca ggcaaaaagc tggtatgcaa aactgctggc agatagtccg     240
gttattggtc agccggaaga tatgcatgat gatctgcag aactgcgtga agccgcccgc      300
gtgaatgccg tgaccgtggt tatgggcatg aatgaacgta gtcgtcatca tggtggtagc     360
ctgtataata gtctggttac cattggtccg atggtgcaa ttctgaatgt tcatcgtaaa      420
ctgaccccga cccataccga acgtaccgtt tgggcaaatg gtgacgcagc aggtctgcgc     480
gtggttgata ccgtggttgg tcgtgtgggt ggcctggttt gctgggaaca ttggcatccg     540
ctggcccgcc aggccctgca tgctcaagat gaacagattc atgttgcagc ctggccggat     600
atgccggaaa tgcatcatgt ggccgcccgc agctatgcat ttgaaggtcg ttgttttgtt     660
ctgtgtgcag gccagtatct ggcagcaggc gatgtgccgg cagaactgct ggccgcatat     720
cgccgtggcc ttggtggtaa agccctggaa gaagatgttc tgtttaatgg tggtagtggc     780
gttattgcac cggatggtag ttgggtgacc gcaccgctgt ttggcgaacc gggtattatt     840
ctggccacca ttgatctggc ccagattgat gcccagcatc atgatctgga tgtggcaggc     900
cattatctgc gtccggatgt gtttgaactg agtattgatc gccgcgttcg caccggtctg     960
accctgcgtg atgca                                                       975
```

<210> SEQ ID NO 10
<211> LENGTH: 325
<212> TYPE: PRT
<213> ORGANISM: Pseudomonas sp.
<220> FEATURE:
<223> OTHER INFORMATION: Pseudomonas sp. RIT357

<400> SEQUENCE: 10

Met Thr Ser Lys Arg Glu Lys Thr Val Ala Ile Val Gln Met Pro Ala
1               5                   10                  15

Ala Leu Leu Asp Arg Ala Glu Ser Met Arg Arg Ala Ala Glu His Ile
            20                  25                  30

Lys Lys Ala Ala Leu Gln Glu Ala Gln Leu Val Ile Phe Pro Glu Thr
        35                  40                  45

Trp Leu Ser Cys Tyr Pro Ala Trp Val Phe Gly Met Ala Gly Trp Asp
    50                  55                  60

Asp Ala Gln Ala Lys Ser Trp Tyr Ala Lys Leu Leu Ala Asp Ser Pro
65                  70                  75                  80

Val Ile Gly Gln Pro Glu Asp Met His Asp Asp Leu Ala Glu Leu Arg
                85                  90                  95

Glu Ala Ala Arg Val Asn Ala Val Thr Val Val Met Gly Met Asn Glu

|       |       |       | 100   |       |       |       | 105   |       |       |       | 110   |       |
|-------|-------|-------|-------|-------|-------|-------|-------|-------|-------|-------|-------|-------|
| Arg   | Ser   | Arg   | His   | His   | Gly   | Gly   | Ser   | Leu   | Tyr   | Asn   | Ser   | Leu   | Val   | Thr   | Ile   |
|       |       |       | 115   |       |       |       | 120   |       |       |       | 125   |       |

Arg Ser Arg His His Gly Gly Ser Leu Tyr Asn Ser Leu Val Thr Ile
               115                   120                   125

Gly Pro Asp Gly Ala Ile Leu Asn Val His Arg Lys Leu Thr Pro Thr
       130                 135                   140

His Thr Glu Arg Thr Val Trp Ala Asn Gly Asp Ala Ala Gly Leu Arg
145                 150                 155                 160

Val Val Asp Thr Val Val Gly Arg Val Gly Gly Leu Val Cys Trp Glu
             165                 170                 175

His Trp His Pro Leu Ala Arg Gln Ala Leu His Ala Gln Asp Glu Gln
       180                 185                   190

Ile His Val Ala Ala Trp Pro Asp Met Pro Glu Met His His Val Ala
             195                 200                 205

Ala Arg Ser Tyr Ala Phe Glu Gly Arg Cys Phe Val Leu Cys Ala Gly
       210                 215                   220

Gln Tyr Leu Ala Ala Gly Asp Val Pro Ala Glu Leu Leu Ala Ala Tyr
225                 230                 235                 240

Arg Arg Gly Val Gly Gly Lys Ala Leu Glu Glu Asp Val Leu Phe Asn
             245                 250                 255

Gly Gly Ser Gly Val Ile Ala Pro Asp Gly Ser Trp Val Thr Ala Pro
       260                 265                   270

Leu Phe Gly Glu Pro Gly Ile Ile Leu Ala Thr Ile Asp Leu Ala Gln
             275                 280                 285

Ile Asp Ala Gln His His Asp Leu Asp Val Ala Gly His Tyr Leu Arg
       290                 295                   300

Pro Asp Val Phe Glu Leu Ser Ile Asp Arg Arg Val Arg Thr Gly Leu
305                 310                 315                 320

Thr Leu Arg Asp Ala
             325

<210> SEQ ID NO 11
<211> LENGTH: 924
<212> TYPE: DNA
<213> ORGANISM: Nocardia brasiliensis
<220> FEATURE:
<223> OTHER INFORMATION: Nocardia brasiliensis NBRC 14402

<400> SEQUENCE: 11

| | | |
|---|---|---|
| atgcgtattg cagcagcaca ggcccgtccg gcatggctgg accctaccgc tggtaccaaa | 60 |
| attgtggtgg attggctgac caaagcagcc gccgcaggtg cagaactggt tgcatttccg | 120 |
| gaaacctttc tgagtggcta tccgatttgg ctggcccgta ccggtggtgc acgctttgat | 180 |
| aatccggcac agaaagccgc atacgcttat tatctgggcg ccgcagtgac cctggatggt | 240 |
| ccgcagctgg ataccgtgcg caccgcagca ggtgacctgg gcgttttctg ttatctgggc | 300 |
| attaccgaac gtgttcgtgg taccgtttat tgcaccctgg tggccattga tccggatcgt | 360 |
| ggcattgtgg gtgcccatcg caaactgatg ccgacccatg aagaacgtat ggtttggggc | 420 |
| attggcgatg gtaatggcct gcgtgcccat gattttggcg ttttcgtgt tagtggcctg | 480 |
| agttgttggg aaaattggat gccgcaggcc cgccatgccc tgtatgcaga tggtaccacc | 540 |
| ctgcatgtta gcacctggcc gggtagtatt cgtaatacca agatattac ccgttttatt | 600 |
| gccctggaag tcgtgtgta tagcctggcc gtgggtgccg tgctggatta tgcagatgtg | 660 |
| ccgaccgatt ttccgctgta tgaagaactg agcgcactgg ataaaccggc cggctatgat | 720 |
| ggcggcagtg ccgtggcagc cccggatggt acctggctgg ttgaaccggt ggtgggcacc | 780 |

-continued

```
gaacgcctga ttctggcaga tttggaccct gccgaagtgg caaaagaacg tcagaatttt    840
gatccgaccg gccattatgc acgcccggat atttttagtg tgaccgtgaa tcgccatcgt    900
cgtaccccgg caacctttct ggat                                           924
```

<210> SEQ ID NO 12
<211> LENGTH: 308
<212> TYPE: PRT
<213> ORGANISM: Nocardia brasiliensis
<220> FEATURE:
<223> OTHER INFORMATION: Nocardia brasiliensis NBRC 14402

<400> SEQUENCE: 12

```
Met Arg Ile Ala Ala Gln Ala Arg Pro Ala Trp Leu Asp Pro Thr
1               5                   10                  15

Ala Gly Thr Lys Ile Val Val Asp Trp Leu Thr Lys Ala Ala Ala
            20                  25                  30

Gly Ala Glu Leu Val Ala Phe Pro Glu Thr Phe Leu Ser Gly Tyr Pro
        35                  40                  45

Ile Trp Leu Ala Arg Thr Gly Gly Ala Arg Phe Asp Asn Pro Ala Gln
    50                  55                  60

Lys Ala Ala Tyr Ala Tyr Tyr Leu Gly Ala Ala Val Thr Leu Asp Gly
65                  70                  75                  80

Pro Gln Leu Asp Thr Val Arg Thr Ala Ala Gly Asp Leu Gly Val Phe
                85                  90                  95

Cys Tyr Leu Gly Ile Thr Glu Arg Val Arg Gly Thr Val Tyr Cys Thr
            100                 105                 110

Leu Val Ala Ile Asp Pro Asp Arg Gly Ile Val Gly Ala His Arg Lys
        115                 120                 125

Leu Met Pro Thr His Glu Glu Arg Met Val Trp Gly Ile Gly Asp Gly
    130                 135                 140

Asn Gly Leu Arg Ala His Asp Phe Gly Val Phe Arg Val Ser Gly Leu
145                 150                 155                 160

Ser Cys Trp Glu Asn Trp Met Pro Gln Ala Arg His Ala Leu Tyr Ala
                165                 170                 175

Asp Gly Thr Thr Leu His Val Ser Thr Trp Pro Gly Ser Ile Arg Asn
            180                 185                 190

Thr Lys Asp Ile Thr Arg Phe Ile Ala Leu Glu Gly Arg Val Tyr Ser
        195                 200                 205

Leu Ala Val Gly Ala Val Leu Asp Tyr Ala Asp Val Pro Thr Asp Phe
    210                 215                 220

Pro Leu Tyr Glu Glu Leu Ser Ala Leu Asp Lys Pro Ala Gly Tyr Asp
225                 230                 235                 240

Gly Gly Ser Ala Val Ala Ala Pro Asp Gly Thr Trp Leu Val Glu Pro
                245                 250                 255

Val Val Gly Thr Glu Arg Leu Ile Leu Ala Asp Leu Asp Pro Ala Glu
            260                 265                 270

Val Ala Lys Glu Arg Gln Asn Phe Asp Pro Thr Gly His Tyr Ala Arg
        275                 280                 285

Pro Asp Ile Phe Ser Val Thr Val Asn Arg His Arg Arg Thr Pro Ala
    290                 295                 300

Thr Phe Leu Asp
305
```

<210> SEQ ID NO 13

<211> LENGTH: 1059
<212> TYPE: DNA
<213> ORGANISM: Pseudomonas fluorescens

<400> SEQUENCE: 13

```
atgacggtgc ataaaaaaca gtacaaagta gccgcggtgc aggccgcccc tgcgttcctc      60
gacctggaag ctggcgtggc caaagccatc ggactgattg ctcaggcggc ggctgagggt     120
gcctcactgg tcgctttccc cgaagcgtgg ctgccggggt atccctggtg gatctggctg     180
gactccccgg ccggcggcat gcgcttcgtc agcgcaact  tcgacaatgc tctggaggtc     240
ggcagcgaac ccttcgagcg gctctgcagg gctgcggcac agcacaaaat ctacgtcgta     300
ctgggcttca ctgaacgctc tggcggcacc ttgtatttgg ctcaggcgat cattgatgat     360
tgcggtcggg tagtcgccac acggcgtaag ctcaagccga ctcacgtgga gcgctcagtc     420
tacgagaag  gcgacggtag tgaccttgct gtgcatgaca ctaccttggg tcgcttaggt     480
gccttgtgct gcgcggagca tatccagccg ctgtccaagt acgccatgta cgctcagcac     540
gaacaggtac atatcgcggc ctggcctagc ttttcggtat accgggggc  tgcgtttcaa     600
ctgagcgccc aagccaataa tgccgcctcg caagtctacg cactggaagg tcagtgtttt     660
gtgctggcgc atgcgccac  ggtgtccaaa gaaatgctcg acgaactgat tgattctccg     720
gccaaggctg agctgctgct ggaaggtggc ggcttcgcga tgatctacgg cccggatggc     780
gcaccgctgt gtacgccatt ggcggaaaca gaggagggca ttctctatgc ggatatcgac     840
ttgggggtga tcgggtggc  caaagctgcc tacgacccgg ttggtcacta ttcacgccct     900
gatgtgctgc ggttgctggt caaccgggag ccaatgacgc gtgtgcatta tgttcagccg     960
cagtcgttac cggagacatc ggtgttggcg ttcggtgcgg agcggatgc  catcagaagt    1020
gaggagaacc cagaagagca aggcgacaag ggatcctga                           1059
```

<210> SEQ ID NO 14
<211> LENGTH: 352
<212> TYPE: PRT
<213> ORGANISM: Pseudomonas fluorescens

<400> SEQUENCE: 14

```
Met Thr Val His Lys Lys Gln Tyr Lys Val Ala Ala Val Gln Ala Ala
1               5                   10                  15

Pro Ala Phe Leu Asp Leu Glu Ala Gly Val Ala Lys Ala Ile Gly Leu
            20                  25                  30

Ile Ala Gln Ala Ala Ala Glu Gly Ala Ser Leu Val Ala Phe Pro Glu
        35                  40                  45

Ala Trp Leu Pro Gly Tyr Pro Trp Trp Ile Trp Leu Asp Ser Pro Ala
    50                  55                  60

Gly Gly Met Arg Phe Val Gln Arg Asn Phe Asp Asn Ala Leu Glu Val
65                  70                  75                  80

Gly Ser Glu Pro Phe Glu Arg Leu Cys Arg Ala Ala Ala Gln His Lys
                85                  90                  95

Ile Tyr Val Val Leu Gly Phe Thr Glu Arg Ser Gly Gly Thr Leu Tyr
            100                 105                 110

Leu Ala Gln Ala Ile Ile Asp Asp Cys Gly Arg Val Val Ala Thr Arg
        115                 120                 125

Arg Lys Leu Lys Pro Thr His Val Glu Arg Ser Val Tyr Gly Glu Gly
    130                 135                 140

Asp Gly Ser Asp Leu Ala Val His Asp Thr Thr Leu Gly Arg Leu Gly
145                 150                 155                 160
```

```
Ala Leu Cys Cys Ala Glu His Ile Gln Pro Leu Ser Lys Tyr Ala Met
                165                 170                 175

Tyr Ala Gln His Glu Gln Val His Ile Ala Ala Trp Pro Ser Phe Ser
            180                 185                 190

Val Tyr Arg Gly Ala Ala Phe Gln Leu Ser Ala Gln Ala Asn Asn Ala
        195                 200                 205

Ala Ser Gln Val Tyr Ala Leu Glu Gly Gln Cys Phe Val Leu Ala Pro
    210                 215                 220

Cys Ala Thr Val Ser Lys Glu Met Leu Asp Glu Leu Ile Asp Ser Pro
225                 230                 235                 240

Ala Lys Ala Glu Leu Leu Leu Glu Gly Gly Phe Ala Met Ile Tyr
                245                 250                 255

Gly Pro Asp Gly Ala Pro Leu Cys Thr Pro Leu Ala Glu Thr Glu Glu
            260                 265                 270

Gly Ile Leu Tyr Ala Asp Ile Asp Leu Gly Val Ile Gly Val Ala Lys
        275                 280                 285

Ala Ala Tyr Asp Pro Val Gly His Tyr Ser Arg Pro Asp Val Leu Arg
    290                 295                 300

Leu Leu Val Asn Arg Glu Pro Met Thr Arg Val His Tyr Val Gln Pro
305                 310                 315                 320

Gln Ser Leu Pro Glu Thr Ser Val Leu Ala Phe Gly Ala Gly Ala Asp
                325                 330                 335

Ala Ile Arg Ser Glu Glu Asn Pro Glu Glu Gln Gly Asp Lys Gly Ser
            340                 345                 350
```

<210> SEQ ID NO 15
<211> LENGTH: 1041
<212> TYPE: DNA
<213> ORGANISM: Agrobacterium rubi

<400> SEQUENCE: 15

```
atggaaaaga gtaagaccgt gcgtgccgcc gccgcccaga ttgctcctga tctgaccagt      60
cgcgataata ccctggcacg cgttctggat accattcatg aagcagccgg caaaggtgca     120
gaactgattg tgtttccgga aacctttgtg ccgtggtatc cgtattttag ttttgttctg     180
ccgccggttc tgagtggccg tgaacatctg cgtctgtatg aagaagcagt taccgttccg     240
agtgccacca ccgatgcagt ggccaccgca gcacgcgaac atggtattgt ggtggcactg     300
ggtgtgaatg aacgtgatca tggcaccctg tataatcccc agctggtgtt tgatgcagat     360
ggcgccctgg tgctgaaacg tcgcaaaatt accccgacct ttcatgaacg tatgatttgg     420
ggccagggtg acgcaagtgg cctgaaagtg gtggatagcc aggttggccg cattggtgca     480
ctggcctgct gggaacatta taatccgctg cacgttatg ccctgatggc ccagcatgaa     540
gaaattcatg ttgcccagtt tccgggcagc atggtgggcc gattttttgc agatcagatg     600
gaagtgacca ttcgtcatca tgcactggaa agtggttgtt ttgtggttaa tgccaccggt     660
tggctgaccg atgaacagat tcgtagtatt accccggatg aaaatctgca aaaagcactg     720
cgcggtggct gcatgaccgc cattattagt ccggaaggta acatctggc acccgccgatg     780
accgaaggtg aaggcattct ggtggcagat ttggatatga gcctgattct gaaacgtaaa     840
cgtatgatgg atagtgtggg tcattatgcc cgcccggaac tgctgcatct ggttattgat     900
aatcgtccgg ccattaccat ggtgaccgcc atccgtttc tggaaaccgc accgaccggt     960
agtaataccg atggccatca gaccagcgcc tttgatggca tccggatca gcgcgccgca    1020
```
attctgcgcc gtcaggcagg c					1041

<210> SEQ ID NO 16
<211> LENGTH: 347
<212> TYPE: PRT
<213> ORGANISM: Agrobacterium rubi

<400> SEQUENCE: 16

```
Met Glu Lys Ser Lys Thr Val Arg Ala Ala Ala Gln Ile Ala Pro
1               5                   10                  15

Asp Leu Thr Ser Arg Asp Asn Thr Leu Ala Arg Val Leu Asp Thr Ile
                20                  25                  30

His Glu Ala Ala Gly Lys Gly Ala Glu Leu Ile Val Phe Pro Glu Thr
            35                  40                  45

Phe Val Pro Trp Tyr Pro Tyr Phe Ser Phe Val Leu Pro Pro Val Leu
        50                  55                  60

Ser Gly Arg Glu His Leu Arg Leu Tyr Glu Glu Ala Val Thr Val Pro
65                  70                  75                  80

Ser Ala Thr Thr Asp Ala Val Ala Thr Ala Ala Arg Glu His Gly Ile
                85                  90                  95

Val Val Ala Leu Gly Val Asn Glu Arg Asp His Gly Thr Leu Tyr Asn
            100                 105                 110

Thr Gln Leu Val Phe Asp Ala Asp Gly Ala Leu Val Leu Lys Arg Arg
        115                 120                 125

Lys Ile Thr Pro Thr Phe His Glu Arg Met Ile Trp Gly Gln Gly Asp
130                 135                 140

Ala Ser Gly Leu Lys Val Val Asp Ser Gln Val Gly Arg Ile Gly Ala
145                 150                 155                 160

Leu Ala Cys Trp Glu His Tyr Asn Pro Leu Ala Arg Tyr Ala Leu Met
                165                 170                 175

Ala Gln His Glu Glu Ile His Val Ala Gln Phe Pro Gly Ser Met Val
            180                 185                 190

Gly Pro Ile Phe Ala Asp Gln Met Glu Val Thr Ile Arg His His Ala
        195                 200                 205

Leu Glu Ser Gly Cys Phe Val Val Asn Ala Thr Gly Trp Leu Thr Asp
        210                 215                 220

Glu Gln Ile Arg Ser Ile Thr Pro Asp Glu Asn Leu Gln Lys Ala Leu
225                 230                 235                 240

Arg Gly Gly Cys Met Thr Ala Ile Ile Ser Pro Glu Gly Lys His Leu
                245                 250                 255

Ala Pro Pro Met Thr Glu Gly Glu Gly Ile Leu Val Ala Asp Leu Asp
            260                 265                 270

Met Ser Leu Ile Leu Lys Arg Lys Arg Met Met Asp Ser Val Gly His
        275                 280                 285

Tyr Ala Arg Pro Glu Leu Leu His Leu Val Ile Asp Asn Arg Pro Ala
        290                 295                 300

Ile Thr Met Val Thr Ala His Pro Phe Leu Glu Thr Ala Pro Thr Gly
305                 310                 315                 320

Ser Asn Thr Asp Gly His Gln Thr Ser Ala Phe Asp Gly Asn Pro Asp
                325                 330                 335

Gln Arg Ala Ala Ile Leu Arg Arg Gln Ala Gly
            340                 345
```

<210> SEQ ID NO 17
<211> LENGTH: 990

```
<212> TYPE: DNA
<213> ORGANISM: Unknown
<220> FEATURE:
<223> OTHER INFORMATION: Unknown prokaryotic organism

<400> SEQUENCE: 17
atgaaggtgg ttaaagcagc agcagttcag attagcccgg ttctgtatag tcgcgaagcc      60
accgttgaaa aagttgttaa aaagattcac gagctgggcc agctgggtgt gcagtttgca     120
acctttccgg aaaccgttgt tccgtattat ccgtatttta gtgcagttca gaccggtatt     180
gaactgctga gtggcaccga acatctgcgc ctgctggatc aggccgtgac cgttccgagt     240
ccggcaaccg atgcaattgg tgaagccgcc gcaaagccg gtatggttgt gagtattggt      300
gttaatgaac gtgatggtgg caccctgtat aatacccagc tgctgtttga tgcagatggt     360
acactgattc agcgtcgtcg taaaattacc ccgacccatt ttgaacgcat gatttggggt     420
cagggtgacg gtagcggtct gcgtgcagtt gatagtaaag ttggtcgcat tggtcagctg     480
gcatgttttg aacataataa tccgctggcc cgctatgcac tgattgcaga tggtgaacag     540
attcatagcg caatgtatcc gggcagtgcc tttggtgaag ttttgcaca gcgtatggaa      600
attaatattc gtcagcatgc actggaaagt ggcgcatttg tggtgaatgc aaccgcatgg     660
ctggatgcag atcagcaggc acagattatt aaggataccg ttgtggtat tggtccgatt      720
agcggcggtt gttttaccac cattgtggca ccggatggta tgctgatggc cgaaccgctg     780
cgtagtggcg aaggcgaagt gattgttgat ctggatttta ccctgattga tcgccgcaaa     840
atgctgatgg atagcgcagg ccattataat cgtccggaac tgctgagcct gatgattgat     900
cgcaccgcaa ccgcccatgt tcatgaacgc gccgcacatc cggtgagtgg tgccgaacag     960
ggcccggaag atttgcgcac cccggccgct                                      990

<210> SEQ ID NO 18
<211> LENGTH: 330
<212> TYPE: PRT
<213> ORGANISM: Unknown
<220> FEATURE:
<223> OTHER INFORMATION: Unknown prokaryotic organism

<400> SEQUENCE: 18

Met Lys Val Val Lys Ala Ala Val Gln Ile Ser Pro Val Leu Tyr
1               5                   10                  15

Ser Arg Glu Ala Thr Val Glu Lys Val Val Lys Lys Ile His Glu Leu
                20                  25                  30

Gly Gln Leu Gly Val Gln Phe Ala Thr Phe Pro Glu Thr Val Val Pro
        35                  40                  45

Tyr Tyr Pro Tyr Phe Ser Ala Val Gln Thr Gly Ile Glu Leu Leu Ser
    50                  55                  60

Gly Thr Glu His Leu Arg Leu Leu Asp Gln Ala Val Thr Val Pro Ser
65                  70                  75                  80

Pro Ala Thr Asp Ala Ile Gly Glu Ala Ala Arg Lys Ala Gly Met Val
                85                  90                  95

Val Ser Ile Gly Val Asn Glu Arg Asp Gly Gly Thr Leu Tyr Asn Thr
            100                 105                 110

Gln Leu Leu Phe Asp Ala Asp Gly Thr Leu Ile Gln Arg Arg Arg Lys
        115                 120                 125

Ile Thr Pro Thr His Phe Glu Arg Met Ile Trp Gly Gln Gly Asp Gly
    130                 135                 140

Ser Gly Leu Arg Ala Val Asp Ser Lys Val Gly Arg Ile Gly Gln Leu
```

```
                145                 150                 155                 160
Ala Cys Phe Glu His Asn Asn Pro Leu Ala Arg Tyr Ala Leu Ile Ala
                    165                 170                 175
Asp Gly Glu Gln Ile His Ser Ala Met Tyr Pro Gly Ser Ala Phe Gly
                180                 185                 190
Glu Gly Phe Ala Gln Arg Met Glu Ile Asn Ile Arg Gln His Ala Leu
                195                 200                 205
Glu Ser Gly Ala Phe Val Val Asn Ala Thr Ala Trp Leu Asp Ala Asp
            210                 215                 220
Gln Gln Ala Gln Ile Ile Lys Asp Thr Gly Cys Gly Ile Gly Pro Ile
225                 230                 235                 240
Ser Gly Gly Cys Phe Thr Thr Ile Val Ala Pro Asp Gly Met Leu Met
                    245                 250                 255
Ala Glu Pro Leu Arg Ser Gly Glu Gly Glu Val Ile Val Asp Leu Asp
                260                 265                 270
Phe Thr Leu Ile Asp Arg Arg Lys Met Leu Met Asp Ser Ala Gly His
                275                 280                 285
Tyr Asn Arg Pro Glu Leu Leu Ser Leu Met Ile Asp Arg Thr Ala Thr
            290                 295                 300
Ala His Val His Glu Arg Ala Ala His Pro Val Ser Gly Ala Glu Gln
305                 310                 315                 320
Gly Pro Glu Asp Leu Arg Thr Pro Ala Ala
                325                 330

<210> SEQ ID NO 19
<211> LENGTH: 1158
<212> TYPE: DNA
<213> ORGANISM: Candidatus Dadabacteria
<220> FEATURE:
<223> OTHER INFORMATION: Candidatus Dadabacteria bacterium CSP1-2

<400> SEQUENCE: 19
atgggtcagg tgctgggtgg tcgtgaacag gttcgtgccg ccgtggttca ggcaagtccg        60 gttttttatga ataagaaagg ttgtctggaa aaggcctgcg atctgattca taaagcaggt     120
aaagaaggcg cagaaattgt ggtgtttccg gaaacctgga ttccgaccta tccgtattgg       180
ggtatgggtt gggataccgc agcagcagca tttgccgatg ttcatgccga tctgcaagat     240
aatagcctgt ggttggcag caaagatacc gatattctgg gtaaagcagc ccgcgatgcc       300
ggtgcctatg ttgttatggg ctgcaatgaa ctggatgatc gcattggcag ccgtaccctg       360
tttaatagtc tggtttatat tggcaaagac ggccgtgtta tgggtcgtca tcgtaaactg       420
attccgagtt atattgaacg catttggtgg ggtcgcggtg acgcccgtga tctgaaagtt       480
tttgataccg atatcggccg cattggtggt cagatttgtt gggaaaatca tattgttaac     540
atcaccgcct ggtttattgc ccagggcgtt gatattcatg ttgcagtttg ccgggtctg       600 tggaattgtg gtgccgcaca gggtgaaagt tttatctatg caggccatga tattaataag     660
tgcgatctga tcccggccac ccgcgaacgc gcctttaccg gtcagtgctt tgttctgagc     720
gcaaataata ttctgcgcat ggatgaaatt ccggatgatt ttccgtttaa aaataagatg     780
acctacgcag gtccgggtca gggtgaattt gttggctggg catgtggtgg tagtcatatt     840
gttgcaccga ccagcgaata tattgtgccg ccgaccttg atgttgaaac cattctgtat     900
gcagatttga atgccaaata tattaaggtt gtgaagagcg ttttcgatag tctgggccat     960
tatacccgct gggatctggt gagtctgacc aaacagccgc agccgtatga accgctggca   1020
```

-continued

```
ggcgaacgcc cgatggcaat gccggaagaa cgtattgaac aggttgccga tgcagtggcc    1080
cgtgagttta atctggatgt tgaaaaagtt gataagatcg tgcgtcaggt taccaccccg    1140
catcgtcagc gcgcagcc                                                  1158
```

<210> SEQ ID NO 20
<211> LENGTH: 386
<212> TYPE: PRT
<213> ORGANISM: Candidatus Dadabacteria
<220> FEATURE:
<223> OTHER INFORMATION: Candidatus Dadabacteria bacterium CSP1-2

<400> SEQUENCE: 20

```
Met Gly Gln Val Leu Gly Gly Arg Glu Gln Val Arg Ala Ala Val Val
1               5                   10                  15

Gln Ala Ser Pro Val Phe Met Asn Lys Lys Gly Cys Leu Glu Lys Ala
            20                  25                  30

Cys Asp Leu Ile His Lys Ala Gly Lys Glu Gly Ala Glu Ile Val Val
        35                  40                  45

Phe Pro Glu Thr Trp Ile Pro Thr Tyr Pro Tyr Trp Gly Met Gly Trp
    50                  55                  60

Asp Thr Ala Ala Ala Phe Asp Val His Ala Asp Leu Gln Asp
65                  70                  75                  80

Asn Ser Leu Val Val Gly Ser Lys Asp Thr Asp Ile Leu Gly Lys Ala
                85                  90                  95

Ala Arg Asp Ala Gly Ala Tyr Val Val Met Gly Cys Asn Glu Leu Asp
            100                 105                 110

Asp Arg Ile Gly Ser Arg Thr Leu Phe Asn Ser Leu Val Tyr Ile Gly
        115                 120                 125

Lys Asp Gly Arg Val Met Gly Arg His Arg Lys Leu Ile Pro Ser Tyr
    130                 135                 140

Ile Glu Arg Ile Trp Trp Gly Arg Gly Asp Ala Arg Asp Leu Lys Val
145                 150                 155                 160

Phe Asp Thr Asp Ile Gly Arg Ile Gly Gly Gln Ile Cys Trp Glu Asn
                165                 170                 175

His Ile Val Asn Ile Thr Ala Trp Phe Ile Ala Gln Gly Val Asp Ile
            180                 185                 190

His Val Ala Val Trp Pro Gly Leu Trp Asn Cys Gly Ala Ala Gln Gly
        195                 200                 205

Glu Ser Phe Ile Tyr Ala Gly His Asp Ile Asn Lys Cys Asp Leu Ile
    210                 215                 220

Pro Ala Thr Arg Glu Arg Ala Phe Thr Gly Gln Cys Phe Val Leu Ser
225                 230                 235                 240

Ala Asn Asn Ile Leu Arg Met Asp Glu Ile Pro Asp Asp Phe Pro Phe
                245                 250                 255

Lys Asn Lys Met Thr Tyr Ala Gly Pro Gly Gln Gly Glu Phe Val Gly
            260                 265                 270

Trp Ala Cys Gly Gly Ser His Ile Val Ala Pro Thr Ser Glu Tyr Ile
        275                 280                 285

Val Pro Pro Thr Phe Asp Val Glu Thr Ile Leu Tyr Ala Asp Leu Asn
    290                 295                 300

Ala Lys Tyr Ile Lys Val Val Lys Ser Val Phe Asp Ser Leu Gly His
305                 310                 315                 320

Tyr Thr Arg Trp Asp Leu Val Ser Leu Thr Lys Gln Pro Gln Pro Tyr
                325                 330                 335
```

Glu Pro Leu Ala Gly Glu Arg Pro Met Ala Met Pro Glu Glu Arg Ile
            340                 345                 350

Glu Gln Val Ala Asp Ala Val Ala Arg Glu Phe Asn Leu Asp Val Glu
        355                 360                 365

Lys Val Asp Lys Ile Val Arg Gln Val Thr Thr Pro His Arg Gln Arg
    370                 375                 380

Ala Ala
385

<210> SEQ ID NO 21
<211> LENGTH: 963
<212> TYPE: DNA
<213> ORGANISM: Unknown
<220> FEATURE:
<223> OTHER INFORMATION: Unknown prokaryotic organism

<400> SEQUENCE: 21

```
atgtcaaacg agaacaacaa cgctacattc aaagttgccg cagtacaggc tacacctgtt      60
tttctcgatc gtgaagcgac tctcgacaag gcttgcgatt tgatcgccgc cgccggaggt     120
gaagggcac gattggttgt cttttccagaa gccttcatac cggcctatcc ggattgggta     180
tgggcaatcc caccgggtga agagggcgta cttaatgagt tgtacgcaga gctgctctcc     240
aactcggtca cgattcccag tgacgcgacg acagactgt gccgggccgc gaggcttgct      300
aatgcttacg tggtgatggg gataagcgaa cgcaatgtcg aggcgagtgg agcaagcctg     360
tataacacgc tgttgtacat cgatgcgcag ggtgagattc taggcaaaca tcgaaagcta     420
gtgccaacgg gcggcgagcg gctggtgtgg gcgcagggcg atggcagcac actgcaggtc     480
tacgatactc cactgggaaa actcggcggt ttaatttgct gggagaatta tatgccgctg     540
gcccgctata ccatgtatgc ctggggcaca caaatctatg tcgccgctac gtgggatcgc     600
gggcaaccct ggctctccac tttgcggcat atcgccaaag aaggcagggt gtacgtgatt     660
ggttgttgta tcgcgatgcg caaagacgat atccctgatc gttacgcaat gaagcagaag     720
ttttacgcgg aggcagatga gtggatcaat ataggtgaca gcgcgattgt caatcctgaa     780
gggcaattta tcgcagggcc agtacgcaag caggaagaga ttctctacgc agagattgat     840
ccgcgcatgg tacaagggcc gaagtggatg ctcgacgtgg cggggcacta tgccaggccg     900
gatgtgttcc agttgacggt gcatacggat gtgcgacaga tgattcggat ggaacacgat     960
tct                                                                    963
```

<210> SEQ ID NO 22
<211> LENGTH: 321
<212> TYPE: PRT
<213> ORGANISM: Unknown
<220> FEATURE:
<223> OTHER INFORMATION: Unknown prokaryotic organism

<400> SEQUENCE: 22

Met Ser Asn Glu Asn Asn Asn Ala Thr Phe Lys Val Ala Ala Val Gln
1               5                   10                  15

Ala Thr Pro Val Phe Leu Asp Arg Glu Ala Thr Leu Asp Lys Ala Cys
            20                  25                  30

Asp Leu Ile Ala Ala Ala Gly Gly Glu Gly Ala Arg Leu Val Val Phe
        35                  40                  45

Pro Glu Ala Phe Ile Pro Ala Tyr Pro Asp Trp Val Trp Ala Ile Pro
    50                  55                  60

Pro Gly Glu Glu Gly Val Leu Asn Glu Leu Tyr Ala Glu Leu Leu Ser

```
              65                  70                  75                  80
        Asn Ser Val Thr Ile Pro Ser Asp Ala Thr Asp Arg Leu Cys Arg Ala
                         85                  90                  95

Ala Arg Leu Ala Asn Ala Tyr Val Met Gly Ile Ser Glu Arg Asn
                100                 105                 110

Val Glu Ala Ser Gly Ala Ser Leu Tyr Asn Thr Leu Leu Tyr Ile Asp
                    115                 120                 125

Ala Gln Gly Glu Ile Leu Gly Lys His Arg Lys Leu Val Pro Thr Gly
            130                 135                 140

Gly Glu Arg Leu Val Trp Ala Gln Gly Asp Gly Ser Thr Leu Gln Val
        145                 150                 155                 160

Tyr Asp Thr Pro Leu Gly Lys Leu Gly Leu Ile Cys Trp Glu Asn
                        165                 170                 175

Tyr Met Pro Leu Ala Arg Tyr Thr Met Tyr Ala Trp Gly Thr Gln Ile
                    180                 185                 190

Tyr Val Ala Ala Thr Trp Asp Arg Gly Gln Pro Trp Leu Ser Thr Leu
                195                 200                 205

Arg His Ile Ala Lys Glu Gly Arg Val Tyr Val Ile Gly Cys Cys Ile
            210                 215                 220

Ala Met Arg Lys Asp Asp Ile Pro Asp Arg Tyr Ala Met Lys Gln Lys
        225                 230                 235                 240

Phe Tyr Ala Glu Ala Asp Glu Trp Ile Asn Ile Gly Asp Ser Ala Ile
                        245                 250                 255

Val Asn Pro Glu Gly Gln Phe Ile Ala Gly Pro Val Arg Lys Gln Glu
                    260                 265                 270

Glu Ile Leu Tyr Ala Glu Ile Asp Pro Arg Met Val Gln Gly Pro Lys
                275                 280                 285

Trp Met Leu Asp Val Ala Gly His Tyr Ala Arg Pro Asp Val Phe Gln
            290                 295                 300

Leu Thr Val His Thr Asp Val Arg Gln Met Ile Arg Met Glu His Asp
        305                 310                 315                 320

Ser
```

<210> SEQ ID NO 23

<400> SEQUENCE: 23

000

<210> SEQ ID NO 24

<400> SEQUENCE: 24

000

<210> SEQ ID NO 25
<211> LENGTH: 972
<212> TYPE: DNA
<213> ORGANISM: Tepidicaulis marinus

<400> SEQUENCE: 25

```
atgacccgtg ttgctgctat ccagatggaa gctaaagttg ctgacctgaa cttcaacatc      60
gaccaggctt ctcgtctgat cgacgaagct ggttctaaag gtgctgaaat catcgctctg     120
ccggaattct tcaccacccg tatcgtttac gacgaacgtc tgttcgaatg ctctctgccg     180 ccggaaaaacc cggctctgga catgctgaaa gctaaagctc taaatacgg tgctatgatc     240
```

```
ggtggttctt acctggaaat gcgtgacggt gacgtttaca acacctacac cctggttgaa      300
ccggacggta ccgttcaccg tcacgacaaa gaccgtccga ccatggttga aaacgctttc      360
tacaccggtg ttctgacga cggttacttc gaaaccgcta tgggtccggt tggtaccgct      420
gtttgctggg aactgatccg taccgctacc gttcgtcgtc tggctggtaa agttggtctg      480
atgatgaccg ttctcactg gtggtctgct ccgggttgga acttctggaa atctttcgaa      540
cgtcgtttcc acaaagctaa cggtaaagct atggaaatca ccccgccgcg tttcgcttct      600
ctggttggtg ctccgctgct gcacgctggt cacaccggta tgctggaagg tggtttcctg      660
gttctgccgg gtaccgtat ctctgttccg accgtacc agctgatggg tgaaacccag        720
atcatcgacg gtgaaggtgc tgttgttgct cgtcgtcact acaccgaagg tgctggtatc      780
gttggtggtg aaatcgaact gggtgctacc tctccgaaaa aagctccgcc ggaccgtttc      840
tggatcccga acctggaagg tttcccgaaa gctctgtggc tgcaccagaa cccggctggt      900
gcttctgttt accgttgggc taaacgtacc ggtcgtctga aaacctacga cttctctcgt      960
aacgctcgtc cg                                                         972
```

<210> SEQ ID NO 26
<211> LENGTH: 324
<212> TYPE: PRT
<213> ORGANISM: Tepidicaulis marinus

<400> SEQUENCE: 26

```
Met Thr Arg Val Ala Ala Ile Gln Met Glu Ala Lys Val Ala Asp Leu
1               5                   10                  15

Asn Phe Asn Ile Asp Gln Ala Ser Arg Leu Ile Asp Glu Ala Gly Ser
            20                  25                  30

Lys Gly Ala Glu Ile Ile Ala Leu Pro Glu Phe Phe Thr Thr Arg Ile
        35                  40                  45

Val Tyr Asp Glu Arg Leu Phe Glu Cys Ser Leu Pro Pro Glu Asn Pro
    50                  55                  60

Ala Leu Asp Met Leu Lys Ala Lys Ala Ala Lys Tyr Gly Ala Met Ile
65                  70                  75                  80

Gly Gly Ser Tyr Leu Glu Met Arg Asp Gly Asp Val Tyr Asn Thr Tyr
                85                  90                  95

Thr Leu Val Glu Pro Asp Gly Thr Val His Arg His Asp Lys Asp Arg
            100                 105                 110

Pro Thr Met Val Glu Asn Ala Phe Tyr Thr Gly Gly Ser Asp Asp Gly
        115                 120                 125

Tyr Phe Glu Thr Ala Met Gly Pro Val Gly Thr Ala Val Cys Trp Glu
    130                 135                 140

Leu Ile Arg Thr Ala Thr Val Arg Arg Leu Ala Gly Lys Val Gly Leu
145                 150                 155                 160

Met Met Thr Gly Ser His Trp Trp Ser Ala Pro Gly Trp Asn Phe Trp
                165                 170                 175

Lys Ser Phe Glu Arg Arg Phe His Lys Ala Asn Gly Lys Ala Met Glu
            180                 185                 190

Ile Thr Pro Pro Arg Phe Ala Ser Leu Val Gly Ala Pro Leu Leu His
        195                 200                 205

Ala Gly His Thr Gly Met Leu Glu Gly Gly Phe Leu Val Leu Pro Gly
    210                 215                 220

Thr Arg Ile Ser Val Pro Thr Arg Thr Gln Leu Met Gly Glu Thr Gln
225                 230                 235                 240
```

```
Ile Ile Asp Gly Glu Gly Ala Val Val Ala Arg Arg His Tyr Thr Glu
            245                 250                 255

Gly Ala Gly Ile Val Gly Gly Glu Ile Glu Leu Gly Ala Thr Ser Pro
        260                 265                 270

Lys Lys Ala Pro Pro Asp Arg Phe Trp Ile Pro Asn Leu Glu Gly Phe
    275                 280                 285

Pro Lys Ala Leu Trp Leu His Gln Asn Pro Ala Gly Ala Ser Val Tyr
290                 295                 300

Arg Trp Ala Lys Arg Thr Gly Arg Leu Lys Thr Tyr Asp Phe Ser Arg
305                 310                 315                 320

Asn Ala Arg Pro

<210> SEQ ID NO 27
<211> LENGTH: 1014
<212> TYPE: DNA
<213> ORGANISM: Unknown
<220> FEATURE:
<223> OTHER INFORMATION: Unknown prokaryotic organism

<400> SEQUENCE: 27
atgggtatcg aacacccgaa atacaaagtt gctgttgttc aggctgctcc ggcttggctg      60
gacctggacg cttctatcga caaatctatc gctctgatcg aagaagctgc tcagaaaggt     120
gctaaactga tcgctttccc ggaagctttc atcccgggtt accgtggca catctggatg      180
gactctccgg cttgggctat cggtcgtggt ttcgttcagc gttacttcga caactctctg     240
gcttacgact ctccgcaggc tgaaaaactg cgtgctgctg ttcgtaaagc taaactgacc     300
gctgttctgg gtctgtctga acgtgacggt ggttctctgt acctggctca gtggctgatc     360
ggtccggacg tgaaaccat cgctaaacgt cgtaaactgc gtccgaccca cgctgaacgt     420
accgtttacg gtgaaggtga cggttctgac ctggctgttc acaaccgtcc ggacatcggt     480
cgtctgggtg ctctgtgctg ctgggaacac ctgcagccgc tgtctaaata cgctatgtac     540
gctcagaacg aacaggttca cgttgctgct tggccgtctt tctctctgta cgacccgttc     600
gctgttgctc tgggtgctga agttaacaac gctgcttctc gtgtttacgc tgttgaaggt     660
tcttgcttcg ttctggctcc gtgcgctacc gtttctcagg ctatgatcga cgaactgtgc     720
gaccgtccgg acaaacacac cctgctgcac gttggtggtg gtttcgctgc tatctacggt     780
ccggacggtt tcagatcgg tgacaaactg gctccggacc aggaaggtct gctgatcgct     840
gaaatcgacc tgggtgctat cggtgttgct aaaaacgctg ctgacccggc tggtcactac     900
tctcgtccgg acgttacccg tctgctgctg aacaaaaaac gtacaaacg tgttgaacag     960
ttctctccgc cggctgaagc tgttgaaccg accgacatcg ctgctgctgc ttct         1014

<210> SEQ ID NO 28
<211> LENGTH: 338
<212> TYPE: PRT
<213> ORGANISM: Unknown
<220> FEATURE:
<223> OTHER INFORMATION: Unknown prokaryotic organism

<400> SEQUENCE: 28

Met Gly Ile Glu His Pro Lys Tyr Lys Val Ala Val Val Gln Ala Ala
1               5                   10                  15

Pro Ala Trp Leu Asp Leu Asp Ala Ser Ile Asp Lys Ser Ile Ala Leu
            20                  25                  30

Ile Glu Glu Ala Ala Gln Lys Gly Ala Lys Leu Ile Ala Phe Pro Glu
        35                  40                  45
```

Ala Phe Ile Pro Gly Tyr Pro Trp His Ile Trp Met Asp Ser Pro Ala
                50                  55                  60

Trp Ala Ile Gly Arg Gly Phe Val Gln Arg Tyr Phe Asp Asn Ser Leu
 65                  70                  75                  80

Ala Tyr Asp Ser Pro Gln Ala Glu Lys Leu Arg Ala Ala Val Arg Lys
                85                  90                  95

Ala Lys Leu Thr Ala Val Leu Gly Leu Ser Glu Arg Asp Gly Gly Ser
                100                 105                 110

Leu Tyr Leu Ala Gln Trp Leu Ile Gly Pro Asp Gly Glu Thr Ile Ala
                115                 120                 125

Lys Arg Arg Lys Leu Arg Pro Thr His Ala Glu Arg Thr Val Tyr Gly
130                 135                 140

Glu Gly Asp Gly Ser Asp Leu Ala Val His Asn Arg Pro Asp Ile Gly
145                 150                 155                 160

Arg Leu Gly Ala Leu Cys Cys Trp Glu His Leu Gln Pro Leu Ser Lys
                165                 170                 175

Tyr Ala Met Tyr Ala Gln Asn Glu Gln Val His Val Ala Ala Trp Pro
                180                 185                 190

Ser Phe Ser Leu Tyr Asp Pro Phe Ala Val Ala Leu Gly Ala Glu Val
                195                 200                 205

Asn Asn Ala Ala Ser Arg Val Tyr Ala Val Glu Gly Ser Cys Phe Val
210                 215                 220

Leu Ala Pro Cys Ala Thr Val Ser Gln Ala Met Ile Asp Glu Leu Cys
225                 230                 235                 240

Asp Arg Pro Asp Lys His Thr Leu Leu His Val Gly Gly Gly Phe Ala
                245                 250                 255

Ala Ile Tyr Gly Pro Asp Gly Ser Gln Ile Gly Asp Lys Leu Ala Pro
                260                 265                 270

Asp Gln Glu Gly Leu Leu Ile Ala Glu Ile Asp Leu Gly Ala Ile Gly
                275                 280                 285

Val Ala Lys Asn Ala Ala Asp Pro Ala Gly His Tyr Ser Arg Pro Asp
290                 295                 300

Val Thr Arg Leu Leu Leu Asn Lys Lys Pro Tyr Lys Arg Val Glu Gln
305                 310                 315                 320

Phe Ser Pro Pro Ala Glu Ala Val Glu Pro Thr Asp Ile Ala Ala Ala
                325                 330                 335

Ala Ser

<210> SEQ ID NO 29
<211> LENGTH: 1014
<212> TYPE: DNA
<213> ORGANISM: Unknown
<220> FEATURE:
<223> OTHER INFORMATION: Unknown prokaryotic organism

<400> SEQUENCE: 29
atgggtatcg aacacccgaa atacaaagtt gctgttgttc aggctgctcc ggcttggctg     60
gacctggacg ttctgttgtga caaatctatc gctctgatca agaagctgc tgaaaaaggt    120 gctaaactga tcgctttccc ggaagctttc atcccgggtt accgtggca catctggatg    180 gactctccgg cttgggctat cggtcgtggt ttcgttcagc gttacttcga caactctctg    240
tcttacgact ctccgcaggc tgaacgtctg cgtgacgctg ttaaaaaagc taaactgacc    300
gctgttttcg gtctgtctga acgtgacggt ggttctctgt acctggctca gtggctgatc    360

```
ggtccggacg gtgaaaccat cgctaaacgt cgtaaactgc gtccgaccca cgctgaacgt    420
accgtttacg gtgaaggtga cggttctgac ctggctgttc acgctcgtgc tgacatcggt    480
cgtatcggtg ctctgtgctg ctgggaacac ctgcagccgc tgtctaaata cgctatgtac    540
gctcagaacg aacaggttca cgttgctgct tggccgtctt tctctctgta cgacccgttc    600
gctccggctc tgggtgctga agttaacaac gctgcttctc gtgtttacgc tgttgaaggt    660
tcttgcttcg ttctggctcc gtgcgctacc gtttctcagg ctatgatcga cgaactgtgc    720
gaccgtccgg acaaaaacgc tctgctgcac gttggtggtg gtttcgctgc tatctacggt    780
ccggacggtt ctcagatcgg tgacaaactg gctccggacc aggaaggtct gctgatcgct    840
gaaatcgacc tgggtgctat cggtgttgct aaaaacgctg ctgacccggc tggtcactac    900
tctcgtccgg acgttacccg tctgctgctg aacaaaaaac gttaccagcg tgttgaacag    960
ttcgctctgc cggttgacac cgttgaaccg gctgacatcg tgctgctgc ttct          1014
```

<210> SEQ ID NO 30
<211> LENGTH: 338
<212> TYPE: PRT
<213> ORGANISM: Unknown
<220> FEATURE:
<223> OTHER INFORMATION: Unknown prokaryotic organism

<400> SEQUENCE: 30

```
Met Gly Ile Glu His Pro Lys Tyr Lys Val Ala Val Gln Ala Ala
1               5                   10                  15

Pro Ala Trp Leu Asp Leu Asp Gly Ser Val Asp Lys Ser Ile Ala Leu
            20                  25                  30

Ile Lys Glu Ala Ala Glu Lys Gly Ala Lys Leu Ile Ala Phe Pro Glu
        35                  40                  45

Ala Phe Ile Pro Gly Tyr Pro Trp His Ile Trp Met Asp Ser Pro Ala
    50                  55                  60

Trp Ala Ile Gly Arg Gly Phe Val Gln Arg Tyr Phe Asp Asn Ser Leu
65                  70                  75                  80

Ser Tyr Asp Ser Pro Gln Ala Glu Arg Leu Arg Asp Ala Val Lys Lys
                85                  90                  95

Ala Lys Leu Thr Ala Val Phe Gly Leu Ser Glu Arg Asp Gly Gly Ser
            100                 105                 110

Leu Tyr Leu Ala Gln Trp Leu Ile Gly Pro Asp Gly Glu Thr Ile Ala
        115                 120                 125

Lys Arg Arg Lys Leu Arg Pro Thr His Ala Glu Arg Thr Val Tyr Gly
    130                 135                 140

Glu Gly Asp Gly Ser Asp Leu Ala Val His Ala Arg Ala Asp Ile Gly
145                 150                 155                 160

Arg Ile Gly Ala Leu Cys Cys Trp Glu His Leu Gln Pro Leu Ser Lys
                165                 170                 175

Tyr Ala Met Tyr Ala Gln Asn Glu Gln Val His Val Ala Ala Trp Pro
            180                 185                 190

Ser Phe Ser Leu Tyr Asp Pro Phe Ala Pro Leu Gly Ala Glu Val
        195                 200                 205

Asn Asn Ala Ala Ser Arg Val Tyr Ala Val Glu Gly Ser Cys Phe Val
    210                 215                 220

Leu Ala Pro Cys Ala Thr Val Ser Gln Ala Met Ile Asp Glu Leu Cys
225                 230                 235                 240

Asp Arg Pro Asp Lys Asn Ala Leu Leu His Val Gly Gly Gly Phe Ala
                245                 250                 255
```

Ala Ile Tyr Gly Pro Asp Gly Ser Gln Ile Gly Asp Lys Leu Ala Pro
            260                 265                 270

Asp Gln Glu Gly Leu Leu Ile Ala Glu Ile Asp Leu Gly Ala Ile Gly
                275                 280                 285

Val Ala Lys Asn Ala Ala Asp Pro Ala Gly His Tyr Ser Arg Pro Asp
290                 295                 300

Val Thr Arg Leu Leu Leu Asn Lys Lys Arg Tyr Gln Arg Val Glu Gln
305                 310                 315                 320

Phe Ala Leu Pro Val Asp Thr Val Glu Pro Ala Asp Ile Gly Ala Ala
                325                 330                 335

Ala Ser

<210> SEQ ID NO 31
<211> LENGTH: 1011
<212> TYPE: DNA
<213> ORGANISM: Unknown
<220> FEATURE:
<223> OTHER INFORMATION: Unknown prokaryotic organism

<400> SEQUENCE: 31
atgggtatca cccacccgaa ctacaaagtt gctgttgttc aggctgctcc ggtttggctg        60
aacctggaag ctaccgttga aaaaaccatc cgttacatcg aagaagctgc taaagctggt       120
gctaaactga tcgctttccc ggaaacctgg atcccgggtt accgtggca catctggatc        180 ggtaccccgg cttgggctat cggtaaaggt ttcgttcagc gttacttcga caactctctg       240
tcttacgact ctccgctggc tcgtcagatc gctgacgctg ctgctaaatc taaaatcacc       300
gttgttctgg gtctgtctga acgtgacggt ggttctctgt acatcgctca gtggctgatc       360
ggtccggacg gtgaaaccat cgctaaacgt cgtaaactgc gtccgaccca cgttgaacgt       420
accgttttcg gtgacggtga cggttctcac atcgctgttc acgaccgttc tgacctgggt       480
cgtctgggtg ctctgtgctg ctgggaacac gttcagccgc tgaccaaatt cgctatgtac       540
gctcagaacg aacaggttca cgttgctgct tggccgtctt ctctctatgta cgaaccgttc       600 gctcacgctc tgggttggga aaccaacaac gctgtttcta agtttacgc tgttgaaggt       660 tcttgcttcg ttctggctcc gtgcgctgtt atctctcagg ctatggttga cgaaatgtgc       720
gacaccccgg acaaacgtga actggttcac gctggtggtg gtcacgctgt tatctacggt       780
ccggacggtt ctccgctggc tgaaaaactg ggtgaaaacg aagaaggtct gctgtacgct       840
accgttaacc tggctgctat cggtgttgct aaaaacgctg ctgacccggc tggtcactac       900
tctcgtccgg acgttctgcg tctgctgttc aacaaatctc cggctcgtcg tgttgaacac       960
ttcgctctgc cgcacgaaca gctggaaatc ggtgctggtc cgtctggtga c                1011

<210> SEQ ID NO 32
<211> LENGTH: 337
<212> TYPE: PRT
<213> ORGANISM: Unknown
<220> FEATURE:
<223> OTHER INFORMATION: Unknown prokaryotic organism

<400> SEQUENCE: 32

Met Gly Ile Thr His Pro Asn Tyr Lys Val Ala Val Val Gln Ala Ala
1               5                   10                  15

Pro Val Trp Leu Asn Leu Glu Ala Thr Val Glu Lys Thr Ile Arg Tyr
                20                  25                  30

Ile Glu Glu Ala Ala Lys Ala Gly Ala Lys Leu Ile Ala Phe Pro Glu

```
                35                  40                  45
Thr Trp Ile Pro Gly Tyr Pro Trp His Ile Trp Ile Gly Thr Pro Ala
 50                  55                  60

Trp Ala Ile Gly Lys Gly Phe Val Gln Arg Tyr Phe Asp Asn Ser Leu
 65                  70                  75                  80

Ser Tyr Asp Ser Pro Leu Ala Arg Gln Ile Ala Asp Ala Ala Ala Lys
                 85                  90                  95

Ser Lys Ile Thr Val Val Leu Gly Leu Ser Glu Arg Asp Gly Gly Ser
            100                 105                 110

Leu Tyr Ile Ala Gln Trp Leu Ile Gly Pro Asp Gly Glu Thr Ile Ala
        115                 120                 125

Lys Arg Arg Lys Leu Arg Pro Thr His Val Glu Arg Thr Val Phe Gly
130                 135                 140

Asp Gly Asp Gly Ser His Ile Ala Val His Asp Arg Ser Asp Leu Gly
145                 150                 155                 160

Arg Leu Gly Ala Leu Cys Cys Trp Glu His Val Gln Pro Leu Thr Lys
                165                 170                 175

Phe Ala Met Tyr Ala Gln Asn Glu Gln Val His Val Ala Ala Trp Pro
            180                 185                 190

Ser Phe Ser Met Tyr Glu Pro Phe Ala His Ala Leu Gly Trp Glu Thr
        195                 200                 205

Asn Asn Ala Val Ser Lys Val Tyr Ala Val Gly Ser Cys Phe Val
210                 215                 220

Leu Ala Pro Cys Ala Val Ile Ser Gln Ala Met Val Asp Glu Met Cys
225                 230                 235                 240

Asp Thr Pro Asp Lys Arg Glu Leu Val His Ala Gly Gly His Ala
                245                 250                 255

Val Ile Tyr Gly Pro Asp Gly Ser Pro Leu Ala Glu Lys Leu Gly Glu
            260                 265                 270

Asn Glu Glu Gly Leu Leu Tyr Ala Thr Val Asn Leu Ala Ala Ile Gly
        275                 280                 285

Val Ala Lys Asn Ala Ala Asp Pro Ala Gly His Tyr Ser Arg Pro Asp
290                 295                 300

Val Leu Arg Leu Leu Phe Asn Lys Ser Pro Ala Arg Arg Val Glu His
305                 310                 315                 320

Phe Ala Leu Pro His Glu Gln Leu Glu Ile Gly Ala Gly Pro Ser Gly
                325                 330                 335

Asp

<210> SEQ ID NO 33
<211> LENGTH: 996
<212> TYPE: DNA
<213> ORGANISM: Synechococcus sp.
<220> FEATURE:
<223> OTHER INFORMATION: Synechococcus sp. CC9605

<400> SEQUENCE: 33
atgaccaccg ttaaagttgc tgctgctcag atccgtccgg ttctgttctc tctggacggt      60
tctctgcaga agttctgga cgctatggct gaagctgctg ctcagggtgt tgaactgatc     120
gttttcccgg aaaccttcct gccgtactac ccgtacttct ctttcgttga accgccggtt     180
ctgatgggtc gttctcacct ggctctgtac gaacaggctg ttgttgttcc gggtccggtt     240
accgacgctg ttgctgctgc tgcttctcag tacggtatgc aggttctgct gggtgttaac     300
gaacgtgacg gtggtaccct gtacaacacc cagctgctgt tcaactcttg cggtgaactg     360
```

-continued

```
gttctgaaac gtcgtaaaat caccccgacc taccacgaac gtatggtttg gggtcagggt    420
gacggttctg gtctgaaagt tgttcagacc ccgctggctc gtgttggtgc tctggcttgc    480
tgggaacact acaacccgct ggctcgttac gctctgatgg ctcagggtga agaaatccac    540
tgcgctcagt tcccgggttc tctggttggt ccgatcttca ccgaacagac cgctgttacc    600
atgcgtcacc acgctctgga agctggttgc ttcgttatct gctctaccgg ttggctgcac    660
ccggacgact acgcttctat cacctctgaa tctggtctgc acaaagcttt ccagggtggt    720
tgccacaccg ctgttatctc tccggaaggt cgttacctgg ctggtccgct gccggacggt    780
gaaggtctgg ctatcgctga cctggacctg gctctgatca ccaaacgtaa acgtatgatg    840
gactctgttg gtcactactc tcgtccggaa ctgctgtctc tgcagatcaa ctcttctccg    900
gctgttccgg ttcagaacat gtctaccgct tctgttccgc tggaaccggc taccgctacc    960
gacgctctgt cttctatgga agctctgaac cacgtt                              996
```

<210> SEQ ID NO 34
<211> LENGTH: 332
<212> TYPE: PRT
<213> ORGANISM: Synechococcus sp.
<220> FEATURE:
<223> OTHER INFORMATION: Synechococcus sp. CC9605

<400> SEQUENCE: 34

```
Met Thr Thr Val Lys Val Ala Ala Ala Gln Ile Arg Pro Val Leu Phe
 1               5                  10                  15

Ser Leu Asp Gly Ser Leu Gln Lys Val Leu Asp Ala Met Ala Glu Ala
            20                  25                  30

Ala Ala Gln Gly Val Glu Leu Ile Val Phe Pro Glu Thr Phe Leu Pro
        35                  40                  45

Tyr Tyr Pro Tyr Phe Ser Phe Val Glu Pro Pro Val Leu Met Gly Arg
    50                  55                  60

Ser His Leu Ala Leu Tyr Glu Gln Ala Val Val Pro Gly Pro Val
 65                  70                  75                  80

Thr Asp Ala Val Ala Ala Ala Ser Gln Tyr Gly Met Gln Val Leu
                85                  90                  95

Leu Gly Val Asn Glu Arg Asp Gly Gly Thr Leu Tyr Asn Thr Gln Leu
            100                 105                 110

Leu Phe Asn Ser Cys Gly Glu Leu Val Leu Lys Arg Lys Ile Thr
        115                 120                 125

Pro Thr Tyr His Glu Arg Met Val Trp Gly Gln Gly Asp Gly Ser Gly
    130                 135                 140

Leu Lys Val Val Gln Thr Pro Leu Ala Arg Val Gly Ala Leu Ala Cys
145                 150                 155                 160

Trp Glu His Tyr Asn Pro Leu Ala Arg Tyr Ala Leu Met Ala Gln Gly
                165                 170                 175

Glu Glu Ile His Cys Ala Gln Phe Pro Gly Ser Leu Val Gly Pro Ile
            180                 185                 190

Phe Thr Glu Gln Thr Ala Val Thr Met Arg His His Ala Leu Glu Ala
        195                 200                 205

Gly Cys Phe Val Ile Cys Ser Thr Gly Trp Leu His Pro Asp Asp Tyr
    210                 215                 220

Ala Ser Ile Thr Ser Glu Ser Gly Leu His Lys Ala Phe Gln Gly Gly
225                 230                 235                 240

Cys His Thr Ala Val Ile Ser Pro Glu Gly Arg Tyr Leu Ala Gly Pro
```

245                 250                 255

Leu Pro Asp Gly Glu Gly Leu Ala Ile Ala Asp Leu Asp Ala Leu
            260                 265                 270

Ile Thr Lys Arg Lys Arg Met Met Asp Ser Val Gly His Tyr Ser Arg
        275                 280                 285

Pro Glu Leu Leu Ser Leu Gln Ile Asn Ser Ser Pro Ala Val Pro Val
    290                 295                 300

Gln Asn Met Ser Thr Ala Ser Val Pro Leu Glu Pro Ala Thr Ala Thr
305                 310                 315                 320

Asp Ala Leu Ser Ser Met Glu Ala Leu Asn His Val
                325                 330

<210> SEQ ID NO 35

<400> SEQUENCE: 35

000

<210> SEQ ID NO 36

<400> SEQUENCE: 36

000

<210> SEQ ID NO 37
<211> LENGTH: 951
<212> TYPE: DNA
<213> ORGANISM: Aquimarina atlantica

<400> SEQUENCE: 37

```
atgaaagacc agctgctgac cgttgctctg gctcagatct ctccggtttg gctggacaaa      60
accgctacca tcaaaaaaat cgaaaactct atcgctgaag ctgcttctaa aaaagctgaa     120
ctgatcgttt tcggtgaatc tctgctgccg ggttacccgt tctgggtttc tctgaccgac     180
ggtgctaaat cgactctaa aatccagaaa gaaatccacg ctcactacgc tcagaactct     240
atcgttatcg aaaacggtga cctggacacc atctgcgaac tggctgctga atgcaacatc     300
gctatctacc tgggtatcat cgaacgtccg atcgaccgtg tggtcactc tctgtacgct     360
tctctggttt acatcgacca gaaaggtgaa atcaaatctg ttcaccgtaa actgcagccg     420
acctacgaag aacgtctgac ctgggctccg ggtgacggta acgtctgct ggttcacccg     480
ctgaaagctt tcaccgttgg tggtctgaac tgctgggaaa actggatgcc gctgccgcgt     540
gctgctctgt acggtcaggg tgaaaacctg cacatcgctg tttggccggg ttctgactac     600
aacaccaaag acatcacccg tttcatcgct cgtgaatctc gttcttacgt tatctctgtt     660
tcttctctga tgcgtaccga agacttcccg aaaaccaccc cgcacctgga cgaaatcctg     720
aaaaaagctc cggacgttct gggtaacggt ggttcttgca tcgctggtcc ggacggtgaa     780
tgggttatga aaccggttct gcacaaagaa ggtctgctga tcgaaaccct ggacttctct     840
aaagttctgc aggaacgtca gaacttcgac ccggttggtc actactctcg tccggacgtt     900
acccagctgc acgttaaccg taaacgtcag tctaccgttc gtttcgacga a                951
```

<210> SEQ ID NO 38
<211> LENGTH: 317
<212> TYPE: PRT
<213> ORGANISM: Aquimarina atlantica

<400> SEQUENCE: 38

```
Met Lys Asp Gln Leu Leu Thr Val Ala Leu Ala Gln Ile Ser Pro Val
1               5                   10                  15

Trp Leu Asp Lys Thr Ala Thr Ile Lys Lys Ile Glu Asn Ser Ile Ala
            20                  25                  30

Glu Ala Ala Ser Lys Lys Ala Glu Leu Ile Val Phe Gly Glu Ser Leu
        35                  40                  45

Leu Pro Gly Tyr Pro Phe Trp Val Ser Leu Thr Asp Gly Ala Lys Phe
    50                  55                  60

Asp Ser Lys Ile Gln Lys Glu Ile His Ala His Tyr Ala Gln Asn Ser
65                  70                  75                  80

Ile Val Ile Glu Asn Gly Asp Leu Asp Thr Ile Cys Glu Leu Ala Ala
                85                  90                  95

Glu Cys Asn Ile Ala Ile Tyr Leu Gly Ile Ile Glu Arg Pro Ile Asp
            100                 105                 110

Arg Gly Gly His Ser Leu Tyr Ala Ser Leu Val Tyr Ile Asp Gln Lys
        115                 120                 125

Gly Glu Ile Lys Ser Val His Arg Lys Leu Gln Pro Thr Tyr Glu Glu
    130                 135                 140

Arg Leu Thr Trp Ala Pro Gly Asp Gly Asn Gly Leu Leu Val His Pro
145                 150                 155                 160

Leu Lys Ala Phe Thr Val Gly Leu Asn Cys Trp Glu Asn Trp Met
                165                 170                 175

Pro Leu Pro Arg Ala Ala Leu Tyr Gly Gln Gly Glu Asn Leu His Ile
            180                 185                 190

Ala Val Trp Pro Gly Ser Asp Tyr Asn Thr Lys Asp Ile Thr Arg Phe
        195                 200                 205

Ile Ala Arg Glu Ser Arg Ser Tyr Val Ile Ser Val Ser Ser Leu Met
    210                 215                 220

Arg Thr Glu Asp Phe Pro Lys Thr Thr Pro His Leu Asp Glu Ile Leu
225                 230                 235                 240

Lys Lys Ala Pro Asp Val Leu Gly Asn Gly Gly Ser Cys Ile Ala Gly
                245                 250                 255

Pro Asp Gly Glu Trp Val Met Lys Pro Val Leu His Lys Glu Gly Leu
            260                 265                 270

Leu Ile Glu Thr Leu Asp Phe Ser Lys Val Leu Gln Glu Arg Gln Asn
        275                 280                 285

Phe Asp Pro Val Gly His Tyr Ser Arg Pro Asp Val Thr Gln Leu His
    290                 295                 300

Val Asn Arg Lys Arg Gln Ser Thr Val Arg Phe Asp Glu
305                 310                 315

<210> SEQ ID NO 39
<211> LENGTH: 945
<212> TYPE: DNA
<213> ORGANISM: Arthrobacter sp.
<220> FEATURE:
<223> OTHER INFORMATION: Arthrobacter sp. Soil736

<400> SEQUENCE: 39
atgcgtatcg ctgctatcca ggctaccccg gttatcctgg acgctgaagc ttctgtttct      60
aaagctctgc gtctgctggg tgaagctgct ggtcagggtg ttaaactggc tgttttcccg     120
gaaaccttca tcccgctgta cccgtctggt gtttgggctt accaggctgc tcgtttcgac     180
ggtttcgacg aaatgtggac cgtctgtggg acaactctg ttgacgttcc gggtccgcag     240
atcgaccgtt tcatcaaagc ttgcgctgaa cacgacatct actgcgttct gggtgttaac     300
```

```
gaacgtgaat ctgctcgtcc gggttctctg tacaacacca tgatcctgct gggtccggaa      360
ggtctgctgt ggaaacaccg taaactgatg ccgaccatgc acgaacgtct gttccacggt      420
gttggttacg tcaggacct  gaacgttatc gaaaccccgg ttggtcgtgt tggtggtctg      480
atctgctggg aaaaccgtat gccgctggct cgttacgctg tttaccgtca gggtgttcag      540
atctgggctg ctccgaccgc tgacgactct gacggttgga tctctaccat gtctcacatc      600
gctatcgaat ctggtgcttt cgttgtttct gctccgcagt acatcccgcg ttctgctttc      660
ccggacgact tcccggttca gctgccggac gacggtcagg ctctgggtcg tggtggtgct      720
gctatcttcg aaccgctgca gggtcgtgct atcgctggtc cgctgtacga ccaggaaggt      780
atcgttgttg ctgacgttga cctgggtcgt tctctgaccg ctaaacgtat cttcgacgtt      840
gttggtcact actctcgtga agacgttctg tacccgccgg ctccgaccaa ccacgctccg      900
gaaggtccgg ctttctggcc gcgtacccgt ccgctgctgg gtaac                     945
```

<210> SEQ ID NO 40
<211> LENGTH: 315
<212> TYPE: PRT
<213> ORGANISM: Arthrobacter sp.
<220> FEATURE:
<223> OTHER INFORMATION: Arthrobacter sp. Soil736

<400> SEQUENCE: 40

```
Met Arg Ile Ala Ala Ile Gln Ala Thr Pro Val Ile Leu Asp Ala Glu
1               5                   10                  15

Ala Ser Val Ser Lys Ala Leu Arg Leu Leu Gly Glu Ala Ala Gly Gln
            20                  25                  30

Gly Val Lys Leu Ala Val Phe Pro Glu Thr Phe Ile Pro Leu Tyr Pro
        35                  40                  45

Ser Gly Val Trp Ala Tyr Gln Ala Ala Arg Phe Asp Gly Phe Asp Glu
    50                  55                  60

Met Trp Thr Arg Leu Trp Asp Asn Ser Val Asp Val Pro Gly Pro Gln
65                  70                  75                  80

Ile Asp Arg Phe Ile Lys Ala Cys Ala Glu His Asp Ile Tyr Cys Val
                85                  90                  95

Leu Gly Val Asn Glu Arg Glu Ser Ala Arg Pro Gly Ser Leu Tyr Asn
            100                 105                 110

Thr Met Ile Leu Leu Gly Pro Glu Gly Leu Leu Trp Lys His Arg Lys
        115                 120                 125

Leu Met Pro Thr Met His Glu Arg Leu Phe His Gly Val Gly Tyr Gly
    130                 135                 140

Gln Asp Leu Asn Val Ile Glu Thr Pro Val Gly Arg Val Gly Gly Leu
145                 150                 155                 160

Ile Cys Trp Glu Asn Arg Met Pro Leu Ala Arg Tyr Ala Val Tyr Arg
                165                 170                 175

Gln Gly Val Gln Ile Trp Ala Ala Pro Thr Ala Asp Asp Ser Asp Gly
            180                 185                 190

Trp Ile Ser Thr Met Ser His Ile Ala Ile Glu Ser Gly Ala Phe Val
        195                 200                 205

Val Ser Ala Pro Gln Tyr Ile Pro Arg Ser Ala Phe Pro Asp Asp Phe
    210                 215                 220

Pro Val Gln Leu Pro Asp Asp Gly Gln Ala Leu Gly Arg Gly Gly Ala
225                 230                 235                 240

Ala Ile Phe Glu Pro Leu Gln Gly Arg Ala Ile Ala Gly Pro Leu Tyr
```

245                 250                 255
Asp Gln Glu Gly Ile Val Val Ala Asp Val Asp Leu Gly Arg Ser Leu
            260                 265                 270

Thr Ala Lys Arg Ile Phe Asp Val Val Gly His Tyr Ser Arg Glu Asp
        275                 280                 285

Val Leu Tyr Pro Pro Ala Pro Thr Asn His Ala Pro Glu Gly Pro Ala
    290                 295                 300

Phe Trp Pro Arg Thr Arg Pro Leu Leu Gly Asn
305                 310                 315

<210> SEQ ID NO 41
<211> LENGTH: 1020
<212> TYPE: DNA
<213> ORGANISM: Cupriavidus basilensis

<400> SEQUENCE: 41
atgtctcaga acgtatcgt tcgtgctgct gctgttcaga tctctccgga cctggaacac      60
ggtgaaggta ccctgggtaa agtttgcgaa gctatcgacc gtgctgctcg tgaaggtgtt     120
cagctgatcg ttttcccgga aaccttcctg ccgtactacc cgtacttctc tttcgttcgt     180
ccgccggttc agtctggttc tgaccacatg cgtctgtacg aacaggctgt tgttgttccg     240
ggtccggtta cccacgctgt ttctgaacgt gctcgtcgtc acgctatggt tgttgttctg     300
ggtgttaacg aacgtgacca cggttctctg tacaacaccc agctgatctt cgacaccgac     360
ggtcgtctgg ttctgaaacg tcgtaaaatc accccgacct ccacgaacg tatgatctgg     420
ggtcagggtg acgctgctgg tctgaaagtt gctgacaccg ctatcggtcg tgttggtgct     480
ctggcttgct gggaacacta caacccgctg gctcgttacg ctctgatgac ccagcacgaa     540
gaaatccact gctctcagtt cccgggttct ctggttggtc ggttttcgc tgaacagatc     600
gaagttacca tccgtcacca cgctctggaa tctggttgct cgttgttaa cgctaccggt     660
tggctgaccg acgaacagat cgcttctgtt accaccgacc cggctctgca gaaagctctg     720
cgtggtggtt gcaacaccgc tatcgtttct ccggaaggtc agcacctggc tccgccgctg     780
cgtgaaggtg aaggtatggt tatcgctgac ctggacatgt ctctgatcac caaacgtaaa     840
cgtatgatgg actctgttgg tcactacgct cgtccggaac tgctgtctct ggctatcaac     900
gaccgtccgg ctgctaccgc ttctccgatg gctaccgctc tgtctaacta ccacggttct     960
acccaccacg aaccgcagcg tgacgacgct ggtctggacc tggaaccggt tgttggtaac    1020

<210> SEQ ID NO 42
<211> LENGTH: 340
<212> TYPE: PRT
<213> ORGANISM: Cupriavidus basilensis

<400> SEQUENCE: 42

Met Ser Gln Lys Arg Ile Val Arg Ala Ala Ala Val Gln Ile Ser Pro
1               5                   10                  15

Asp Leu Glu His Gly Glu Gly Thr Leu Gly Lys Val Cys Glu Ala Ile
            20                  25                  30

Asp Arg Ala Ala Arg Glu Gly Val Gln Leu Ile Val Phe Pro Glu Thr
        35                  40                  45

Phe Leu Pro Tyr Tyr Pro Tyr Phe Ser Phe Val Arg Pro Pro Val Gln
    50                  55                  60

Ser Gly Ser Asp His Met Arg Leu Tyr Glu Gln Ala Val Val Val Pro
65                  70                  75                  80

Gly Pro Val Thr His Ala Val Ser Glu Arg Ala Arg Arg His Ala Met
            85                  90                  95

Val Val Val Leu Gly Val Asn Glu Arg Asp His Gly Ser Leu Tyr Asn
        100                 105                 110

Thr Gln Leu Ile Phe Asp Thr Asp Gly Arg Leu Val Leu Lys Arg Arg
        115                 120                 125

Lys Ile Thr Pro Thr Phe His Glu Arg Met Ile Trp Gly Gln Gly Asp
130                 135                 140

Ala Ala Gly Leu Lys Val Ala Asp Thr Ala Ile Gly Arg Val Gly Ala
145                 150                 155                 160

Leu Ala Cys Trp Glu His Tyr Asn Pro Leu Ala Arg Tyr Ala Leu Met
                165                 170                 175

Thr Gln His Glu Glu Ile His Cys Ser Gln Phe Pro Gly Ser Leu Val
        180                 185                 190

Gly Pro Val Phe Ala Glu Gln Ile Glu Val Thr Ile Arg His His Ala
        195                 200                 205

Leu Glu Ser Gly Cys Phe Val Val Asn Ala Thr Gly Trp Leu Thr Asp
    210                 215                 220

Glu Gln Ile Ala Ser Val Thr Thr Asp Pro Ala Leu Gln Lys Ala Leu
225                 230                 235                 240

Arg Gly Gly Cys Asn Thr Ala Ile Val Ser Pro Gly Gln His Leu
                245                 250                 255

Ala Pro Pro Leu Arg Glu Gly Glu Gly Met Val Ile Ala Asp Leu Asp
                260                 265                 270

Met Ser Leu Ile Thr Lys Arg Lys Arg Met Met Asp Ser Val Gly His
        275                 280                 285

Tyr Ala Arg Pro Glu Leu Leu Ser Leu Ala Ile Asn Asp Arg Pro Ala
        290                 295                 300

Ala Thr Ala Ser Pro Met Ala Thr Ala Leu Ser Asn Tyr His Gly Ser
305                 310                 315                 320

Thr His His Glu Pro Gln Arg Asp Asp Ala Gly Leu Asp Leu Glu Pro
                325                 330                 335

Val Val Gly Asn
        340

<210> SEQ ID NO 43

<400> SEQUENCE: 43

000

<210> SEQ ID NO 44

<400> SEQUENCE: 44

000

<210> SEQ ID NO 45
<211> LENGTH: 1059
<212> TYPE: DNA
<213> ORGANISM: Sphingomonas wittichii
<220> FEATURE:
<223> OTHER INFORMATION: Sphingomonas wittichii RW1

<400> SEQUENCE: 45
atgaacgaag gtttccagaa agttcgtgtt gctgctgctc agatctctcc ggctttcctg     60
gaccgtgaag ttctaccga aatcgcttgc cactggatcg ctgaagctgc tcgtggtggt    120

```
gctgaactgc tgtctttcgg tgaagcttgg ctgccggctt acccgttctg gatcttcatg      180
ggttctccga tctactctgc tcagttctct cgtcgtctgt acgaaaacgc tgttgaaatc      240
ccgtctgcta ccaccgaccg tctgtgcgaa gctgctcgta aagctggtat ccacgttgtt      300
atgggtctga ccgaactgtg gggtggttct ctgtacctgg ctcagctgtt catcaacgac      360
cgtggtgaaa tcgttggtca ccgtcgtaaa ctgaaaccga cccactggga acgtgctatc      420
tggggtgaag gtgacggttc tgacttcttc gttgttccga cctctatcgg tcgtctgggt      480
gctctgaact gctgggaaca cctgcagccg ctgaacctgt tcgctatgaa cgctttcggt      540
gaacagatcc acgttgctgc ttggccggct ttcgctatct acaaccgtgt tgacccgtct      600
ttcaccaacg aagctaacct ggctgcttct cgtgcttacg ctatggctac ccagaccttc      660
gttatccaca cctctgctgt tgttgacgac gctaccgttg aactgctgtg cgacgacgac      720
gacaaacgtc tgctgctgga atctggtggt ggtcagtgcg ctgttatcaa cccgctgggt      780
gctatcatct ctaccccgct gtcttctacc gctcagggtc tggttttcgc tgactgcgac      840
ttcggtgtta tcgcttctgc taaaatgtct aacgacccgg ctggtcacta ccagcgtggt      900
gacgttttcc aggttcactt caacccggct ccgcgtcgtc cgctggttcc gcgtgctgct      960
atcgctgctg acccgaccac cgctgcttct gaagacctgc cgaacatcaa acacccgccg     1020
ttctctccgg ctgttaaact gccgatcgtt gttgacgac                           1059

<210> SEQ ID NO 46
<211> LENGTH: 353
<212> TYPE: PRT
<213> ORGANISM: Sphingomonas wittichii
<220> FEATURE:
<223> OTHER INFORMATION: Sphingomonas wittichii RW1

<400> SEQUENCE: 46

Met Asn Glu Gly Phe Gln Lys Val Arg Val Ala Ala Gln Ile Ser
1               5                   10                  15

Pro Ala Phe Leu Asp Arg Glu Gly Ser Thr Glu Ile Ala Cys His Trp
            20                  25                  30

Ile Ala Glu Ala Ala Arg Gly Gly Ala Glu Leu Leu Ser Phe Gly Glu
        35                  40                  45

Ala Trp Leu Pro Ala Tyr Pro Phe Trp Ile Phe Met Gly Ser Pro Ile
    50                  55                  60

Tyr Ser Ala Gln Phe Ser Arg Arg Leu Tyr Glu Asn Ala Val Glu Ile
65                  70                  75                  80

Pro Ser Ala Thr Thr Asp Arg Leu Cys Glu Ala Ala Arg Lys Ala Gly
                85                  90                  95

Ile His Val Val Met Gly Leu Thr Glu Leu Trp Gly Gly Ser Leu Tyr
            100                 105                 110

Leu Ala Gln Leu Phe Ile Asn Asp Arg Gly Glu Ile Val Gly His Arg
        115                 120                 125

Arg Lys Leu Lys Pro Thr His Trp Glu Arg Ala Ile Trp Gly Glu Gly
    130                 135                 140

Asp Gly Ser Asp Phe Phe Val Val Pro Thr Ser Ile Gly Arg Leu Gly
145                 150                 155                 160

Ala Leu Asn Cys Trp Glu His Leu Gln Pro Leu Asn Leu Phe Ala Met
                165                 170                 175

Asn Ala Phe Gly Glu Gln Ile His Val Ala Ala Trp Pro Ala Phe Ala
            180                 185                 190

Ile Tyr Asn Arg Val Asp Pro Ser Phe Thr Asn Glu Ala Asn Leu Ala
```

```
                195                 200                 205
Ala Ser Arg Ala Tyr Ala Met Ala Thr Gln Thr Phe Val Ile His Thr
    210                 215                 220

Ser Ala Val Val Asp Asp Ala Thr Val Glu Leu Leu Cys Asp Asp Asp
225                 230                 235                 240

Asp Lys Arg Leu Leu Leu Glu Ser Gly Gly Gln Cys Ala Val Ile
                245                 250                 255

Asn Pro Leu Gly Ala Ile Ile Ser Thr Pro Leu Ser Ser Thr Ala Gln
            260                 265                 270

Gly Leu Val Phe Ala Asp Cys Asp Phe Gly Val Ile Ala Ser Ala Lys
        275                 280                 285

Met Ser Asn Asp Pro Ala Gly His Tyr Gln Arg Gly Asp Val Phe Gln
    290                 295                 300

Val His Phe Asn Pro Ala Pro Arg Arg Pro Leu Val Pro Arg Ala Ala
305                 310                 315                 320

Ile Ala Ala Asp Pro Thr Thr Ala Ala Ser Glu Asp Leu Pro Asn Ile
                325                 330                 335

Lys His Pro Pro Phe Ser Pro Ala Val Lys Leu Pro Ile Val Val Asp
            340                 345                 350

Asp
```

```
<210> SEQ ID NO 47
<211> LENGTH: 951
<212> TYPE: DNA
<213> ORGANISM: Pseudomonas mandelii
<220> FEATURE:
<223> OTHER INFORMATION: Pseudomonas mandelii JR-1

<400> SEQUENCE: 47
atggaaaacg ctatgaccaa agttgctatc atccagcgtc cgccggttct gctggaccgt    60
tctgctacca tcgctcgtgc tgttcagtct gttgctgaag ctgctgctgc tggtgcttct   120
ctgatcgttc tgccggaatc tttcatcccg ggttacccgt cttggatctg cgtctggct   180
gctggtaaag acggtgctgt tatgggtcag ctgcacaccc gtctgctggc taacgctgtt   240
gacatcgcta acggtgacct gggtgaactg tgcgaagctg tcgtgttca cgctgttacc   300
atcgtttgcg gtatcaacga atgcgaccgt tctaccggtg tggtaccct gtacaactct   360
gttgttgtta tcggtgctga cggtgctgtt ctgaaccgtc accgtaaact gatgccgacc   420
aacccggaac gtatggttca cggtttcggt gacgcttctg gtctgcgtgc tgttgacacc   480
ccggttggtc gtgttggtgc tctgatctgc tgggaaaact acatgccgct ggctcgttac   540
tctctgtacg ctcagggtgt tgaaatctac atcgctccga cctacgacac cggtgaaggt   600
tggatctcta ccatgcgtca catcgctctg gaaggtcgtt gctgggttct gggttctggt   660
accgctctgc gtggttctga catcccggaa gacttcccgg ctcgtatgca gctgttcgct   720
gacccggacg aatggatcaa cgacggtgac tctgttgttg tttctccgca gggtcgtgtt   780
gttgctggtc cgctgcaccg tgaagctggt atcctgtacg ctgacatcga cgttgctctg   840
gttgctccgg ctcgtcgtgc tctggacgtt accggtcact cgctcgtcc ggacatcttc   900
gaactgcacg ttcgtcgttc tccggctatc ccggttcact acatcgacga a            951

<210> SEQ ID NO 48
<211> LENGTH: 317
<212> TYPE: PRT
<213> ORGANISM: Pseudomonas mandelii
<220> FEATURE:
```

<223> OTHER INFORMATION: Pseudomonas mandelii JR-1

<400> SEQUENCE: 48

```
Met Glu Asn Ala Met Thr Lys Val Ala Ile Ile Gln Arg Pro Pro Val
1               5                   10                  15

Leu Leu Asp Arg Ser Ala Thr Ile Ala Arg Ala Val Gln Ser Val Ala
                20                  25                  30

Glu Ala Ala Ala Gly Ala Ser Leu Ile Val Leu Pro Glu Ser Phe
            35                  40                  45

Ile Pro Gly Tyr Pro Ser Trp Ile Trp Arg Leu Ala Ala Gly Lys Asp
        50                  55                  60

Gly Ala Val Met Gly Gln Leu His Thr Arg Leu Leu Ala Asn Ala Val
65                  70                  75                  80

Asp Ile Ala Asn Gly Asp Leu Gly Glu Leu Cys Glu Ala Ala Arg Val
                85                  90                  95

His Ala Val Thr Ile Val Cys Gly Ile Asn Glu Cys Asp Arg Ser Thr
                100                 105                 110

Gly Gly Gly Thr Leu Tyr Asn Ser Val Val Ile Gly Ala Asp Gly
            115                 120                 125

Ala Val Leu Asn Arg His Arg Lys Leu Met Pro Thr Asn Pro Glu Arg
        130                 135                 140

Met Val His Gly Phe Gly Asp Ala Ser Gly Leu Arg Ala Val Asp Thr
145                 150                 155                 160

Pro Val Gly Arg Val Gly Ala Leu Ile Cys Trp Glu Asn Tyr Met Pro
                165                 170                 175

Leu Ala Arg Tyr Ser Leu Tyr Ala Gln Gly Val Glu Ile Tyr Ile Ala
                180                 185                 190

Pro Thr Tyr Asp Thr Gly Glu Gly Trp Ile Ser Thr Met Arg His Ile
            195                 200                 205

Ala Leu Glu Gly Arg Cys Trp Val Leu Gly Ser Gly Thr Ala Leu Arg
        210                 215                 220

Gly Ser Asp Ile Pro Glu Asp Phe Pro Ala Arg Met Gln Leu Phe Ala
225                 230                 235                 240

Asp Pro Asp Glu Trp Ile Asn Asp Gly Asp Ser Val Val Val Ser Pro
                245                 250                 255

Gln Gly Arg Val Val Ala Gly Pro Leu His Arg Glu Ala Gly Ile Leu
            260                 265                 270

Tyr Ala Asp Ile Asp Val Ala Leu Val Ala Pro Ala Arg Arg Ala Leu
        275                 280                 285

Asp Val Thr Gly His Tyr Ala Arg Pro Asp Ile Phe Glu Leu His Val
        290                 295                 300

Arg Arg Ser Pro Ala Ile Pro Val His Tyr Ile Asp Glu
305                 310                 315
```

<210> SEQ ID NO 49

<400> SEQUENCE: 49

000

<210> SEQ ID NO 50

<400> SEQUENCE: 50

000

<210> SEQ ID NO 51
<211> LENGTH: 1017
<212> TYPE: DNA
<213> ORGANISM: Arabidopsis thaliana

<400> SEQUENCE: 51

```
atgtctacct ctgaaaacac cccgttcaac ggtgttgctt cttctaccat cgttcgtgct      60
accatcgttc aggcttctac cgtttacaac gacaccccgg ctaccctgga aaaagctaac     120
aaattcatcg ttgaagctgc ttctaaaggt tctgaactgg ttgttttccc ggaagctttc     180
atcggtggtt acccgcgtgg tttccgtttc ggtctgggtg ttggtgttca acgaagaa       240
ggtcgtgacg aattccgtaa ataccacgct tctgctatca agttccgggt ccggaagtt      300
gaaaaactgg ctgaactggc tggtaaaaac aacgtttacc tggttatggg tgctatcgaa     360
aaagacggtt acaccctgta ctgcaccgct ctgttcttct ctccgcaggg tcagttcctg     420
ggtaaacacc gtaaactgat gccgacctct ctggaacgtt gcatctgggg tcagggtgac     480
ggttctacca tcccggttta cgacaccccg atcggtaaac tgggtgctgc tatctgctgg     540
gaaaaccgta tgccgctgta ccgtaccgct ctgtacgcta aaggtatcga actgtactgc     600
gctccgaccg ctgacggttc taagaatgg cagtcttcta tgctgcacat cgctatcgaa      660
ggtggttgct tcgttctgtc tgcttgccag ttctgcctgc gtaaagactt cccggaccac     720
ccggactacc tgttcaccga ctggtacgac gacaaagaac cggactctat cgtttctcag     780
ggtggttctg ttatcatctc tccgctgggt caggttctgg ctggtccgaa cttcgaatct     840
gaaggtctga tcaccgctga cctggacctg ggtgacgttg ctcgtgctaa actgtacttc     900
gactctgttg gtcactactc tcgtccggac gttctgcacc tgaccgttaa cgaacacccg     960
aaaaaaccgg ttaccttcat ctctaaagtt gaaaaagctg aagacgactc taacaaa       1017
```

<210> SEQ ID NO 52
<211> LENGTH: 339
<212> TYPE: PRT
<213> ORGANISM: Arabidopsis thaliana

<400> SEQUENCE: 52

```
Met Ser Thr Ser Glu Asn Thr Pro Phe Asn Gly Val Ala Ser Ser Thr
1               5                   10                  15

Ile Val Arg Ala Thr Ile Val Gln Ala Ser Thr Val Tyr Asn Asp Thr
            20                  25                  30

Pro Ala Thr Leu Glu Lys Ala Asn Lys Phe Ile Val Glu Ala Ala Ser
        35                  40                  45

Lys Gly Ser Glu Leu Val Val Phe Pro Glu Ala Phe Ile Gly Gly Tyr
    50                  55                  60

Pro Arg Gly Phe Arg Phe Gly Leu Gly Val Gly Val His Asn Glu Glu
65                  70                  75                  80

Gly Arg Asp Glu Phe Arg Lys Tyr His Ala Ser Ala Ile Lys Val Pro
                85                  90                  95

Gly Pro Glu Val Glu Lys Leu Ala Glu Leu Ala Gly Lys Asn Asn Val
            100                 105                 110

Tyr Leu Val Met Gly Ala Ile Glu Lys Asp Gly Tyr Thr Leu Tyr Cys
        115                 120                 125

Thr Ala Leu Phe Phe Ser Pro Gln Gly Gln Phe Leu Gly Lys His Arg
    130                 135                 140

Lys Leu Met Pro Thr Ser Leu Glu Arg Cys Ile Trp Gly Gln Gly Asp
145                 150                 155                 160
```

```
Gly Ser Thr Ile Pro Val Tyr Asp Thr Pro Ile Gly Lys Leu Gly Ala
            165                 170                 175
Ala Ile Cys Trp Glu Asn Arg Met Pro Leu Tyr Arg Thr Ala Leu Tyr
        180                 185                 190
Ala Lys Gly Ile Glu Leu Tyr Cys Ala Pro Thr Ala Asp Gly Ser Lys
    195                 200                 205
Glu Trp Gln Ser Ser Met Leu His Ile Ala Ile Glu Gly Gly Cys Phe
210                 215                 220
Val Leu Ser Ala Cys Gln Phe Cys Leu Arg Lys Asp Phe Pro Asp His
225                 230                 235                 240
Pro Asp Tyr Leu Phe Thr Asp Trp Tyr Asp Asp Lys Glu Pro Asp Ser
            245                 250                 255
Ile Val Ser Gln Gly Gly Ser Val Ile Ile Ser Pro Leu Gly Gln Val
        260                 265                 270
Leu Ala Gly Pro Asn Phe Glu Ser Glu Gly Leu Ile Thr Ala Asp Leu
    275                 280                 285
Asp Leu Gly Asp Val Ala Arg Ala Lys Leu Tyr Phe Asp Ser Val Gly
290                 295                 300
His Tyr Ser Arg Pro Asp Val Leu His Leu Thr Val Asn Glu His Pro
305                 310                 315                 320
Lys Lys Pro Val Thr Phe Ile Ser Lys Val Glu Lys Ala Glu Asp Asp
            325                 330                 335
Ser Asn Lys

<210> SEQ ID NO 53
<211> LENGTH: 1029
<212> TYPE: DNA
<213> ORGANISM: Brassica oleracea

<400> SEQUENCE: 53
atgtctaccc cgaaaaacac cacccaggct aacggtgact cttcttcttc tatcgttcgt      60
gctaccatcg ttcaggcttc taccgtttac aacgacaccc cgaaaaccat cgaaaaagct     120
gaaaaactga tcgctgaagc tgcttctaac ggttctgaac tggttgtttt cccggaaggt     180
ttcatcggtg gttacccgcg tggtttccgt ttcggtatcg ctgttggtat ccacaacgaa     240
gacggtcgtg acgacttccg taaataccac gactctgcta ccacgttcc  gggtccggaa     300
gttgacaaac tggctgaact ggctcgtaaa acaacgtttt acctggttat gggtgctatc     360
gaaaaagacg ttacaccct gtactgcacc gctctgttct tcaactctga aggtcgttac     420
ctgggtaaac accgtaaagt tatgccgacc tctctggaac gttgcatctg gggtttcggt     480
gacggttcta ccatcccggt ttacgacacc ccgatcggta aactgggtgc tgctatctgc     540
tgggaaaacc gtatgccgct gtaccgtacc gctctgtacg ctaaaggtgt tgaactgtac     600
tgcgctccga ccgctgacgg ttctaaagaa tggcagtctt ctatgatgca catcgctatg     660
gaaggtggtt gcttcgttct gtctgcttgc cagttctgcc agcgtaaaga cttcccggct     720
cacgttgacc acctgttcac cgactggtac gacgaccagc acgacgaagc tatcgtttct     780
cagggtggtt ctgttatcat ctctccgctg ggtaaagttc tggctggtcc gaacttcgaa     840
tctgaaggtc tgatcaccgc tgacctggac ctgggtgaca tcgctcgtgc taaactgtac     900
ttcgacgttg ttggtcacta ctctaaaccg gacgttttca acctgaccgt taacgaacac     960
ccgaaaaaac cggttacctt cgtttctaaa accgttaaag ctgaagacgg ttctgaatct    1020
aaagaaaaa                                                             1029
```

<210> SEQ ID NO 54
<211> LENGTH: 343
<212> TYPE: PRT
<213> ORGANISM: Brassica oleracea

<400> SEQUENCE: 54

Met Ser Thr Pro Lys Asn Thr Thr Gln Ala Asn Gly Asp Ser Ser Ser
1               5                   10                  15

Ser Ile Val Arg Ala Thr Ile Val Gln Ala Ser Thr Val Tyr Asn Asp
            20                  25                  30

Thr Pro Lys Thr Ile Glu Lys Ala Glu Lys Leu Ile Ala Glu Ala Ala
        35                  40                  45

Ser Asn Gly Ser Glu Leu Val Val Phe Pro Glu Gly Phe Ile Gly Gly
    50                  55                  60

Tyr Pro Arg Gly Phe Arg Phe Gly Ile Ala Val Gly Ile His Asn Glu
65                  70                  75                  80

Asp Gly Arg Asp Asp Phe Arg Lys Tyr His Asp Ser Ala Ile His Val
                85                  90                  95

Pro Gly Pro Glu Val Asp Lys Leu Ala Glu Leu Ala Arg Lys Asn Asn
            100                 105                 110

Val Tyr Leu Val Met Gly Ala Ile Glu Lys Asp Gly Tyr Thr Leu Tyr
        115                 120                 125

Cys Thr Ala Leu Phe Phe Asn Ser Glu Gly Arg Tyr Leu Gly Lys His
    130                 135                 140

Arg Lys Val Met Pro Thr Ser Leu Glu Arg Cys Ile Trp Gly Phe Gly
145                 150                 155                 160

Asp Gly Ser Thr Ile Pro Val Tyr Asp Thr Pro Ile Gly Lys Leu Gly
                165                 170                 175

Ala Ala Ile Cys Trp Glu Asn Arg Met Pro Leu Tyr Arg Thr Ala Leu
            180                 185                 190

Tyr Gly Lys Gly Val Glu Leu Tyr Cys Ala Pro Thr Ala Asp Gly Ser
        195                 200                 205

Lys Glu Trp Gln Ser Ser Met Met His Ile Ala Met Glu Gly Gly Cys
    210                 215                 220

Phe Val Leu Ser Ala Cys Gln Phe Cys Gln Arg Lys Asp Phe Pro Ala
225                 230                 235                 240

His Val Asp His Leu Phe Thr Asp Trp Tyr Asp Asp Gln His Asp Glu
                245                 250                 255

Ala Ile Val Ser Gln Gly Gly Ser Val Ile Ser Pro Leu Gly Lys
            260                 265                 270

Val Leu Ala Gly Pro Asn Phe Glu Ser Glu Gly Leu Ile Thr Ala Asp
        275                 280                 285

Leu Asp Leu Gly Asp Ile Ala Arg Ala Lys Leu Tyr Phe Asp Val Val
    290                 295                 300

Gly His Tyr Ser Lys Pro Asp Val Phe Asn Leu Thr Val Asn Glu His
305                 310                 315                 320

Pro Lys Lys Pro Val Thr Phe Val Ser Lys Thr Val Lys Ala Glu Asp
                325                 330                 335

Gly Ser Glu Ser Lys Glu Lys
            340

<210> SEQ ID NO 55
<211> LENGTH: 1035
<212> TYPE: DNA
<213> ORGANISM: Salinisphaera shabanensis
<220> FEATURE:
<223> OTHER INFORMATION: Salinisphaera shabanensis E1L3A

<400> SEQUENCE: 55

```
atgacccagt ctcagatcgt taaagttgct gctgttcagc tgcagccggt tctggactct      60
gctgacggta ccgttgaacg tgttctggac gaaatcgctg ctgctgctgc tgacggtgct     120
cagctggttg ttttcccgga aaccgctgtt ccgtactacc cgtactggtc tttcgttatg     180
gctccgatgg acatgggtgc tcgtcaccgt gctctgtacg accactctcc gaccgttccg     240
ggtccggtta ccgacgctgt tgctgctgct gctcgtaccc acgaaatcgt tgttgttctg     300
ggtgttaacg aacgtgacca cggtaccctg tacaactgcc agctggtttt cgacggtaac     360
ggtgaaatcg ctctgaaacg tcgtaaaatc accccgacct accacgaacg tatggtttgg     420
ggtcagggtg acggttctgg tctgcacgct gttgacaccg ctgttggtcg tgttggtgct     480
ctggcttgct gggaacacta caacccgctg gctcgttacg ctctgatggc tgaccacgaa     540
cagatccact gctctcagtt cccgggttct ctggttggtc gatcttcgc tgaacagcag      600
gaagttaccc tgcgtcacca cgctctggaa tctggttgct tcgttgttaa cgctaccgct     660
tggctggacg ctgaccaggt tgcttctgtt accgaagacc cggctctgca gaaaggtctg     720
ttcggtggtt gctacaccgc tatcatcgct ccggacggtt ctcacgttgt tgctccgctg     780
ctggacggtc cgggtcgtct ggttgctgac atcgacctgt ctctgatcac caaacgtaaa     840
cgtatgatgg actctgttgg tcactacgct cgtccggaac tgctgtctct gcgtatcgac     900
cgtcgttctc acgctgctca gcacgctgac gctgctccgg tgttggtgc tgtttctgaa      960
ttcgaagaac cggaccacgg tgaaccggaa ccgtacgctg cttaccgtga cgctatcgct    1020
cgttcttcta ccggt                                                    1035
```

<210> SEQ ID NO 56
<211> LENGTH: 345
<212> TYPE: PRT
<213> ORGANISM: Salinisphaera shabanensis
<220> FEATURE:
<223> OTHER INFORMATION: Salinisphaera shabanensis E1L3A

<400> SEQUENCE: 56

```
Met Thr Gln Ser Gln Ile Val Lys Val Ala Ala Val Gln Leu Gln Pro
1               5                   10                  15

Val Leu Asp Ser Ala Asp Gly Thr Val Glu Arg Val Leu Asp Glu Ile
                20                  25                  30

Ala Ala Ala Ala Ala Asp Gly Ala Gln Leu Val Val Phe Pro Glu Thr
            35                  40                  45

Ala Val Pro Tyr Tyr Pro Tyr Trp Ser Phe Val Met Ala Pro Met Asp
        50                  55                  60

Met Gly Ala Arg His Arg Ala Leu Tyr Asp His Ser Pro Thr Val Pro
65                  70                  75                  80

Gly Pro Val Thr Asp Ala Val Ala Ala Ala Arg Thr His Glu Ile
                85                  90                  95

Val Val Val Leu Gly Val Asn Glu Arg Asp His Gly Thr Leu Tyr Asn
                100                 105                 110

Cys Gln Leu Val Phe Asp Gly Asn Gly Glu Ile Ala Leu Lys Arg Arg
            115                 120                 125

Lys Ile Thr Pro Thr Tyr His Glu Arg Met Val Trp Gly Gln Gly Asp
        130                 135                 140

Gly Ser Gly Leu His Ala Val Asp Thr Ala Val Gly Arg Val Gly Ala
```

```
                145                 150                 155                 160
            Leu Ala Cys Trp Glu His Tyr Asn Pro Leu Ala Arg Tyr Ala Leu Met
                        165                 170                 175
            Ala Asp His Glu Gln Ile His Cys Ser Gln Phe Pro Gly Ser Leu Val
                        180                 185                 190
            Gly Pro Ile Phe Ala Glu Gln Glu Val Thr Leu Arg His His Ala
                        195                 200                 205
            Leu Glu Ser Gly Cys Phe Val Val Asn Ala Thr Ala Trp Leu Asp Ala
                210                 215                 220
            Asp Gln Val Ala Ser Val Thr Glu Asp Pro Ala Leu Gln Lys Gly Leu
            225                 230                 235                 240
            Phe Gly Gly Cys Tyr Thr Ala Ile Ile Ala Pro Asp Gly Ser His Val
                        245                 250                 255
            Val Ala Pro Leu Leu Asp Gly Pro Gly Arg Leu Val Ala Asp Ile Asp
                        260                 265                 270
            Leu Ser Leu Ile Thr Lys Arg Lys Arg Met Met Asp Ser Val Gly His
                        275                 280                 285
            Tyr Ala Arg Pro Glu Leu Leu Ser Leu Arg Ile Asp Arg Arg Ser His
                        290                 295                 300
            Ala Ala Gln His Ala Asp Ala Ala Pro Gly Val Gly Ala Val Ser Glu
            305                 310                 315                 320
            Phe Glu Glu Pro Asp His Gly Glu Pro Glu Pro Tyr Ala Ala Tyr Arg
                        325                 330                 335
            Asp Ala Ile Ala Arg Ser Ser Thr Gly
                        340                 345

<210> SEQ ID NO 57

<400> SEQUENCE: 57

000

<210> SEQ ID NO 58

<400> SEQUENCE: 58

000

<210> SEQ ID NO 59
<211> LENGTH: 954
<212> TYPE: DNA
<213> ORGANISM: Smithella sp.
<220> FEATURE:
<223> OTHER INFORMATION: Smithella sp. SDB

<400> SEQUENCE: 59
atgaaaaacc agaccaaagt tgctgctatc cagctggcta ccaaaatcgg tgactctaac      60
accaacatcg ctggttgcga acgtctggct ctgatggcta tcaaaaacgg tgctcgttgg     120
atcgctctgc cggaattctt caccaccggt gtttcttgga accggaaat cgcttcttct     180 atccagaccg ttgacggtgc tgctgcttct ttcatgtgcg acttctctgc taaacaccag     240
gttgttctgg gtggttcttt cctgtgccgt ctgtctgacg ttctgttcg taaccgttac     300 cagtgctacg ctaacggttc tctgatcggt cagcacgaca agacctgcc gaccatgtgg     360 gaaaactact ctacgaagg tggtgacccg atggactctg tgttctggg tacctacaac     420 aacatccgta tcggtgctgc tgtttgctgg gaattcatgc gtaccatgac cgctcgtcgt     480
ctgcgtaaca aagttgacgt tatcatcggt ggttcttgct ggtggtctat cccgaccaac     540
```

```
ttcccggttt tcctgcagaa actgtgggaa ccggctaacc actactgctc tctggctgct    600
atccaggact ctgctcgtct gatcggtgct ccggttatcc acgctgctca ctgcggtgaa    660
atcgaatgcc cgatgccggg tctgccgatc aaataccgtg gttacttcga aggtaacgct    720
tctatcgttg acgcttctgg taaagttctg gctcagcgtt ctgctgaaca gggtgaaggt    780
atcgtttgcg ctgacatcct gctggaagct cagccgacca tcgaagctat cccggaccgt    840
ttctggctgc gttctcgtgg tttcctgccg accttcgctt ggcaccacca gcgttggctg    900
ggtcgtcgtt ggtacaaacg taacgttcgt cagaaaaaaa acgaactgca ccac          954
```

<210> SEQ ID NO 60
<211> LENGTH: 318
<212> TYPE: PRT
<213> ORGANISM: Smithella sp.
<220> FEATURE:
<223> OTHER INFORMATION: Smithella sp. SDB

<400> SEQUENCE: 60

```
Met Lys Asn Gln Thr Lys Val Ala Ala Ile Gln Leu Ala Thr Lys Ile
1               5                   10                  15

Gly Asp Ser Asn Thr Asn Ile Ala Gly Cys Glu Arg Leu Ala Leu Met
            20                  25                  30

Ala Ile Lys Asn Gly Ala Arg Trp Ile Ala Leu Pro Glu Phe Phe Thr
        35                  40                  45

Thr Gly Val Ser Trp Lys Pro Glu Ile Ala Ser Ser Ile Gln Thr Val
    50                  55                  60

Asp Gly Ala Ala Ala Ser Phe Met Cys Asp Phe Ser Ala Lys His Gln
65                  70                  75                  80

Val Val Leu Gly Gly Ser Phe Leu Cys Arg Leu Ser Asp Gly Ser Val
                85                  90                  95

Arg Asn Arg Tyr Gln Cys Tyr Ala Asn Gly Ser Leu Ile Gly Gln His
            100                 105                 110

Asp Lys Asp Leu Pro Thr Met Trp Glu Asn Tyr Phe Tyr Glu Gly Gly
        115                 120                 125

Asp Pro Met Asp Ser Gly Val Leu Gly Thr Tyr Asn Asn Ile Arg Ile
    130                 135                 140

Gly Ala Ala Val Cys Trp Glu Phe Met Arg Thr Met Thr Ala Arg Arg
145                 150                 155                 160

Leu Arg Asn Lys Val Asp Val Ile Ile Gly Gly Ser Cys Trp Trp Ser
                165                 170                 175

Ile Pro Thr Asn Phe Pro Val Phe Leu Gln Lys Leu Trp Glu Pro Ala
            180                 185                 190

Asn His Tyr Cys Ser Leu Ala Ala Ile Gln Asp Ser Ala Arg Leu Ile
        195                 200                 205

Gly Ala Pro Val Ile His Ala Ala His Cys Gly Glu Ile Glu Cys Pro
    210                 215                 220

Met Pro Gly Leu Pro Ile Lys Tyr Arg Gly Tyr Phe Glu Gly Asn Ala
225                 230                 235                 240

Ser Ile Val Asp Ala Ser Gly Lys Val Leu Ala Gln Arg Ser Ala Glu
                245                 250                 255

Gln Gly Glu Gly Ile Val Cys Ala Asp Ile Leu Leu Glu Ala Gln Pro
            260                 265                 270

Thr Ile Glu Ala Ile Pro Asp Arg Phe Trp Leu Arg Ser Arg Gly Phe
        275                 280                 285
```

Leu Pro Thr Phe Ala Trp His His Gln Arg Trp Leu Gly Arg Arg Trp
        290                 295                 300

Tyr Lys Arg Asn Val Arg Gln Lys Lys Asn Glu Leu His His
305                 310                 315

<210> SEQ ID NO 61
<211> LENGTH: 963
<212> TYPE: DNA
<213> ORGANISM: Bradyrhizobium diazoefficiens

<400> SEQUENCE: 61

| | | | | | |
|---|---|---|---|---|---|
| atgatggata | gtaaccgccc | gaatacctat | aaagcagccg | tggtgcaggc | agccagcgat | 60 |
| ccgaccagca | gcctggttag | tgcacagaaa | gccgcagccc | tgattgaaaa | agccgccggt | 120 |
| gcaggtgcac | gtctggttgt | gtttccggaa | gcctttattg | gtggttatcc | gaaaggtaat | 180 |
| agctttggtg | ccccggtggg | catgcgtaaa | ccggaaggtc | gtgaagcatt | tcgtctgtat | 240 |
| tgggaagcag | caattgatct | ggatggcgtt | gaagtggaaa | ccattgccgc | agcagcagca | 300 |
| gcgaccggtg | cctttaccgt | tattggctgt | attgaacgtg | aacagggcac | cctgtattgc | 360 |
| accgcactgt | ttttcgatgg | cgcccgtggt | ctggttggta | acatcgtaa | actgatgccg | 420 |
| accgccggcg | aacgcctgat | tggggctttt | ggtgacggta | gcaccatgcc | ggtgtttgaa | 480 |
| accagtctgg | gtaatattgg | cgcagttatt | tgctgggaaa | attatatgcc | gatgctgcgc | 540 |
| atgcacatgt | atagtcaggg | cattagtatc | tattgtgccc | cgaccgcaga | tgatcgtgat | 600 |
| acctggctgc | cgaccatgca | gcatattgca | ctggaaggcc | gctgctttgt | tctgaccgcc | 660 |
| tgccagcatc | tgaaacgtgg | cgcatttccg | gccgattatg | aatgcgcact | gggcgcagat | 720 |
| ccggaaaccg | tgctgatgcg | cggtggtagt | gcaattgtga | atccgctggg | taaagttctg | 780 |
| gccgccccgt | gctttgaagg | cgaaaccatt | ctgtatgcag | atattgcact | ggatgaagtt | 840 |
| acccgtggta | aatttgattt | tgatgcagca | ggccattata | gtcgtccgga | tgtgtttcag | 900 |
| ctggttgtgg | atgatcgtcc | gaaacgcgcc | gttagcaccg | tgagcgccgt | gcgtgcccgc | 960 |
| aat | | | | | | 963 |

<210> SEQ ID NO 62
<211> LENGTH: 321
<212> TYPE: PRT
<213> ORGANISM: Bradyrhizobium diazoefficiens

<400> SEQUENCE: 62

Met Met Asp Ser Asn Arg Pro Asn Thr Tyr Lys Ala Ala Val Val Gln
1               5                   10                  15

Ala Ala Ser Asp Pro Thr Ser Ser Leu Val Ser Ala Gln Lys Ala Ala
            20                  25                  30

Ala Leu Ile Glu Lys Ala Ala Gly Ala Gly Ala Arg Leu Val Val Phe
        35                  40                  45

Pro Glu Ala Phe Ile Gly Gly Tyr Pro Lys Gly Asn Ser Phe Gly Ala
    50                  55                  60

Pro Val Gly Met Arg Lys Pro Glu Gly Arg Glu Ala Phe Arg Leu Tyr
65                  70                  75                  80

Trp Glu Ala Ala Ile Asp Leu Asp Gly Val Glu Val Glu Thr Ile Ala
                85                  90                  95

Ala Ala Ala Ala Ala Thr Gly Ala Phe Thr Val Ile Gly Cys Ile Glu
            100                 105                 110

Arg Glu Gln Gly Thr Leu Tyr Cys Thr Ala Leu Phe Phe Asp Gly Ala
        115                 120                 125

Arg Gly Leu Val Gly Lys His Arg Lys Leu Met Pro Thr Ala Gly Glu
130                 135                 140

Arg Leu Ile Trp Gly Phe Gly Asp Gly Ser Thr Met Pro Val Phe Glu
145                 150                 155                 160

Thr Ser Leu Gly Asn Ile Gly Ala Val Ile Cys Trp Glu Asn Tyr Met
                165                 170                 175

Pro Met Leu Arg Met His Met Tyr Ser Gln Gly Ile Ser Ile Tyr Cys
                180                 185                 190

Ala Pro Thr Ala Asp Asp Arg Asp Thr Trp Leu Pro Thr Met Gln His
                195                 200                 205

Ile Ala Leu Glu Gly Arg Cys Phe Val Leu Thr Ala Cys Gln His Leu
                210                 215                 220

Lys Arg Gly Ala Phe Pro Ala Asp Tyr Glu Cys Ala Leu Gly Ala Asp
225                 230                 235                 240

Pro Glu Thr Val Leu Met Arg Gly Gly Ser Ala Ile Val Asn Pro Leu
                245                 250                 255

Gly Lys Val Leu Ala Gly Pro Cys Phe Glu Gly Glu Thr Ile Leu Tyr
                260                 265                 270

Ala Asp Ile Ala Leu Asp Glu Val Thr Arg Gly Lys Phe Asp Phe Asp
                275                 280                 285

Ala Ala Gly His Tyr Ser Arg Pro Asp Val Phe Gln Leu Val Val Asp
                290                 295                 300

Asp Arg Pro Lys Arg Ala Val Ser Thr Val Ser Ala Val Arg Ala Arg
305                 310                 315                 320

Asn

<210> SEQ ID NO 63
<211> LENGTH: 933
<212> TYPE: DNA
<213> ORGANISM: Actinobacteria bacterium
<220> FEATURE:
<223> OTHER INFORMATION: Actinobacteria bacterium RBG_13_55_18

<400> SEQUENCE: 63

```
atgaaagttg ctgctgttca gatcaaagct aaactggctt gcgttgaaga aaacctggaa    60
cgtgctgaaa aactgctgga caaagctttc ggtcagggtt gcgaaatggt tatcctgccg   120
gaattcttca cctctgctgt tgcttttcca ccggacatgc tgaccgctgc tctgccgttc   180
gaaggtccgg ctctgggtct gctgcgtgac gctgctaaac gttacggtgg ttacgctggt   240
ggttctttca tcgcttctcg tgaaggtaac aactacaaca ccttcgttct ggctttcccg   300
gacggtggtt acgttaccca caacaaagac cagccgacca tgtgggaaaa ctgctactac   360
atcggtggta cgacgaagg tatcatggaa accccgctgg tccggttgg ttctgctctg   420
tgctgggaaa tggttcgtac ccgtaccgtt cgtcgtctgc gtggtcgtat cggtctggct   480
gttggtggtt cttgctggtg gacgttccg gaccgtctgc tgccgctgcc gggtaaaaaa   540
tctgctaaac gtcgtaacct ggctatcatg aacgaaaccc cggttcgtct ggctaaaatg   600
ctgggtgttc cggttgttca cgctgctcac gctgaagctt cgaatgccg tatgccgctg   660
gttccgggta tcccgtaccg ttctcacttc ctgggtgaca ccatgatcgt tgacgctgac   720
ggttctgttc tggctcaccg ttctcgtgaa gaaggtgaag gtctggctat cgctgacgtt   780
cgtgttggtg gtatcgaacc gtctgaagac ccgccggacc gtttctggat cccggaactg   840
ccgctgctga tccgtttcgc ttgggcttac cagaacctgc acggtcgtct gtactaccgt   900
```
cgtgctctgc gtaccggtcg tatccagatc aaa                                         933

<210> SEQ ID NO 64
<211> LENGTH: 311
<212> TYPE: PRT
<213> ORGANISM: Actinobacteria bacterium
<220> FEATURE:
<223> OTHER INFORMATION: Actinobacteria bacterium RBG_13_55_18

<400> SEQUENCE: 64

```
Met Lys Val Ala Ala Val Gln Ile Lys Ala Lys Leu Ala Cys Val Glu
1               5                   10                  15

Glu Asn Leu Glu Arg Ala Glu Lys Leu Leu Asp Lys Ala Phe Gly Gln
            20                  25                  30

Gly Cys Glu Met Val Ile Leu Pro Glu Phe Phe Thr Ser Ala Val Ala
        35                  40                  45

Phe His Pro Asp Met Leu Thr Ala Ala Leu Pro Phe Glu Gly Pro Ala
    50                  55                  60

Leu Gly Leu Leu Arg Asp Ala Ala Lys Arg Tyr Gly Gly Tyr Ala Gly
65                  70                  75                  80

Gly Ser Phe Ile Ala Ser Arg Glu Gly Asn Asn Tyr Asn Thr Phe Val
                85                  90                  95

Leu Ala Phe Pro Asp Gly Gly Tyr Val Thr His Asn Lys Asp Gln Pro
            100                 105                 110

Thr Met Trp Glu Asn Cys Tyr Tyr Ile Gly Gly Asn Asp Glu Gly Ile
        115                 120                 125

Met Glu Thr Pro Leu Gly Pro Val Gly Ser Ala Leu Cys Trp Glu Met
    130                 135                 140

Val Arg Thr Arg Thr Val Arg Arg Leu Arg Gly Arg Ile Gly Leu Ala
145                 150                 155                 160

Val Gly Gly Ser Cys Trp Trp Asp Val Pro Asp Arg Leu Leu Pro Leu
                165                 170                 175

Pro Gly Lys Lys Ser Ala Lys Arg Arg Asn Leu Ala Ile Met Asn Glu
            180                 185                 190

Thr Pro Val Arg Leu Ala Lys Met Leu Gly Val Pro Val Val His Ala
        195                 200                 205

Ala His Ala Glu Ala Phe Glu Cys Arg Met Pro Leu Val Pro Gly Ile
    210                 215                 220

Pro Tyr Arg Ser His Phe Leu Gly Asp Thr Met Ile Val Asp Ala Asp
225                 230                 235                 240

Gly Ser Val Leu Ala His Arg Ser Arg Glu Glu Gly Glu Gly Leu Ala
                245                 250                 255

Ile Ala Asp Val Arg Val Gly Gly Ile Glu Pro Ser Glu Asp Pro Pro
            260                 265                 270

Asp Arg Phe Trp Ile Pro Glu Leu Pro Leu Leu Ile Arg Phe Ala Trp
        275                 280                 285

Ala Tyr Gln Asn Leu His Gly Arg Leu Tyr Tyr Arg Arg Ala Leu Arg
    290                 295                 300

Thr Gly Arg Ile Gln Ile Lys
305                 310
```

<210> SEQ ID NO 65
<211> LENGTH: 1062
<212> TYPE: DNA
<213> ORGANISM: Rhizobium sp.
<220> FEATURE:
<223> OTHER INFORMATION: Rhizobium sp. YK2

<400> SEQUENCE: 65

```
atggaaaaca aatctatcgt tcgtgctgct gctgttcaga tcgctccgga cctgacctct      60
cgtgaaaaaa ccctggctcg tgttctggaa gctatccacg aagctgctgg taaaggtgct     120
gaactggctg ttttcccgga aaccttcgtt ccgtggtacc cgtacttctc tttcgttctg     180
ccgccggttc tgtctggtaa agaacacgtt cgtctgtacg acgaagctgt accgttccg      240
tctgctgcta ccgaagctat cgctaccgct gctcgtaacc acggtatcgt tgttgttctg     300
ggtgttaacg aacgtgacca cggttctctg tacaacaccc agctggtttt caacgctgac     360
ggtaccctga tcctgaaacg tcgtaaaatc accccgacct ccacgaacg tatgatctgg      420
ggtcagggtg acgcttctgg tctgaccgtt gttgaatctc acgttggtcg tatcggtgct     480
ctggcttgct gggaacacta caacccgctg gtctcgttacg ctctgatggc tcagcacgaa    540
gaaatccacg ttgctcagtt cccgggttct atggttggtc cgatcttcgc tgaacagatc     600
gaagttacca ccgtcacca cgctctggaa tctggttgct cgttgttaa cgctaccggt       660
tggctgaccg acgaacagat cgcttctatc accccggacc agaacctgca gaaagctctg     720
cgtggtggtt gcatgaccgc tatcatctct ccggaaggta acacctggc tccgccgctg      780
accgaaggtg aaggtatcct gatcgctgac ctggacatgt ctctgatcac caaacgtaaa    840
cgtatgatgg actctgttgg tcactacgct cgtccggaac tgctgcacct ggttatcgac     900
ggtcgtgcta ccgctccgat ggttgcttct gaatcttctt cgaaaaccg taacccgtct    960
cagaccgctt ctccgcgttc taactctgac ggtcaccacg acaacgcttc ttctgaccgt    1020
gacccggacc agcgtgttgc tgttctgcgt tctcaggctt ct                       1062
```

<210> SEQ ID NO 66
<211> LENGTH: 354
<212> TYPE: PRT
<213> ORGANISM: Rhizobium sp.
<220> FEATURE:
<223> OTHER INFORMATION: Rhizobium sp. YK2

<400> SEQUENCE: 66

```
Met Glu Asn Lys Ser Ile Val Arg Ala Ala Val Gln Ile Ala Pro
1               5                   10                  15

Asp Leu Thr Ser Arg Glu Lys Thr Leu Ala Arg Val Leu Glu Ala Ile
            20                  25                  30

His Glu Ala Ala Gly Lys Gly Ala Glu Leu Ala Val Phe Pro Glu Thr
        35                  40                  45

Phe Val Pro Trp Tyr Pro Tyr Phe Ser Phe Val Pro Pro Val Leu
    50                  55                  60

Ser Gly Lys Glu His Val Arg Leu Tyr Asp Glu Ala Val Thr Val Pro
65                  70                  75                  80

Ser Ala Ala Thr Glu Ala Ile Ala Thr Ala Ala Arg Asn His Gly Ile
                85                  90                  95

Val Val Val Leu Gly Val Asn Glu Arg Asp His Gly Ser Leu Tyr Asn
                100                 105                 110

Thr Gln Leu Val Phe Asn Ala Asp Gly Thr Leu Ile Leu Lys Arg Arg
            115                 120                 125

Lys Ile Thr Pro Thr Phe His Glu Arg Met Ile Trp Gly Gln Gly Asp
        130                 135                 140

Ala Ser Gly Leu Thr Val Val Glu Ser His Val Gly Arg Ile Gly Ala
145                 150                 155                 160
```

```
Leu Ala Cys Trp Glu His Tyr Asn Pro Leu Ala Arg Tyr Ala Leu Met
            165                 170                 175
Ala Gln His Glu Glu Ile His Val Ala Gln Phe Pro Gly Ser Met Val
        180                 185                 190
Gly Pro Ile Phe Ala Glu Gln Ile Glu Val Thr Ile Arg His His Ala
    195                 200                 205
Leu Glu Ser Gly Cys Phe Val Val Asn Ala Thr Gly Trp Leu Thr Asp
    210                 215                 220
Glu Gln Ile Ala Ser Ile Thr Pro Asp Gln Asn Leu Gln Lys Ala Leu
225                 230                 235                 240
Arg Gly Gly Cys Met Thr Ala Ile Ile Ser Pro Glu Gly Lys His Leu
                245                 250                 255
Ala Pro Pro Leu Thr Glu Gly Glu Gly Ile Leu Ile Ala Asp Leu Asp
            260                 265                 270
Met Ser Leu Ile Thr Lys Arg Lys Arg Met Met Asp Ser Val Gly His
        275                 280                 285
Tyr Ala Arg Pro Glu Leu Leu His Leu Val Ile Asp Gly Arg Ala Thr
    290                 295                 300
Ala Pro Met Val Ala Ser Glu Ser Ser Phe Glu Asn Arg Asn Pro Ser
305                 310                 315                 320
Gln Thr Ala Ser Pro Arg Ser Asn Ser Asp Gly His His Asp Asn Ala
                325                 330                 335
Ser Ser Asp Arg Asp Pro Asp Gln Arg Val Ala Val Leu Arg Ser Gln
            340                 345                 350
Ala Ser

<210> SEQ ID NO 67
<211> LENGTH: 951
<212> TYPE: DNA
<213> ORGANISM: bacterium YEK0313

<400> SEQUENCE: 67
atgtctgttg ttcgttacaa agctgctgtt gctcaggctg cttcttgccc ggacgacgct      60
atggcttctg ctaccaaagc tgctcgtctg atcgaagaag ctgctggtgc tggtgctcgt     120
ctgatcgttt tcccggaagc tttcctgggt ggttacccga aggtgcttc tttcggtgct     180
ccgatcggta tgcgtaaacc ggaaggtcgt gacgctttcc gtcactactt cgaacaggct     240
atcgacctgg acggtccgga agttgctgct atcgctgctg ctaccgctac caccggtctg     300
ttcgctgtta tcggttgcat cgaacgtgac ggtggtaccc tgcactgcac cgttctgttc     360
ttcgacggtg ctgctggtct ggttggtaaa caccgtaaac tgatgccgac cgctggtgaa     420
cgtctgatct ggggtttcgg tgacggttct accatgccgg ttttcaaaac ctctctgggt     480
cgtatcggtg ctgttatctg ctgggaaaac tacatgccga tgctgcgtat gcacatgttc     540
tctcagggta tctctatcta ctgcgctccg accgctgacg accgtgacac ctggctgccg     600
tctatgcgtc acatcgctct ggaaggtcgt tgcttcgttc tgaccgcttg ccagcacatc     660
cgtcgtggtg ctttcccggc tggtcacgaa tgcgctctgg gtgacgaccc ggacaccgtt     720
ctgatgcgtg tggttctgc tatcgttgac ccgctgggtg tgttctggc tggtccggac     780
ttcaccggtg aaaccatcct gtacgctgac atcgacctgg gtgaagttgc tcgtggtaaa     840
ttcgacttcg acgttgttgg tcactacgct cgtccggaca tcttctctct gaccgttgac     900
gaccgtccgc gtccggctgt ttctaccctg ggtgacccgc aggctggttc t              951
```

<210> SEQ ID NO 68
<211> LENGTH: 317
<212> TYPE: PRT
<213> ORGANISM: bacterium YEK0313

<400> SEQUENCE: 68

| Met | Ser | Val | Val | Arg | Tyr | Lys | Ala | Ala | Val | Ala | Gln | Ala | Ala | Ser | Cys |
|---|---|---|---|---|---|---|---|---|---|---|---|---|---|---|---|
| 1 | | | | 5 | | | | | 10 | | | | | 15 | |

| Pro | Asp | Asp | Ala | Met | Ala | Ser | Ala | Thr | Lys | Ala | Ala | Arg | Leu | Ile | Glu |
|---|---|---|---|---|---|---|---|---|---|---|---|---|---|---|---|
| | | | 20 | | | | | 25 | | | | | 30 | | |

| Glu | Ala | Ala | Gly | Ala | Gly | Ala | Arg | Leu | Ile | Val | Phe | Pro | Glu | Ala | Phe |
|---|---|---|---|---|---|---|---|---|---|---|---|---|---|---|---|
| | | 35 | | | | | 40 | | | | | 45 | | | |

| Leu | Gly | Gly | Tyr | Pro | Lys | Gly | Ala | Ser | Phe | Gly | Ala | Pro | Ile | Gly | Met |
|---|---|---|---|---|---|---|---|---|---|---|---|---|---|---|---|
| | 50 | | | | | 55 | | | | | 60 | | | | |

| Arg | Lys | Pro | Glu | Gly | Arg | Asp | Ala | Phe | Arg | His | Tyr | Phe | Glu | Gln | Ala |
|---|---|---|---|---|---|---|---|---|---|---|---|---|---|---|---|
| 65 | | | | | 70 | | | | | 75 | | | | | 80 |

| Ile | Asp | Leu | Asp | Gly | Pro | Glu | Val | Ala | Ala | Ile | Ala | Ala | Ala | Thr | Ala |
|---|---|---|---|---|---|---|---|---|---|---|---|---|---|---|---|
| | | | | 85 | | | | | 90 | | | | | 95 | |

| Thr | Thr | Gly | Leu | Phe | Ala | Val | Ile | Gly | Cys | Ile | Glu | Arg | Asp | Gly | Gly |
|---|---|---|---|---|---|---|---|---|---|---|---|---|---|---|---|
| | | | 100 | | | | | 105 | | | | | 110 | | |

| Thr | Leu | His | Cys | Thr | Val | Leu | Phe | Phe | Asp | Gly | Ala | Ala | Gly | Leu | Val |
|---|---|---|---|---|---|---|---|---|---|---|---|---|---|---|---|
| | | 115 | | | | | 120 | | | | | 125 | | | |

| Gly | Lys | His | Arg | Lys | Leu | Met | Pro | Thr | Ala | Gly | Glu | Arg | Leu | Ile | Trp |
|---|---|---|---|---|---|---|---|---|---|---|---|---|---|---|---|
| | 130 | | | | | 135 | | | | | 140 | | | | |

| Gly | Phe | Gly | Asp | Gly | Ser | Thr | Met | Pro | Val | Phe | Lys | Thr | Ser | Leu | Gly |
|---|---|---|---|---|---|---|---|---|---|---|---|---|---|---|---|
| 145 | | | | | 150 | | | | | 155 | | | | | 160 |

| Arg | Ile | Gly | Ala | Val | Ile | Cys | Trp | Glu | Asn | Tyr | Met | Pro | Met | Leu | Arg |
|---|---|---|---|---|---|---|---|---|---|---|---|---|---|---|---|
| | | | | 165 | | | | | 170 | | | | | 175 | |

| Met | His | Met | Phe | Ser | Gln | Gly | Ile | Ser | Ile | Tyr | Cys | Ala | Pro | Thr | Ala |
|---|---|---|---|---|---|---|---|---|---|---|---|---|---|---|---|
| | | | 180 | | | | | 185 | | | | | 190 | | |

| Asp | Asp | Arg | Asp | Thr | Trp | Leu | Pro | Ser | Met | Arg | His | Ile | Ala | Leu | Glu |
|---|---|---|---|---|---|---|---|---|---|---|---|---|---|---|---|
| | | 195 | | | | | 200 | | | | | 205 | | | |

| Gly | Arg | Cys | Phe | Val | Leu | Thr | Ala | Cys | Gln | His | Ile | Arg | Arg | Gly | Ala |
|---|---|---|---|---|---|---|---|---|---|---|---|---|---|---|---|
| | 210 | | | | | 215 | | | | | 220 | | | | |

| Phe | Pro | Ala | Gly | His | Glu | Cys | Ala | Leu | Gly | Asp | Asp | Pro | Asp | Thr | Val |
|---|---|---|---|---|---|---|---|---|---|---|---|---|---|---|---|
| 225 | | | | | 230 | | | | | 235 | | | | | 240 |

| Leu | Met | Arg | Gly | Gly | Ser | Ala | Ile | Val | Asp | Pro | Leu | Gly | Gly | Val | Leu |
|---|---|---|---|---|---|---|---|---|---|---|---|---|---|---|---|
| | | | | 245 | | | | | 250 | | | | | 255 | |

| Ala | Gly | Pro | Asp | Phe | Thr | Gly | Glu | Thr | Ile | Leu | Tyr | Ala | Asp | Ile | Asp |
|---|---|---|---|---|---|---|---|---|---|---|---|---|---|---|---|
| | | | 260 | | | | | 265 | | | | | 270 | | |

| Leu | Gly | Glu | Val | Ala | Arg | Gly | Lys | Phe | Asp | Phe | Asp | Val | Val | Gly | His |
|---|---|---|---|---|---|---|---|---|---|---|---|---|---|---|---|
| | | 275 | | | | | 280 | | | | | 285 | | | |

| Tyr | Ala | Arg | Pro | Asp | Ile | Phe | Ser | Leu | Thr | Val | Asp | Asp | Arg | Pro | Arg |
|---|---|---|---|---|---|---|---|---|---|---|---|---|---|---|---|
| | 290 | | | | | 295 | | | | | 300 | | | | |

| Pro | Ala | Val | Ser | Thr | Leu | Gly | Asp | Pro | Gln | Ala | Gly | Ser |
|---|---|---|---|---|---|---|---|---|---|---|---|---|
| 305 | | | | | 310 | | | | | 315 | | |

<210> SEQ ID NO 69
<211> LENGTH: 819
<212> TYPE: DNA
<213> ORGANISM: Paenibacillus darwinianus

<400> SEQUENCE: 69

```
atgatccgtg aaggtaaccg tctgaccgtt gctgctgttc agatgaactg cgttctgggt    60
gacgttgaag ctaacctgcg taaagctgaa cgtctgctgg aaatcgctgc tggtcgtggt   120
```

-continued

```
gctcgtctgg ctgttctgcc ggaactgttc aacaccggtt accgtgttga agaacgtgac    180
gttgaactgg ctgaaccgat cccgggtccg accaccgaat ggatgcgtcg tcaggcttct    240
aaacacggta tgaaactggt tgctgctatc ctggaaaaag gtgctccggc tggtctggtt    300
tacgacaccg ctgttctggt tgaaccggct ggtgttatcg gttcttaccg taaaacccac    360
ctgtggaacc aggaaaacac ccgtttcacc cgtggtgaac agttcccggt ttacgaaacc    420
gacggtatcc aggttggtct gcagatctgc tacgaaatcg gtttcccgga aggtgctcgt    480
atcctgacct tccacggtgc tgacatcatc gtttacccgt ctgctttcgg taaagctcgt    540
ctgtacgctt gggacatcgc tacccgttct cgtgctctgg aaaacggtac cttcgttatc    600
gcttctaacc gtaccggtct ggaaaaaggt gaaaccgaat cggtggtac ctctcgtatc    660 gttgacccgg ctggtaccat cctggctgaa gctgaacagg aagacgacgt tatcaccgct    720
gaactggacc tgggtctgat cgctgaacag cgtcgtgcta cccgtacct gcgtgacttc    780 aaccgttctc tgatctctaa agaatacaac tctgaacgt                           819
```

```
<210> SEQ ID NO 70
<211> LENGTH: 273
<212> TYPE: PRT
<213> ORGANISM: Paenibacillus darwinianus

<400> SEQUENCE: 70
```

| | | | | | | | | | | | | | | |
|---|---|---|---|---|---|---|---|---|---|---|---|---|---|---|
|Met|Ile|Arg|Glu|Gly|Asn|Arg|Leu|Thr|Val|Ala|Ala|Val|Gln|Met|Asn|
|1| | | |5| | | | |10| | | | |15| |
|Cys|Val|Leu|Gly|Asp|Val|Glu|Ala|Asn|Leu|Arg|Lys|Ala|Glu|Arg|Leu|
| | | |20| | | | |25| | | | |30| | |
|Leu|Glu|Ile|Ala|Ala|Gly|Arg|Gly|Ala|Arg|Leu|Ala|Val|Leu|Pro|Glu|
| | | | |35| | | | |40| | | | |45| |
|Leu|Phe|Asn|Thr|Gly|Tyr|Arg|Val|Glu|Glu|Arg|Asp|Val|Glu|Leu|Ala|
| |50| | | | |55| | | | |60| | | | |
|Glu|Pro|Ile|Pro|Gly|Pro|Thr|Thr|Glu|Trp|Met|Arg|Arg|Gln|Ala|Ser|
|65| | | | |70| | | | |75| | | | |80|
|Lys|His|Gly|Met|Lys|Leu|Val|Ala|Ala|Ile|Leu|Glu|Lys|Gly|Ala|Pro|
| | | | |85| | | | |90| | | | |95| |
|Ala|Gly|Leu|Val|Tyr|Asp|Thr|Ala|Val|Leu|Val|Glu|Pro|Ala|Gly|Val|
| | | |100| | | | |105| | | | |110| | |
|Ile|Gly|Ser|Tyr|Arg|Lys|Thr|His|Leu|Trp|Asn|Gln|Glu|Asn|Thr|Arg|
| | | | |115| | | | |120| | | | |125| |
|Phe|Thr|Arg|Gly|Glu|Gln|Phe|Pro|Val|Tyr|Glu|Thr|Asp|Gly|Ile|Gln|
| |130| | | | |135| | | | |140| | | | |
|Val|Gly|Leu|Gln|Ile|Cys|Tyr|Glu|Ile|Gly|Phe|Pro|Glu|Gly|Ala|Arg|
|145| | | | |150| | | | |155| | | | |160|
|Ile|Leu|Thr|Phe|His|Gly|Ala|Asp|Ile|Ile|Val|Tyr|Pro|Ser|Ala|Phe|
| | | | |165| | | | |170| | | | |175| |
|Gly|Lys|Ala|Arg|Leu|Tyr|Ala|Trp|Asp|Ile|Ala|Thr|Arg|Ser|Arg|Ala|
| | | |180| | | | |185| | | | |190| | |
|Leu|Glu|Asn|Gly|Thr|Phe|Val|Ile|Ala|Ser|Asn|Arg|Thr|Gly|Leu|Glu|
| | | | |195| | | | |200| | | | |205| |
|Lys|Gly|Glu|Thr|Glu|Phe|Gly|Gly|Thr|Ser|Arg|Ile|Val|Asp|Pro|Ala|
| |210| | | | |215| | | | |220| | | | |
|Gly|Thr|Ile|Leu|Ala|Glu|Ala|Glu|Gln|Glu|Asp|Asp|Val|Ile|Thr|Ala|
|225| | | | |230| | | | |235| | | | |240|
|Glu|Leu|Asp|Leu|Gly|Leu|Ile|Ala|Glu|Gln|Arg|Arg|Ala|Ile|Pro|Tyr|
| | | | |245| | | | |250| | | | |255| |

Leu Arg Asp Phe Asn Arg Ser Leu Ile Ser Lys Glu Tyr Asn Ser Glu
             260                 265                 270

Arg

<210> SEQ ID NO 71
<211> LENGTH: 1098
<212> TYPE: DNA
<213> ORGANISM: Haloarcula sp.
<220> FEATURE:
<223> OTHER INFORMATION: Haloarcula sp. CBA1115

<400> SEQUENCE: 71

| | |
|---|---|
| atgccggctg aatctttcac cctggctgct gctcaggttg aaccggttta ccacgacaaa | 60 |
| gaaggtaccc tggacaaaac ctgccgttac atcgaacagg ctggtcgtga cggtgctgac | 120 |
| atcgttgttt tcccggaaac ctacttcccg ggttacccgt actggcgtgg ttctgtttct | 180 |
| atctctcgtt ggaccgacct gatggttgac ctgcagaaaa actctctgca cgttgacgac | 240 |
| gaagctatcg aagttctggg tgaagctgtt gctgaagctg acctgaccct ggttctgggt | 300 |
| accaacgaag tttctgaccg tcagggttct gaaaccctgt acaactctct gttctacttc | 360 |
| gactctaccg tgaactgat gggtcgtcac cgtaaactga tgccgaccca cgaagaacgt | 420 |
| gctatctggg tcgtggtga cccgtcttct ctggctacct acgaaaccga catcggttgg | 480 |
| ctgggtggtc tgatctgcta cgaaaaccac atgaccctgt ctaaagctgc tctgaccgct | 540 |
| atgggtgaag aaatccacgc tgctgtttgg ccgggtttct ggaaacagca cggtcacccg | 600 |
| ggtgacaaaa cccgtgctga aacctctgaa gctgttgaca cctgcgacat ctacccggct | 660 |
| atgcgtgaat acgctttcga aacccagtct ttcgttgctg cttgctctgc ttacatgtct | 720 |
| gacgctgttc cggacggttt ctctgaagac gaactgggtt caacgttgc tgctggtggt | 780 |
| tctatgctga tcaacccggc tggtatcgtt aaagctggtc cgctggttgg tgaagaaggt | 840 |
| ctgctgaccg ctgaattcca ggacgacgaa cgtcgtgcta ccaaagctta cttcgacgct | 900 |
| atgggtcact acaccccgttg gacgctgtt tctctgtcta tcaacgacga aaccctggct | 960 |
| ccgtctcagc gcgtgaacc gtctaaaaac ccggttgctg gtacctcttc tctgtctgct | 1020 |
| gctcaggctc aggctgttgc tgacgaatac gacgttccgg ttgaagctgt tgaagctgtt | 1080 |
| gctgacaaac tgaccgac | 1098 |

<210> SEQ ID NO 72
<211> LENGTH: 366
<212> TYPE: PRT
<213> ORGANISM: Haloarcula sp.
<220> FEATURE:
<223> OTHER INFORMATION: Haloarcula sp. CBA1115

<400> SEQUENCE: 72

Met Pro Ala Glu Ser Phe Thr Leu Ala Ala Gln Val Glu Pro Val
1               5                   10                  15

Tyr His Asp Lys Glu Gly Thr Leu Asp Lys Thr Cys Arg Tyr Ile Glu
             20                  25                  30

Gln Ala Gly Arg Asp Gly Ala Asp Ile Val Val Phe Pro Glu Thr Tyr
         35                  40                  45

Phe Pro Gly Tyr Pro Tyr Trp Arg Gly Ser Val Ser Ile Ser Arg Trp
     50                  55                  60

Thr Asp Leu Met Val Asp Leu Gln Lys Asn Ser Leu His Val Asp Asp
65                  70                  75                  80

Glu Ala Ile Glu Val Leu Gly Glu Ala Val Ala Glu Ala Asp Leu Thr
                85                  90                  95

Leu Val Leu Gly Thr Asn Glu Val Ser Asp Arg Gln Gly Ser Glu Thr
            100                 105                 110

Leu Tyr Asn Ser Leu Phe Tyr Phe Asp Ser Thr Gly Glu Leu Met Gly
            115                 120                 125

Arg His Arg Lys Leu Met Pro Thr His Glu Glu Arg Ala Ile Trp Gly
            130                 135                 140

Arg Gly Asp Pro Ser Ser Leu Ala Thr Tyr Glu Thr Asp Ile Gly Trp
145                 150                 155                 160

Leu Gly Gly Leu Ile Cys Tyr Glu Asn His Met Thr Leu Ser Lys Ala
                165                 170                 175

Ala Leu Thr Ala Met Gly Glu Glu Ile His Ala Ala Val Trp Pro Gly
            180                 185                 190

Phe Trp Lys Gln His Gly His Pro Gly Asp Lys Thr Arg Ala Glu Thr
            195                 200                 205

Ser Glu Ala Val Asp Thr Cys Asp Ile Tyr Pro Ala Met Arg Glu Tyr
            210                 215                 220

Ala Phe Glu Thr Gln Ser Phe Val Ala Ala Cys Ser Ala Tyr Met Ser
225                 230                 235                 240

Asp Ala Val Pro Asp Gly Phe Ser Glu Asp Glu Leu Gly Phe Asn Val
                245                 250                 255

Ala Ala Gly Gly Ser Met Leu Ile Asn Pro Ala Gly Ile Val Lys Ala
            260                 265                 270

Gly Pro Leu Val Gly Glu Gly Leu Leu Thr Ala Glu Phe Gln Asp
            275                 280                 285

Asp Glu Arg Arg Ala Thr Lys Ala Tyr Phe Asp Ala Met Gly His Tyr
290                 295                 300

Thr Arg Trp Asp Ala Val Ser Leu Ser Ile Asn Asp Glu Thr Leu Ala
305                 310                 315                 320

Pro Ser Gln Pro Arg Glu Pro Ser Lys Asn Pro Val Ala Gly Thr Ser
            325                 330                 335

Ser Leu Ser Ala Ala Gln Ala Gln Ala Val Ala Asp Glu Tyr Asp Val
            340                 345                 350

Pro Val Glu Ala Val Glu Ala Val Ala Asp Lys Leu Thr Asp
            355                 360                 365

<210> SEQ ID NO 73
<211> LENGTH: 1062
<212> TYPE: DNA
<213> ORGANISM: Hungatella hathewayi

<400> SEQUENCE: 73
atgtctaaaa aagaaaccgt taaagaagtt acccacacca tcggtgacac cctgccgaaa      60
ctgcgtgctg ctgctgttca ggctgctccg gttttcctga accgtgacgc taccgttcag     120
aaagttgctc gtctgaccaa agaagctaaa gacaacggtg ctgacctggt tgttttcccg     180
gaatctttca tcccgacctt cccgctgtgg tgcctgttcc tgccgccggt tgaccagcac     240
ccgttctaca acgtctgtt cgaaaacgct gttaccgttc cggtccggc ttccacgaa       300 ctgcagaaaa tcgctcgtga caactctatc ttcctgtctg ttggtatctg cgaaaaatct     360
acctctaact tcggtaccat gtggaacacc ccctgctgt tcgaccgtga aggtaacatg     420
atcggtcacc accgtaaact gctgccgacc tggggtgaaa aactggtttg gtctttcggt     480
gacggttctt ctctgaacat ccacgacacc gaaatcggtc gtatcggttc tctgatctgc     540

```
ggtgaaaact ctaacaccct ggctcgttac gctctggttg ctcagggtga acaggttcac      600
atctctgttt acccgccgtg ctggccgacc aaccgtgaaa aaggtaacta cgctgactgc      660
ctgcgtgttc gtacctgcgc tcacgctttc gaagctaaag ttttcaacat ctgctcttct      720
gcttctctgg acgaagacgc tatggaacag atgtctatgg gtgacccggc tctgaaagaa      780
tggctgcaca accagtcttg ggctctgacc atgatcgctg gtccgaacgg tcagccgtgc      840
tgcccgtcta tcgaaaacaa ccaggaaggt atcatctacg ctgactgcga catcgctaac      900
gaaatcaccg ctaaaggtat ccacgacatc gctggtgctt accagcgttt cgacgttttc      960
cagctgcacg ttaacaaaac cccgcgtgaa ccggcttact tctacgacga aggtatcggt     1020
gaatctcgtg aatacatccc gtacgaagaa aagacaccg aa                         1062
```

<210> SEQ ID NO 74
<211> LENGTH: 354
<212> TYPE: PRT
<213> ORGANISM: Hungatella hathewayi

<400> SEQUENCE: 74

```
Met Ser Lys Lys Glu Thr Val Lys Glu Val Thr His Thr Ile Gly Asp
1               5                   10                  15

Thr Leu Pro Lys Leu Arg Ala Ala Val Gln Ala Ala Pro Val Phe
            20                  25                  30

Leu Asn Arg Asp Ala Thr Val Gln Lys Val Ala Arg Leu Thr Lys Glu
        35                  40                  45

Ala Lys Asp Asn Gly Ala Asp Leu Val Val Phe Pro Glu Ser Phe Ile
    50                  55                  60

Pro Thr Phe Pro Leu Trp Cys Leu Phe Leu Pro Pro Val Asp Gln His
65                  70                  75                  80

Pro Phe Tyr Lys Arg Leu Phe Glu Asn Ala Val Thr Val Pro Gly Pro
                85                  90                  95

Ala Phe His Glu Leu Gln Lys Ile Ala Arg Asp Asn Ser Ile Phe Leu
            100                 105                 110

Ser Val Gly Ile Cys Glu Lys Ser Thr Ser Asn Phe Gly Thr Met Trp
        115                 120                 125

Asn Thr Thr Leu Leu Phe Asp Arg Glu Gly Asn Met Ile Gly His His
    130                 135                 140

Arg Lys Leu Leu Pro Thr Trp Gly Glu Lys Leu Val Trp Ser Phe Gly
145                 150                 155                 160

Asp Gly Ser Ser Leu Asn Ile His Asp Thr Glu Ile Gly Arg Ile Gly
                165                 170                 175

Ser Leu Ile Cys Gly Glu Asn Ser Asn Thr Leu Ala Arg Tyr Ala Leu
            180                 185                 190

Val Ala Gln Gly Glu Gln Val His Ile Ser Val Tyr Pro Pro Cys Trp
        195                 200                 205

Pro Thr Asn Arg Glu Lys Gly Asn Tyr Ala Asp Cys Leu Arg Val Arg
    210                 215                 220

Thr Cys Ala His Ala Phe Glu Ala Lys Val Phe Asn Ile Cys Ser Ser
225                 230                 235                 240

Ala Ser Leu Asp Glu Asp Ala Met Glu Gln Met Ser Met Gly Asp Pro
                245                 250                 255

Ala Leu Lys Glu Trp Leu His Asn Gln Ser Trp Ala Leu Thr Met Ile
            260                 265                 270

Ala Gly Pro Asn Gly Gln Pro Cys Cys Pro Ser Ile Glu Asn Asn Gln
```

```
                275                 280                 285
        Glu Gly Ile Ile Tyr Ala Asp Cys Asp Ile Ala Asn Glu Ile Thr Ala
            290                 295                 300
        Lys Gly Ile His Asp Ile Ala Gly Ala Tyr Gln Arg Phe Asp Val Phe
        305                 310                 315                 320
        Gln Leu His Val Asn Lys Thr Pro Arg Glu Pro Ala Tyr Phe Tyr Asp
                        325                 330                 335
        Glu Gly Ile Gly Glu Ser Arg Glu Tyr Ile Pro Tyr Glu Glu Glu Asp
                    340                 345                 350

Thr Glu

<210> SEQ ID NO 75
<211> LENGTH: 5365
<212> TYPE: DNA
<213> ORGANISM: Artificial sequence
<220> FEATURE:
<223> OTHER INFORMATION: Plasmid

<400> SEQUENCE: 75
cgatcaccac aattcagcaa attgtgaaca tcatcacgtt catctttccc tggttgccaa      60
tggcccattt tcctgtcagt aacgagaagg tcgcgaattc aggcgctttt tagactggtc     120
gtaatgaaca attcttaaga aggagatata catatgcaga caagaaaaat cgtccgggca     180
gccgccgtac aggccgcctc tcccaactac gatctggcaa cgggtgttga taaaaccatt     240
gagctggctc gtcaggcccg cgatgagggc tgtgacctga tcgtgtttgg tgaaacctgg     300
ctgcccggat atcccttcca cgtctggctg gcgcaccgg cctggtcgct gaaatacagt     360
gcccgctact atgccaactc gctctcgctg acagtgcag agtttcaacg cattgcccag     420
gccgcacgga ccttgggtat tttcatcgca ctgggttata gcgagcgcag cggcggcagc     480
ctttacctgg ccaatgcct gatcgacgac aagggcgaga tgctgtggtc gcgtcgcaaa     540
ctcaaaccca gcatgtaga gcgcaccgta tttggtgaag ttatgcccg tgatctgatt     600 gtgtccgaca cagaactggg acgcgtcggt gctctatgct gctgggagca tttgtcgccc     660
ttgagcaagt acgcgctgta ctcccagcat gaagccattc acattgctgc ctggccgtcg     720
ttttcgctat acagcgaaca ggcccacgcc ctcagtgcca aggtgaacat ggctgcctcg     780
caaatctatt cggttgaagg ccagtgcttt accatcgccg ccagcagtgt ggtcacccaa     840
gagacgctag acatgctgga agtgggtgaa cacaacgccc ccttgctgaa agtgggcggc     900
ggcagttcca tgattttttgc gccggacgga cgcacactgg ctccctacct gcctcacgat     960
gccgagggct tgatcattgc cgatctgaat atggaggaga ttgccttcgc caaagcgatc    1020
aatgaccccg taggccacta ttccaaaccc gaggccaccc gtctggtgct ggacttgggg    1080
caccgagacc ccatgactcg ggtgcactcc aaaagcgtga ccagggaaga ggctcccgag    1140
caaggtgtgc aaagcaagat tgcctcagtc gctatcagcc atccacagga ctcggacaca    1200
ctgctagtgc aagagccgtc cttgaggatc cgtcgacctg cagccaagct tggctgtttt    1260
ggcggatgag agaagatttt cagcctgata cagattaaat cagaacgcag aagcggtctg    1320
ataaaacaga atttgcctgg cggcagtagc gcggtggtcc cacctgaccc catgccgaac    1380
tcagaagtga aacgccgtag cgccgatggt agtgtggggt ctccccatgc gagagtaggg    1440
aactgccagg catcaaataa aacgaaaggc tcagtcgaaa gactgggcct ttcgttttat    1500
ctgttgtttg tcggtgaacg ctctcctgag taggacaaat ccgccgggag cggatttgaa    1560
cgttgcgaag caacggcccg gagggtggcg gcaggacgc ccgccataaa ctgccaggca    1620
```

-continued

```
tcaaattaag cagaaggcca tcctgacgga tggccttttt gcgtttctac aaactctttt    1680
gtttatttt  ctaaatacat tcaaatatgt atccgctcat gagacaataa ccctgataaa    1740
tgcttcaata atattgaaaa aggaagagta tgagtattca acatttccgt gtcgcccta     1800
ttccctttt  tgcggcattt tgccttcctg tttttgctca cccagaaacg ctggtgaaag    1860
taaaagatgc tgaagatcag ttgggtgcac gagtgggtta catcgaactg gatctcaaca    1920
gcggtaagat ccttgagagt tttcgccccg aagaacgttt tccaatgatg agcactttta    1980
aagttctgct atgtggcgcg gtattatccc gtgttgacgc cgggcaagag caactcggtc    2040
gccgcataca ctattctcag aatgacttgg ttgagtactc accagtcaca gaaaagcatc    2100
ttacggatgg catgacagta agagaattat gcagtgctgc cataaccatg agtgataaca    2160
ctgcggccaa cttacttctg acaacgatcg gaggaccgaa ggagctaacc gcttttttgc    2220
acaacatggg ggatcatgta actcgccttg atcgttggga accggagctg aatgaagcca    2280
taccaaacga cgagcgtgac accacgatgc ctgtagcaat ggcaacaacg ttgcgcaaac    2340
tattaactgg cgaactactt actctagctt cccggcaaca attaatagac tggatggagg    2400
cggataaagt tgcaggacca cttctgcgct cggcccttcc ggctggctgg tttattgctg    2460
ataaatctgg agccggtgag cgtgggtctc gcggtatcat tgcagcactg gggccagatg    2520
gtaagccctc ccgtatcgta gttatctaca cgacggggag tcaggcaact atggatgaac    2580
gaaatagaca gatcgctgag ataggtgcct cactgattaa gcattggtaa ctgtcagacc    2640
aagtttactc atatatactt tagattgatt taaaacttca ttttaatttt aaaaggatct    2700
aggtgaagat cctttttgat aatctcatga ccaaaatccc ttaacgtgag ttttcgttcc    2760
actgagcgtc agaccccgta gaaaagatca aaggatcttc ttgagatcct ttttttctgc    2820
gcgtaatctg ctgcttgcaa acaaaaaaac caccgctacc agcggtggtt tgtttgccgg    2880
atcaagagct accaactctt tttccgaagg taactggctt cagcagagcg cagataccaa    2940
atactgtcct tctagtgtag ccgtagttag gccaccactt caagaactct gtagcaccgc    3000
ctacatacct cgctctgcta atcctgttac cagtggctgc tgccagtggc gataagtcgt    3060
gtcttaccgg gttggactca agacgatagt taccggataa ggcgcagcgg tcgggctgaa    3120
cggggggttc gtgcacacag cccagcttgg agcgaacgac ctacaccgaa ctgagatacc    3180
tacagcgtga gctatgagaa agcgccacgc ttcccgaagg gagaaaggcg gacaggtatc    3240
cggtaagcgg cagggtcgga acaggagagc gcacgaggga gcttccaggg ggaaacgcct    3300
ggtatcttta tagtcctgtc gggtttcgcc acctctgact tgagcgtcga ttttgtgat     3360
gctcgtcagg gggcggagc  ctatggaaaa acgccagcaa cgcggccttt ttacggttcc    3420
tggccttttg ctgccttttt gctcacatgt tctttcctgc gttatcccct gattctgtgg    3480
ataaccgtat taccgccttt gagtgagctg ataccgctcg ccgcagccga acgaccgagc    3540
gcagcgagtc agtgagcgag gaagcggaag agcgcctgat gcggtatttt ctccttacgc    3600
atctgtgcgg tatttcacac cgcatatatg gtgcactctc agtacaatct gctctgatgc    3660
cgcatagtta agccagtata cactccgcta tcgctacgtg actgggtcat ggctgcgccc    3720
cgacacccgc caacacccgc tgacgcgccc tgacgggctt gtctgctccc ggcatccgct    3780
tacagacaag ctgtgaccgt ctccgggagc tgcatgtgtc agaggttttc accgtcatca    3840
ccgaaacgcg cgaggcagct gcggtaaagc tcatcagcgt ggtcgtgaag cgattcacag    3900
atgtctgcct gttcatccgc gtccagctcg ttgagtttct ccagaagcgt taatgtctgg    3960
```

```
cttctgataa agcgggccat gttaagggcg gttttttcct gtttggtcac tgatgcctcc    4020
gtgtaagggg gatttctgtt catgggggta atgataccga tgaaacgaga gaggatgctc    4080
acgatacggg ttactgatga tgaacatgcc cggttactgg aacgttgtga gggtaaacaa    4140
ctggcggtat ggatgcggcg ggaccagaga aaaatcactc agggtcaatg ccagcgcttc    4200
gttaatacag atgtaggtgt tccacagggt agccagcagc atcctgcgat gcagatccgg    4260
aacataatgg tgcagggcgc tgacttccgc gtttccagac tttacgaaac acggaaaccg    4320
aagaccattc atgttgttgc tcaggtcgca gacgttttgc agcagcagtc gcttcacgtt    4380
cgctcgcgta tcggtgattc attctgctaa ccagtaaggc aacccgcca gcctagccgg    4440 gtcctcaacg acaggagcac gatcatgcgc acccgtggcc aggacccaac gctgcccgag    4500
atgcgccgcg tgcggctgct ggagatggcg gacgcgatgg atatgttctg ccaagggttg    4560
gtttgcgcat tcacagttct ccgcaagaat tgattggctc caattcttgg agtggtgaat    4620
ccgttagcga ggtgccgccg gcttccattc aggtcgaggt ggcccggctc catgcaccgc    4680
gacgcaacgc ggggaggcag acaaggtata gggcggcgcc tacaatccat gccaacccgt    4740
tccatgtgct cgccgaggcg gcataaatcg ccgtgacgat cagcggtcca atgatcgaag    4800
ttaggctggt aagagccgcg agcgatcctt gaagctgtcc ctgatggtcg tcatctacct    4860
gcctggacag catggcctgc aacgcgggca tcccgatgcc gccggaagcg agaagaatca    4920
taatggggaa ggccatccag cctcgcgtcg cgaacgccag caagacgtag cccagcgcgt    4980
cggccgccat gccggcgata atggcctgct tctcgccgaa acgtttggtg gcgggaccag    5040
tgacgaaggc ttgagcgagg gcgtgcaaga ttccgaatac cgcaagcgac aggccgatca    5100
tcgtcgcgct ccagcgaaag cggtcctcgc cgaaaatgac ccagagcgct gccggcacct    5160
gtcctacgag ttgcatgata aagaagacag tcataagtgc ggcgacgata gtcatgcccc    5220
gcgcccaccg gaaggagctg actgggttga aggctctcaa gggcatcggt cgacgctctc    5280
ccttatgcga ctcctgcatt aggaagcagc ccagtagtag gttgaggccg ttgagcaccg    5340
ccgccgcaag gaatggtgca tgcat                                         5365
```

METHOD FOR THE PRODUCTION OF ACRYLIC ACID OR SALTS THEREOF

CROSS-REFERENCE TO RELATED APPLICATIONS

This application is a U.S. National Phase Application of International Patent Application No. PCT/EP2019/077369, filed Oct. 9, 2019, which claims the benefit of priority to European Patent Application No. 18201085.0, filed Oct. 18, 2018, and which claims the benefit of priority to European Patent Application No. 19164303.0, filed Mar. 21, 2019, the entire contents of which are hereby incorporated by reference herein.

REFERENCE TO AN ELECTRONIC SEQUENCE LISTING

The contents of the electronic sequence listing (2021 Apr. 13 Sequence Listing 27843-1757.txt; Size: 135,013 bytes; and Date of Creation: Apr. 13, 2021) is herein incorporated by reference in its entirety.

FIELD OF THE INVENTION

The invention is directed to methods for the production of ammonium acrylate or salts thereof from acrylonitrile using nitrilase as catalyst.

DESCRIPTION OF THE INVENTION

Acrylic acid and its derivatives (esters, salts, and amides) are the primary building blocks or monomers in the manufacture of acrylate polymers and co-polymers with numerous applications identified such as surface coatings, adhesives, sealants etc. Acrylic acid is a commodity chemical of considerable value, with an estimated annual production capacity of 4.2 million metric tons. The demand for acrylic acid is continuously increasing due to the increasing use of super absorbents finding their major use in the personal care products. The remainder is used to produce acrylates that are components of acrylic fibres, coatings, paints and inks.

At present, the major source of acrylic acid is produced in the petrochemical industry by oxidation of propylene. Some of the problems encountered during the acrylic acid synthesis from propylene are the damage to the catalysts and the polymerization of the formed products. Although propylene is easily available from fossil fuels, it would be desirable to obtain acrylic acid and its derivatives from renewable resources at an equivalent or lower cost.

The use of biological systems to convert nitrile-containing substrates to carboxylic acids is an attractive alternative to chemical methods because of the high yields than can often be obtained, the mild reaction conditions used, and the specialized activities possessed by some enzymes. Especially advantageous over chemical hydrolysis, enzyme-catalysed hydrolysis of a variety of aliphatic or aromatic dinitriles can be highly regioselective in that only one of the nitrile groups is hydrolyzed. The advantages using biotechnology approaches are high selectivity and yield, cost reduction in the production process, as processes uses less energy and generates less waste. There are two distinct pathways for the enzymatic hydration of nitriles in plants and microorganisms that have been applied in industrial production of acrylic acid. One pathway comprises two enzymatic steps wherein a nitrile hydratase converts a nitrile to an amide which subsequently is hydrolysed by an amidase to yield acrylic acid (U.S. Pat. No. 6,670,158). The other pathway is a single-step reaction catalysed by nitrilases (U.S. Pat. No. 6,162,624) which is advantageous compared to the two-step reaction because the latter requiring an extensive amount of equipment for the two stages. There is a need in the art for providing additional nitrilases capable of catalysing this reaction, especially for nitrilases catalysing the reaction in a more efficient way than nitrilases currently available leading to higher yield and reduced residual acrylonitrile in the final product.

DETAILED DESCRIPTION OF THE INVENTION

One embodiment of the invention at hand is an isolated nitrilase capable of catalysing the reaction from (meth-) acrylonitrile to (meth-) ammonium acrylate in an aqueous medium comprising water, nitrilase and (meth-) acrylonitrile and/or (meth-) ammonium acrylate and optionally a buffer of a pH between including 4 to 9, wherein the concentration of (meth-) ammonium acrylate in the aqueous medium after incubation is at least 10%, at least 15%, at least 20%, at least 25%, at least 30%, at least 35%, preferably at least 40%, at least 45%, more preferably at least 50%, more preferably at least 51%, more preferably at least 52%, more preferably at least 53%, even more preferably at least 54%, most preferably at least 55% (w/w) and the concentration of (meth-) acrylonitrile is below 0.1%, preferably below 0.01%, more preferably below 0.001%, most preferably below 0,0001% (w/w) (meth-) acrylonitrile in the aqueous medium at the end of the incubation.

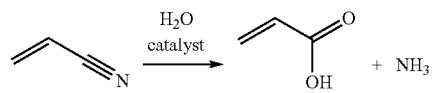

Reaction catalyzed by the nitrilases of the invention.

The aqueous medium may be a solution or a suspension or a solution and a suspension, wherein any of the substances comprised in said aqueous medium may be fully or partially dissolved and/or partially or fully suspended.

In a preferred embodiment, the concentration of acrylonitrile during the incubation and bioconversion should not exceed 8% by wt. for example 6% by wt. and may for example be in the range from 0.1% by wt. to 6% by wt., preferably from 0.2% by wt. to 5% by wt., more preferably from 0.3% by wt. to 4% by wt., even more preferably from 0.5% by wt. to 3% by wt., most preferably from 0.8% by wt. to 2% by wt., still most preferably from 1% by wt. to 1.5% by wt., relating to the total of all components of the aqueous mixture.

Alternatively, the concentration of (meth-) acrylonitrile in the aqueous medium may be up to 8% in solution, preferably 6% in solution at the start of the incubation and might be kept at that concentration during incubation until about 10 min, preferably 15 min, more preferably 20 min, even more preferably 30 min, even more preferably 45 min, most preferably 60 min before the end of the incubation.

In a preferred embodiment, the incubation is performed at 5° C. to 40° C. for 10 minutes to 48 hours, preferably at 5° C. to 35° C. for 1 hour to 24 hours, more preferably at 15° C. to 30° C. for 10 min to 48 hours, most preferably at 18° C. to 28° C. for 3 hours to 15 hours.

In a preferred embodiment, the method is carried out using a semi-batch process.

In a preferred embodiment, the acrylonitrile content is measured using Fourier Transform Infrared Spectroscopy (FTIR).

In another embodiment of the invention, the isolated nitrilase is comprising a sequence selected from the group consisting of The amino acid molecule of SEQ ID NO: 2, 4, 6 and 8 or a functional fragment thereof, and
  a. An amino acid molecule having at least 55% identity to the amino acid molecule of SEQ ID NO: 2, 4, 6 or 8 or a functional fragment thereof, and
  b. An amino acid molecule encoded by a nucleic acid molecule of SEQ ID NO: 1, 3, 5, or 7 or a functional fragment thereof, and
  c. An amino acid molecule encoded by a nucleic acid molecule having at least 70% identity to SEQ ID NO: 1, 3, 5, or 7 or a functional fragment thereof, and
  d. An amino acid molecule encoded by a nucleic acid molecule hybridizing under stringent conditions to a fragment of at least 250 bases complementary to SEQ ID NO: 1, 3, 5, or 7 or a functional fragment thereof, wherein the amino acid molecule as defined in b., d. and e. is catalysing the reaction from (meth-) acrylonitrile to (meth-) ammonium acrylate in an aqueous medium and wherein the concentration of (meth-) ammonium acrylate in the aqueous medium after incubation is at least 10%, at least 15%, at least 20%, at least 25%, at least 30%, at least 35%, preferably at least 40%, at least 45%, more preferably at least 50%, more preferably at least 51%, more preferably at least 52%, more preferably at least 53%, even more preferably at least 54%, most preferably at least 55% (w/w) and the concentration of (meth-) acrylonitrile is below 0.1%, preferably below 0.01%, more preferably below 0.001%, most preferably below 0,0001% (w/w) (meth-) acrylonitrile in the aqueous medium at the end of the incubation.

In one embodiment of the invention, said isolated nitrilase capable of catalysing the reaction from (meth-) acrylonitrile to (meth-) ammonium acrylate wherein the concentration of (meth-) ammonium acrylate in the aqueous medium after incubation is at least 10%, at least 15%, at least 20%, at least 25%, at least 30%, at least 35%, preferably at least 40%, at least 45%, more preferably at least 50%, more preferably at least 51%, more preferably at least 52%, more preferably at least 53%, even more preferably at least 54%, most preferably at least 55% (w/w) and the concentration of (meth-) acrylonitrile is below 0.1%, preferably below 0.01%, more preferably below 0.001%, most preferably below 0,0001% (w/w) (meth-) acrylonitrile in the aqueous medium at the end of the incubation comprises at a position corresponding to positions 56/190 of SEQ ID NO: 2 the amino acids 56W/190L or 56Q/190S or 56D/190S and/or comprises at a position corresponding to position 190/192 of SEQ ID NO: 2 the amino acids 190S/192S or 190S/192G or 190L/192P and/or comprises at a position corresponding to position 190/193 of SEQ ID NO: 2 the amino acids 190L/193D or 190S/193E or 190L/193N and/or comprises at a position corresponding to position 202/249 of SEQ ID NO: 2 the amino acids 202L/249E or 202V/249H or 202I/249F or 202N/249W and/or comprises at a position corresponding to position 286/287 of SEQ ID NO: 2 the amino acids 286M/287A or 286R/287L or 286A/287G or 286S/287L.

A further embodiment of the invention is a process for producing (meth-) ammonium acrylate comprising the steps of providing an aqueous medium comprising water, one or more nitrilases and (meth-) acrylonitrile, and optionally a buffer having a pH of 4 to 9 a) incubating the aqueous medium and
b) optionally isolating the (meth-) ammonium acrylate from the reaction mixture, wherein the one or more nitrilase is selected from the group consisting of
  i. an amino acid molecule of SEQ ID NO: 2, 4, 6, 8, 10, 12, 14, 18, 20, 22, 26, 28, 30, 32, 34, 38, 40, 42, 46, 48, 52, 54, 56, 60, 62, 64, 66 and 68 or a functional fragment thereof, and
  ii. an amino acid molecule having at least 55% identity to the amino acid molecule of SEQ ID NO: SEQ ID NO: 2, 4, 6, 8, 10, 12, 14, 18, 20, 22, 26, 28, 30, 32, 34, 38, 40, 42, 46, 48, 52, 54, 56, 60, 62, 64, 66 or 68 or a functional fragment thereof, and,
  iii. an amino acid molecule encoded by a nucleic acid molecule of SEQ ID NO 1, 3, 5, 7, 9, 11, 13, 15, 17, 19, 21, 25, 27, 29, 31, 33, 37, 39, 41, 45, 47, 51, 53, 55, 59, 61, 63, 65 or 67 or a functional fragment thereof, and
  iv. an amino acid molecule encoded by a nucleic acid molecule having at least 70% identity to SEQ ID NO: 1, 3, 5, 7, 9, 11, 13, 15, 17, 19, 21, 25, 27, 29, 31, 33, 37, 39, 41, 45, 47, 51, 53, 55, 59, 61, 63, 65 or 67 or a functional fragment thereof, and
  v. an amino acid molecule encoded by a nucleic acid molecule hybridizing under stringent conditions to a fragment of at least 250 bases complementary to SEQ ID NO 1, 3, 5, 7, 9, 11, 13, 15, 17, 19, 21, 25, 27, 29, 31, 33, 37, 39, 41, 45, 47, 51, 53, 55, 59, 61, 63, 65 or 67 or a functional fragment thereof, wherein the amino acid molecule as defined in ii., iv. and v. have the activity of converting (meth-) acrylonitrile to (meth-) ammonium acrylate.

In table 1 examples for functional variants of the amino acid molecules of SEQ ID 2, 4, 6, 8, 10, 12, 14, 18, 20, 22, 26, 28, 30, 32, 34, 38, 40, 42, 46, 48, 52, 54, 56, 60, 62, 64, 66 and 68 are listed having a certain identity to the respective SEQ ID. Further the SEQ ID of the respective nucleic acid are listed encoding the respective functional variant amino acid molecule.

TABLE 1

| Seq. ID | Donor | SEQ ID amino acid | SEQ ID nucleic acid | Identity |
|---|---|---|---|---|
| 2 | Unknown | 77 | 76 | 90% |
|   |   | 79 | 78 | 85% |
|   |   | 81 | 80 | 80% |
| 4 | Unknown | 83 | 82 | 90% |
|   |   | 85 | 84 | 85% |
|   |   | 87 | 86 | 80% |
| 6 | Flavihumibacter solisilvae | 89 | 88 | 90% |
|   |   | 91 | 90 | 85% |
|   |   | 93 | 92 | 80% |
| 8 | Acidovorax facilis | 95 | 94 | 90% |
|   |   | 97 | 96 | 85% |
|   |   | 99 | 98 | 80% |
| 10 | Pseudomonas sp | 101 | 100 | 90% |
|   |   | 103 | 102 | 85% |
|   |   | 105 | 104 | 80% |
| 12 | Nocardia brasiliensis | 107 | 106 | 90% |
|   |   | 109 | 108 | 85% |
|   |   | 111 | 110 | 80% |
| 14 | Pseudomonas fluorescens | 113 | 112 | 90% |
|   |   | 115 | 114 | 85% |
|   |   | 117 | 116 | 80% |
| 16 | Agrobacterium rubi | 119 | 118 | 90% |
|   |   | 121 | 120 | 85% |
|   |   | 123 | 122 | 80% |

TABLE 1-continued

| Seq. ID | Donor | SEQ ID amino acid | SEQ ID nucleic acid | Identity |
|---|---|---|---|---|
| 18 | Unknown | 125 | 124 | 90% |
|  |  | 127 | 126 | 85% |
|  |  | 129 | 128 | 80% |
| 20 | Candidatus Dadabacteria | 131 | 130 | 90% |
|  |  | 133 | 132 | 85% |
|  |  | 135 | 134 | 80% |
| 22 | Unknown | 137 | 136 | 90% |
|  |  | 139 | 138 | 85% |
|  |  | 141 | 140 | 80% |
| 26 | Tepidicaulis marinus | 149 | 148 | 90% |
|  |  | 151 | 150 | 85% |
|  |  | 153 | 152 | 80% |
| 28 | Unknown | 155 | 154 | 90% |
|  |  | 157 | 156 | 85% |
|  |  | 159 | 158 | 80% |
| 30 | Unknown | 161 | 160 | 90% |
|  |  | 163 | 162 | 85% |
|  |  | 165 | 164 | 80% |
| 32 | Unknown | 167 | 166 | 90% |
|  |  | 169 | 168 | 85% |
|  |  | 171 | 170 | 80% |
| 34 | Synechococcus sp. | 173 | 172 | 90% |
|  |  | 175 | 174 | 85% |
|  |  | 177 | 176 | 80% |
| 38 | Aquimarina atlantica | 185 | 184 | 90% |
|  |  | 187 | 186 | 85% |
|  |  | 189 | 188 | 80% |
| 40 | Arthrobacter sp. | 191 | 190 | 90% |
|  |  | 193 | 192 | 85% |
|  |  | 195 | 194 | 80% |
| 42 | Cupriavidus basilensis | 197 | 196 | 90% |
|  |  | 199 | 198 | 85% |
|  |  | 201 | 200 | 80% |
| 46 | Sphingomonas wittichii | 209 | 208 | 90% |
|  |  | 211 | 210 | 85% |
|  |  | 213 | 212 | 80% |
| 48 | Pseudomonas mandelii | 215 | 214 | 90% |
|  |  | 217 | 216 | 85% |
|  |  | 219 | 218 | 80% |
| 52 | Arabidopsis thaliana | 227 | 226 | 90% |
|  |  | 229 | 228 | 85% |
|  |  | 231 | 230 | 80% |
| 54 | Brassica oleracea | 233 | 232 | 90% |
|  |  | 235 | 234 | 85% |
|  |  | 237 | 236 | 80% |
| 56 | Salinisphaera shabanensis | 239 | 238 | 90% |
|  |  | 241 | 240 | 85% |
|  |  | 243 | 242 | 80% |
| 60 | Smithella sp. | 251 | 250 | 90% |
|  |  | 253 | 252 | 85% |
|  |  | 255 | 254 | 80% |
| 62 | Bradyrhizobium diazoefficiens | 257 | 256 | 90% |
|  |  | 259 | 258 | 85% |
|  |  | 261 | 260 | 80% |
| 64 | Actinobacteria bacterium | 263 | 262 | 90% |
|  |  | 265 | 264 | 85% |
|  |  | 267 | 266 | 80% |
| 66 | Rhizobium sp. | 269 | 268 | 90% |
|  |  | 271 | 270 | 85% |
|  |  | 273 | 272 | 80% |
| 68 | bacterium YEK0313 | 275 | 274 | 90% |
|  |  | 277 | 276 | 85% |
|  |  | 279 | 278 | 80% |

The aqueous medium at the end of the incubation comprises less than 1% (w/w) acrylamide as by-product, preferably less than 0.5%, more preferably less than 0.1%.

At the start of the process of the invention, the aqueous medium may comprise at least 0.05% (meth-) acrylonitrile, preferably at least 0.1% (meth-) acrylonitrile, more preferably at least 0.5% (meth-) acrylonitrile, most preferably at least 1.0% (meth-) acrylonitrile (w/w). Throughout the incubation the concentration of (meth-) acrylonitrile may be kept at a concentration of about 0.5% to 1.5%, preferably about 1.0% (meth-) acrylonitrile by continuous feeding of (meth-) acrylonitrile.

Alternatively, the concentration of (meth-) acrylonitrile in the aqueous medium may be 5% or 6% at the start of the incubation and might be kept at that concentration or no further (meth-) acrylonitrile may be added during incubation.

The incubation time of the aqueous medium may be at least 5 h, at least 10 h or at least 12 h. Preferably the incubation time is at least 18 h, for example about 24 h or about 30 h. More preferably the incubation time is about 36 h or about 42 h. Most preferably, the incubation time is about 48 h. Depending on the nitrilase used and the reaction rate of said nitrilase, the incubation time may also exceed 48 h.

The aqueous medium may be incubated at at least 15° C., at least 20° C., at least 24° C. or at least 28° C. Preferably the aqueous medium is incubated between including 27° C. and 33° C., more preferably the aqueous medium is incubated between including 28° C. and 30° C. Most preferably the aqueous medium is incubated at 28° C. The aqueous medium may also be incubated at 38° C., 39° C., 40° C., 41° C., 42° C., 43° C., 44° C., 45° C., 46° C., 47° C., 48° C., 49° C. or 50° C.

In a preferred embodiment, the method is carried out using a semi-batch process.

In a preferred embodiment, the acrylonitrile content is measured using Fourier Transform Infrared Spectroscopy (FTIR).

In one embodiment of the invention, aqueous solutions of ammonium (meth-) acrylate may be manufactured at a fixed chemical plant and may be shipped to another location for further processing. In another preferred embodiment of the present invention the manufacture of ammonium (meth-) acrylate may be performed in a modular, relocatable plant. Further preferred is for example a relocatable conversion unit, which can be combined with installations and/or units of a fixed chemical plant. Such combination of an existing plant with a modular, relocatable conversion unit offers flexibility in building a production line based on case specific needs. Such production line at a certain plant can be adjusted easily in case the production requirements change. The existing plant for example may be a fixed polymerization plant for homopolymers of (meth-) acrylic acid and/or copolymers of for example (meth-) acrylic acid and acrylamide. So, the combination of a relocatable conversion unit offers the possibility of combining the manufacturing of ammonium (meth-) acrylate with units for further processing the ammonium (meth-) acrylate obtained from a relocatable bioconversion unit.

The nitrilase used in the process of the invention may be isolated from the organism naturally expressing said nitrilase. Alternatively, the nitrilase may be added to the aqueous medium by adding cells comprising said nitrilase or by adding a suspension comprising inactivated, for example disrupted cells. In another embodiment of the invention, the nitrilase may be produced in recombinant organisms, preferably microorganisms, expressing the nitrilase of the invention from a heterologous construct. The nitrilase so produced may be isolated from the recombinant organism and added to the aqueous medium or the nitrilase may be added by inactivating, for example disrupting the cells and adding the suspension.

The cells or suspension comprising inactivated cells may be at least partially concentrated for example by drying before being added to the aqueous medium used in the methods of the invention or to the composition of the invention.

The nitrilase may be (partly) immobilized for instance entrapped in a gel or it may be used for example as a free cell suspension. For immobilization well known standard methods can be applied like for example entrapment cross linkage such as glutaraldehyde-polyethyleneimine (GA-PEI) crosslinking, cross linking to a matrix and/or carrier binding etc., including variations and/or combinations of the aforementioned methods. Alternatively, the nitrilase enzyme may be extracted and for instance may be used directly in the process for preparing the amide. When using inactivated or partly inactivated cells, such cells may be inactivated by thermal or chemical treatment.

A further embodiment of the invention is and isolated nitrilase comprising a sequence selected from the group consisting of an amino acid molecule of SEQ ID NO: 2, 4, 6, 8, 10, 12, 14, 18, 20, 22, 26, 28, 30, 32, 34, 38, 40, 42, 46, 48, 52, 54, 56, 60, 62, 64, 66 and 68 or a functional fragment thereof, and an amino acid molecule having at least 55% identity to the amino acid molecule of SEQ ID NO: SEQ ID NO: 2, 4, 6, 8, 10, 12, 14, 18, 20, 22, 26, 28, 30, 32, 34, 38, 40, 42, 46, 48, 52, 54, 56, 60, 62, 64, 66 or 68 or a functional fragment thereof, and, an amino acid molecule encoded by a nucleic acid molecule of SEQ ID NO 1, 3, 5, 7, 9, 11, 13, 15, 17, 19, 21, 25, 27, 29, 31, 33, 37, 39, 41, 45, 47, 51, 53, 55, 59, 61, 63, 65 or 67 or a functional fragment thereof, and an amino acid molecule encoded by a nucleic acid molecule having at least 70% identity to SEQ ID NO: 1, 3, 5, 7, 9, 11, 13, 15, 17, 19, 21, 25, 27, 29, 31, 33, 37, 39, 41, 45, 47, 51, 53, 55, 59, 61, 63, 65 or 67 or a functional fragment thereof, and an amino acid molecule encoded by a nucleic acid molecule hybridizing under stringent conditions to a fragment of at least 250 bases complementary to SEQ ID NO 1, 3, 5, 7, 9, 11, 13, 15, 17, 19, 21, 25, 27, 29, 31, 33, 37, 39, 41, 45, 47, 51, 53, 55, 59, 61, 63, 65 or 67 or a functional fragment thereof, wherein the amino acid molecule as defined in b., d. and e. is catalysing the reaction from (meth-) acrylonitrile to (meth-) ammonium acrylate in an aqueous medium.

A further embodiment of the invention is a recombinant construct comprising a nitrilase wherein the nitrilase is selected from the group consisting of an amino acid molecule of SEQ ID NO: 2, 4, 6, 8, 10, 12, 14, 18, 20, 22, 26, 28, 30, 32, 34, 38, 40, 42, 46, 48, 52, 54, 56, 60, 62, 64, 66 and 68 or a functional fragment thereof, and an amino acid molecule having at least 55% identity to the amino acid molecule of SEQ ID NO: SEQ ID NO: 2, 4, 6, 8, 10, 12, 14, 18, 20, 22, 24, 26, 28, 30, 32, 34, 36, 38, 40, 42, 44, 46, 48, 50, 52, 54, 56, 58, 60, 62, 64, 66 or 68 or a functional fragment thereof, and, an amino acid molecule encoded by a nucleic acid molecule of SEQ ID NO 1, 3, 5, 7, 9, 11, 13, 15, 17, 19, 21, 25, 27, 29, 31, 33, 37, 39, 41, 45, 47, 51, 53, 55, 59, 61, 63, 65 or 67 or a functional fragment thereof, and an amino acid molecule encoded by a nucleic acid molecule having at least 70% identity to SEQ ID NO: 1, 3, 5, 7, 9, 11, 13, 15, 17, 19, 21, 25, 27, 29, 31, 33, 37, 39, 41, 45, 47, 51, 53, 55, 59, 61, 63, 65 or 67 or a functional fragment thereof, and an amino acid molecule encoded by a nucleic acid molecule hybridizing under stringent conditions to a fragment of at least 250 bases complementary to SEQ ID NO 1, 3, 5, 7, 9, 11, 13, 15, 17, 19, 21, 25, 27, 29, 31, 33, 37, 39, 41, 45, 47, 51, 53, 55, 59, 61, 63, 65 or 67 or a functional fragment thereof, wherein the amino acid molecule as defined in ii., iv. and v. is catalysing the reaction from (meth-) acrylonitrile to (meth-) ammonium acrylate in an aqueous medium.

Said recombinant construct may be integrated into the genome of an organism for producing and isolating the respective nitrilase or the nitrilase may be expressed from a vector such as a plasmid or viral vector that is introduced into an organism for producing and isolating said nitrilase.

The nitrilase in the recombinant construct may be functionally linked to a heterologous promoter, a heterologous terminator or any other heterologous genetic element.

A further embodiment of the invention is a recombinant vector, such a s an expression vector or a viral vector comprising said recombinant construct.

A recombinant microorganism comprising said recombinant construct or said recombinant vector is also an embodiment of the invention.

In some embodiments, the recombinant microorganism is a prokaryotic cell. Suitable prokaryotic cells include Gram-positive, Gram negative and Gram-variable bacterial cells, preferably Gram-negative.

Thus, microorganisms that can be used in the present invention include, but are not limited to, *Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Brevibacterium ammoniagenes, Brevibacterium divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Micrococcus* sp. CCM825, *Morganella morganii, Nocardia opaca, Nocardia rugosa, Planococcus eucinatus, Proteus rettgeri, Propionibacterium shermanii, Pseudomonas synxantha, Pseudomonas azotoformans, Pseudomonas jluorescens, Pseudomonas ovalis, Pseudomonas stutzeri, Pseudomonas acidovolans, Pseudomonas mucidolens, Pseudomonas testosterone, Pseudomonas aeruginosa, Rhodococcus erythropolis, Rhodococcus rhodochrous, Rhodococcus* sp. ATCC 15592, *Rhodococcus* sp. ATCC 19070, *Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces avermitilis, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomy-* ces lavendulae, *Streptomyces viridochromogenes*, *Aeromonas salmonicida*, *Bacillus pumilus*, *Bacillus circulans*, *Bacillus thiaminolyticus*, *Escherichia freundii*, *Microbacterium ammoniaphilum*, *Serratia marcescens*, *Salmonella typhimurium*, *Salmonella schottmulleri*, *Xanthomonas citri*, *Synechocystis* sp., *Synechococcus elongatus*, *Thermosynechococcus elongatus*, *Microcystis aeruginosa*, *Nostoc* sp., *N. commune*, *N. sphaericum*, *Nostoc punctiforme*, *Spirulina platensis*, *Lyngbya majuscule*, *L. lagerheimii*, *Phormidium tenue*, *Anabaena* sp., *Leptolyngbya* sp and so forth.

In some embodiments, the microorganism is a eukaryotic cell. Suitable eukaryotic cells include yeast cells, as for example *Saccharomyces* spec, such as *Saccharomyces cerevisiae*, *Hansenula* spec, such as *Hansenula polymorpha*, *Schizosaccharomyces* spec, such as *Schizosaccharomyces pombe*, *Kluyveromyces* spec, such as *Kluyveromyces lactis* and *Kluyveromyces marxianus*, *Yarrowia* spec, such as *Yarrowia lipolytica*, *Pichia* spec, such as *Pichia methanolica*, *Pichia stipites* and *Pichia pastoris*, *Zygosaccharomyces* spec, such as *Zygosaccharomyces rouxii* and *Zygosaccharomyces bailii*, *Candida* spec, such as *Candida boidinii*, *Candida utilis*, *Candida freyschussii*, *Candida glabrata* and *Candida sonorensis*, *Schwanniomyces* spec, such as *Schwanniomyces occidentalis*, *Arxula* spec, such as *Arxula adeninivorans*, *Ogataea* spec such as *Ogataea minuta*, *Klebsiella* spec, such as *Klebsiella pneumonia*.

A microorganism of the genus *Cupriavidus basilensis*, *Flavihumibacter solisilvae*, *Acidovorax facilis* 72W, *Pseudomonas* sp. RIT357, *Nocardia brasiliensis* NBRC 14402, *Pseudomonas fluorscens*, *Agrobacterium rubi*, *Candidatus Dadabacteria bacterium* CSP1-2, *Tepidicaulis marinus*, *Synechococcus* sp. CC9605, *Aquimarina atlantica*, *Arthrobacter* sp., *Sphingomonas wittichii* RW1, *Pseudomonas mandelii* JR-1, *Salinisphaera shabanensis* E13A, *Smithella* sp. SDB, *Bradyrhizobium diazoefficiens*, *Actinobacteria bacterium* RBG_13_55_18, *Rhizobium* sp. YK2 or *Bacterium* YEK0313 expressing any of the nitrilases of the invention is another embodiment of the invention.

A further embodiment of the invention is a method for producing a nitrilase, comprising the steps of
a) providing a recombinant microorganism expressing at least one of the nitrilases of the invention or a microorganism naturally expressing a nitrilase of the invention, and
b) cultivating said microorganism under conditions allowing for the expression of said nitrilase gene, and
c) optionally isolating the nitrilase of the invention from said microorganism.

Another embodiment of the invention is a composition comprising water, a nitrilase, (meth-) acrylonitrile and/or (meth-) ammonium acrylate wherein the nitrilase is selected from the group consisting of
an amino acid molecule of SEQ ID NO: 2, 4, 6, 8, 10, 12, 14, 18, 20, 22, 26, 28, 30, 32, 34, 38, 40, 42, 46, 48, 52, 54, 56, 60, 62, 64, 66 and 68 or a functional fragment thereof, and
an amino acid molecule having at least 55% identity to the amino acid molecule of SEQ ID NO: SEQ ID NO: 2, 4, 6, 8, 10, 12, 14, 18, 20, 22, 26, 28, 30, 32, 34, 38, 40, 42, 46, 48, 52, 54, 56, 60, 62, 64, 66 or 68, and,
an amino acid molecule encoded by a nucleic acid molecule of SEQ ID NO 1, 3, 5, 7, 9, 11, 13, 15, 17, 19, 21, 25, 27, 29, 31, 33, 37, 39, 41, 45, 47, 51, 53, 55, 59, 61, 63, 65 or 67 or a functional fragment thereof, and
an amino acid molecule encoded by a nucleic acid molecule having at least 70% identity to SEQ ID NO: 1, 3, 5, 7, 9, 11, 13, 15, 17, 19, 21, 25, 27, 29, 31, 33, 37, 39, 41, 45, 47, 51, 53, 55, 59, 61, 63, 65 or 67 or a functional fragment thereof, and
an amino acid molecule encoded by a nucleic acid molecule hybridizing under stringent conditions to a fragment of at least 250 bases complementary to SEQ ID NO 1, 3, 5, 7, 9, 11, 13, 15, 17, 19, 21, 25, 27, 29, 31, 33, 37, 39, 41, 45, 47, 51, 53, 55, 59, 61, 63, 65 or 67 or a functional fragment thereof,
wherein the amino acid molecule as defined in ii., iv. and v. is catalysing the reaction from (meth-) acrylonitrile to (meth-) ammonium acrylate in an aqueous medium.

Amino acid molecules and nucleic acid molecules having a certain identity to any of the sequences of SEQ ID NO 1 to 68 include nucleic acid molecules and amino acid molecules having 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to any of SEQ ID NO:1 to 68.

Preferably, the nitrilase amino acid sequences having a certain identity to the nitrilases of SEQ ID NO: 2, 4, 6, 8, 10, 12, 14, 18, 20, 22, 26, 28, 30, 32, 34, 38, 40, 42, 46, 48, 52, 54, 56, 60, 62, 64, 66 and 68 comprise some, preferably predominantly, conservative amino acid substitutions. Conservative substitutions are those where one amino acid is exchanged with a similar amino acid. For determination of %-similarity the following applies, which is also in accordance with the BLOSUM62 matrix, which is one of the most used amino acids similarity matrix for database searching and sequence alignments:

Amino acid A is similar to amino acids S
Amino acid D is similar to amino acids E; N
Amino acid E is similar to amino acids D; K; Q
Amino acid F is similar to amino acids W; Y
Amino acid H is similar to amino acids N; Y
Amino acid I is similar to amino acids L; M; V
Amino acid K is similar to amino acids E; Q; R
Amino acid L is similar to amino acids I; M; V
Amino acid M is similar to amino acids I; L; V
Amino acid N is similar to amino acids D; H; S
Amino acid Q is similar to amino acids E; K; R
Amino acid R is similar to amino acids K; Q
Amino acid S is similar to amino acids A; N; T
Amino acid T is similar to amino acids S
Amino acid V is similar to amino acids I; L; M
Amino acid W is similar to amino acids F; Y
Amino acid Y is similar to amino acids F; H; W Conservative amino acid substitutions may occur over the full length of the sequence of a polypeptide sequence of a functional protein such as an enzyme. In one embodiment, such mutations are not pertaining the functional domains of an enzyme. In one embodiment, conservative mutations are not pertaining the catalytic centers of an enzyme.

A functional fragment of the amino acid molecules selected from SEQ ID NO: 2, 4, 6, 8, 10, 12, 14, 18, 20, 22, 26, 28, 30, 32, 34, 38, 40, 42, 46, 48, 52, 54, 56, 60, 62, 64, 66 and 68 comprises at least 100 amino acids, preferably at least 150 amino acids, more preferably at least 200 amino acids, more preferably at least 250 amino acids, most preferably at least 300 amino acids.

Definitions

It is to be understood that this invention is not limited to the particular methodology or protocols. It is also to be understood that the terminology used herein is for the purpose of describing particular embodiments only and is not intended to limit the scope of the present invention which will be limited only by the appended claims. It must be noted that as used herein and in the appended claims, the singular forms "a," "and," and "the" include plural reference unless the context clearly dictates otherwise. Thus, for example, reference to "a vector" is a reference to one or more vectors and includes equivalents thereof known to those skilled in the art, and so forth. The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). As used herein, the word "or" means any one member of a particular list and also includes any combination of members of that list. The words "comprise," "comprising," "include," "including," and "includes" when used in this specification and in the following claims are intended to specify the presence of one or more stated features, integers, components, or steps, but they do not preclude the presence or addition of one or more other features, integers, components, steps, or groups thereof. For clarity, certain terms used in the specification are defined and used as follows:

Coding region: As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5'-side by the nucleotide triplet "ATG" which encodes the initiator methionine, prokaryotes also use the triplets "GTG" and "TTG" as start codon. On the 3'-side it is bounded by one of the three triplets which specify stop codons (i.e., TAA, TAG, TGA). In addition a gene may include sequences located on both the 5'- and 3'-end of the sequences which are present on the RNA transcript. These sequences are referred to as "flanking" sequences or regions (these flanking sequences are located 5' or 3' to the non-translated sequences present on the mRNA transcript). The 5'-flanking region may contain regulatory sequences such as promoters and enhancers which control or influence the transcription of the gene. The 3'-flanking region may contain sequences which direct the termination of transcription, post-transcriptional cleavage and polyadenylation.

Complementary: "Complementary" or "complementarity" refers to two nucleotide sequences which comprise antiparallel nucleotide sequences capable of pairing with one another (by the base-pairing rules) upon formation of hydrogen bonds between the complementary base residues in the antiparallel nucleotide sequences. For example, the sequence 5'-AGT-3' is complementary to the sequence 5'-ACT-3'. Complementarity can be "partial" or "total." "Partial" complementarity is where one or more nucleic acid bases are not matched according to the base pairing rules.

"Total" or "complete" complementarity between nucleic acid molecules is where each and every nucleic acid base is matched with another base under the base pairing rules. The degree of complementarity between nucleic acid molecule strands has significant effects on the efficiency and strength of hybridization between nucleic acid molecule strands. A "complement" of a nucleic acid sequence as used herein refers to a nucleotide sequence whose nucleic acid molecules show total complementarity to the nucleic acid molecules of the nucleic acid sequence.

Endogenous: An "endogenous" nucleotide sequence refers to a nucleotide sequence, which is present in the genome of a wild type microorganism.

Enhanced expression: "enhance" or "increase" the expression of a nucleic acid molecule in a microorganism are used equivalently herein and mean that the level of expression of a nucleic acid molecule in a microorganism is higher compared to a reference microorganism, for example a wild type. The terms "enhanced" or "increased" as used herein mean herein higher, preferably significantly higher expression of the nucleic acid molecule to be expressed. As used herein, an "enhancement" or "increase" of the level of an agent such as a protein, mRNA or RNA means that the level is increased relative to a substantially identical microorganism grown under substantially identical conditions. As used herein, "enhancement" or "increase" of the level of an agent, such as for example a preRNA, mRNA, rRNA, tRNA, expressed by the target gene and/or of the protein product encoded by it, means that the level is increased 50% or more, for example 100% or more, preferably 200% or more, more preferably 5 fold or more, even more preferably 10 fold or more, most preferably 20 fold or more for example 50 fold relative to a suitable reference microorganism. The enhancement or increase can be determined by methods with which the skilled worker is familiar. Thus, the enhancement or increase of the nucleic acid or protein quantity can be determined for example by an immunological detection of the protein. Moreover, techniques such as protein assay, fluorescence, Northern hybridization, densitometric measurement of nucleic acid concentration in a gel, nuclease protection assay, reverse transcription (quantitative RT-PCR), ELISA (enzyme-linked immunosorbent assay), Western blotting, radioimmunoassay (RIA) or other immunoassays and fluorescence-activated cell analysis (FACS) can be employed to measure a specific protein or RNA in a microorganism. Depending on the type of the induced protein product, its activity or the effect on the phenotype of the microorganism may also be determined. Methods for determining the protein quantity are known to the skilled worker. Examples, which may be mentioned, are: the micro-Biuret method (Goa J (1953) Scand J Clin Lab Invest 5:218-222), the Folin-Ciocalteau method (Lowry O H et al. (1951) J Biol Chem 193:265-275) or measuring the absorption of CBB G-250 (Bradford M M (1976) Analyt Biochem 72:248-254).

Expression: "Expression" refers to the biosynthesis of a gene product, preferably to the transcription and/or translation of a nucleotide sequence, for example an endogenous gene or a heterologous gene, in a cell. For example, in the case of a structural gene, expression involves transcription of the structural gene into mRNA and—optionally—the subsequent translation of mRNA into one or more polypeptides. In other cases, expression may refer only to the transcription of the DNA harboring an RNA molecule.

Foreign: The term "foreign" refers to any nucleic acid molecule (e.g., gene sequence) which is introduced into a cell by experimental manipulations and may include sequences found in that cell as long as the introduced sequence contains some modification (e.g., a point mutation, the presence of a selectable marker gene, etc.) and is therefore different relative to the naturally-occurring sequence.

Functional fragment: The term "functional fragment" refers to any nucleic acid or amino acid sequence which comprises merely a part of the full length nucleic acid or full length amino acid sequence, respectively, but still has the same or similar activity and/or function. In one embodiment, the fragment comprises at least 70%, at least 80%, at least 85%, at least 90%, at least 95%, at least 96%, at least 97%, at least 98%, at least 99% of the original sequence. In one embodiment, the functional fragment comprises contiguous nucleic acids or amino acids compared to the original nucleic acid or original amino acid sequence, respectively.

Functional linkage: The term "functional linkage" or "functionally linked" is equivalent to the term "operable linkage" or "operably linked" and is to be understood as meaning, for example, the sequential arrangement of a regulatory element (e.g. a promoter) with a nucleic acid sequence to be expressed and, if appropriate, further regulatory elements (such as e.g., a terminator) in such a way that each of the regulatory elements can fulfill its intended function to allow, modify, facilitate or otherwise influence expression of said nucleic acid sequence. As a synonym the wording "operable linkage" or "operably linked" may be used. The expression may result depending on the arrangement of the nucleic acid sequences in relation to sense or antisense RNA. To this end, direct linkage in the chemical sense is not necessarily required. Genetic control sequences such as, for example, enhancer sequences, can also exert their function on the target sequence from positions which are further away, or indeed from other DNA molecules. Preferred arrangements are those in which the nucleic acid sequence to be expressed recombinantly is positioned behind the sequence acting as promoter, so that the two sequences are linked covalently to each other. In a preferred embodiment, the nucleic acid sequence to be transcribed is located behind the promoter in such a way that the transcription start is identical with the desired beginning of the chimeric RNA of the invention. Functional linkage, and an expression construct, can be generated by means of customary recombination and cloning techniques as described (e.g., Sambrook J, Fritsch E F and Maniatis T (1989); Silhavy et al. (1984) Experiments with Gene Fusions, Cold Spring Harbor Laboratory, Cold Spring Harbor (N.Y.); Ausubel et al. (1987) Current Protocols in Molecular Biology, Greene Publishing Assoc. and Wiley Interscience; Gelvin et al. (Eds) (1990) Plant Molecular Biology Manual; Kluwer Academic Publisher, Dordrecht, The Netherlands). However, further sequences, which, for example, act as a linker with specific cleavage sites for restriction enzymes, or as a signal peptide, may also be positioned between the two sequences. The insertion of sequences may also lead to the expression of fusion proteins. Preferably, the expression construct, consisting of a linkage of a regulatory region for example a promoter and nucleic acid sequence to be expressed, can exist in a vector-integrated form or can be inserted into the genome, for example by transformation.

Gene: The term "gene" refers to a region operably linked to appropriate regulatory sequences capable of regulating the expression of the gene product (e.g., a polypeptide or a functional RNA) in some manner. A gene includes untranslated regulatory regions of DNA (e.g., promoters, enhancers, repressors, etc.) preceding (up-stream) and following (downstream) the coding region (open reading frame, ORF). The term "structural gene" as used herein is intended to mean a DNA sequence that is transcribed into mRNA which is then translated into a sequence of amino acids characteristic of a specific polypeptide.

Genome and genomic DNA: The terms "genome" or "genomic DNA" is referring to the heritable genetic information of a host organism. Said genomic DNA comprises the DNA of the nucleoid but also the DNA of the self-replicating plasmid.

Heterologous: The term "heterologous" with respect to a nucleic acid molecule or DNA refers to a nucleic acid molecule which is operably linked to, or is manipulated to become operably linked to, a second nucleic acid molecule to which it is not operably linked in nature, or to which it is operably linked at a different location in nature. A heterologous expression construct comprising a nucleic acid molecule and one or more regulatory nucleic acid molecule (such as a promoter or a transcription termination signal) linked thereto for example is a constructs originating by experimental manipulations in which either a) said nucleic acid molecule, or b) said regulatory nucleic acid molecule or c) both (i.e. (a) and (b)) is not located in its natural (native) genetic environment or has been modified by experimental manipulations, an example of a modification being a substitution, addition, deletion, inversion or insertion of one or more nucleotide residues. Natural genetic environment refers to the natural genomic locus in the organism of origin, or to the presence in a genomic library. In the case of a genomic library, the natural genetic environment of the sequence of the nucleic acid molecule is preferably retained, at least in part. The environment flanks the nucleic acid sequence at least at one side and has a sequence of at least 50 bp, preferably at least 500 bp, especially preferably at least 1,000 bp, very especially preferably at least 5,000 bp, in length. A naturally occurring expression construct—for example the naturally occurring combination of a promoter with the corresponding gene—becomes a transgenic expression construct when it is modified by non-natural, synthetic "artificial" methods such as, for example, mutagenization. Such methods have been described (U.S. Pat. No. 5,565,350; WO 00/15815). For example a protein encoding nucleic acid molecule operably linked to a promoter, which is not the native promoter of this molecule, is considered to be heterologous with respect to the promoter. Preferably, heterologous DNA is not endogenous to or not naturally associated with the cell into which it is introduced, but has been obtained from another cell or has been synthesized. Heterologous DNA also includes an endogenous DNA sequence, which contains some modification, non-naturally occurring, multiple copies of an endogenous DNA sequence, or a DNA sequence which is not naturally associated with another DNA sequence physically linked thereto. Generally, although not necessarily, heterologous DNA encodes RNA or proteins that are not normally produced by the cell into which it is expressed.

Hybridization: The term "hybridisation" as defined herein is a process wherein substantially complementary nucleotide sequences anneal to each other. The hybridisation process can occur entirely in solution, i.e. both complementary nucleic acids are in solution. The hybridisation process can also occur with one of the complementary nucleic acids immobilised to a matrix such as magnetic beads, Sepharose beads or any other resin. The hybridisation process can furthermore occur with one of the complementary nucleic acids immobilised to a solid support such as a nitrocellulose or nylon membrane or immobilised by e.g. photolithography to, for example, a siliceous glass support (the latter known as nucleic acid arrays or microarrays or as nucleic acid chips). In order to allow hybridisation to occur, the nucleic acid molecules are generally thermally or chemically denatured to melt a double strand into two single strands and/or to remove hairpins or other secondary structures from single stranded nucleic acids.

The term "stringency" refers to the conditions under which a hybridisation takes place. The stringency of hybridisation is influenced by conditions such as temperature, salt concentration, ionic strength and hybridisation buffer composition. Generally, low stringency conditions are selected to be about 30° C. lower than the thermal melting point (Tm) for the specific sequence at a defined ionic strength and pH. Medium stringency conditions are when the temperature is 20° C. below Tm, and high stringency conditions are when the temperature is 10° C. below Tm. High stringency hybridisation conditions are typically used for isolating hybridising sequences that have high sequence similarity to the target nucleic acid sequence. However, nucleic acids may deviate in sequence and still encode a substantially identical polypeptide, due to the degeneracy of the genetic code. Therefore, medium stringency hybridisation conditions may sometimes be needed to identify such nucleic acid molecules.

The "Tm" is the temperature under defined ionic strength and pH, at which 50% of the target sequence hybridises to a perfectly matched probe. The Tm is dependent upon the solution conditions and the base composition and length of the probe. For example, longer sequences hybridise specifically at higher temperatures. The maximum rate of hybridisation is obtained from about 16° C. up to 32° C. below Tm. The presence of monovalent cations in the hybridisation solution reduce the electrostatic repulsion between the two nucleic acid strands thereby promoting hybrid formation; this effect is visible for sodium concentrations of up to 0.4M (for higher concentrations, this effect may be ignored). Formamide reduces the melting temperature of DNA-DNA and DNA-RNA duplexes with 0.6 to 0.7° C. for each percent formamide, and addition of 50% formamide allows hybridisation to be performed at 30 to 45° C., though the rate of hybridisation will be lowered. Base pair mismatches reduce the hybridisation rate and the thermal stability of the duplexes. On average and for large probes, the Tm decreases about 1° C. per % base mismatch. The Tm may be calculated using the following equations, depending on the types of hybrids:

DNA-DNA Hybrids (Meinkoth and Wahl, Anal. Biochem., 138: 267-284, 1984):

$Tm=81.5° C.+16.6×\log[Na+]a+0.41×\%[G/Cb]-500×[Lc]-1-0.61×\%$ formamide

DNA-RNA or RNA-RNA Hybrids:

$Tm=79.8+18.5(\log 10[Na+]a)+0.58(\% G/Cb)+11.8(\% G/Cb)2-820/Lc$ oligo-DNA or oligo-RNAd hybrids:
For <20 nucleotides: Tm=2 (In)
For 20-35 nucleotides: Tm=22+1.46 (In)
a or for other monovalent cation, but only accurate in the 0.01-0.4 M range.
b only accurate for % GC in the 30% to 75% range.
c L=length of duplex in base pairs.
d Oligo, oligonucleotide; In, effective length of primer=2×(no. of G/C)+(no. of NT).

Non-specific binding may be controlled using any one of a number of known techniques such as, for example, blocking the membrane with protein containing solutions, additions of heterologous RNA, DNA, and SDS to the hybridisation buffer, and treatment with Rnase. For non-related probes, a series of hybridizations may be performed by varying one of (i) progressively lowering the annealing temperature (for example from 68° C. to 42° C.) or (ii) progressively lowering the formamide concentration (for example from 50% to 0%). The skilled artisan is aware of various parameters which may be altered during hybridisation and which will either maintain or change the stringency conditions.

Besides the hybridisation conditions, specificity of hybridisation typically also depends on the function of post-hybridisation washes. To remove background resulting from non-specific hybridisation, samples are washed with dilute salt solutions. Critical factors of such washes include the ionic strength and temperature of the final wash solution: the lower the salt concentration and the higher the wash temperature, the higher the stringency of the wash. Wash conditions are typically performed at or below hybridisation stringency. A positive hybridisation gives a signal that is at least twice of that of the background. Generally, suitable stringent conditions for nucleic acid hybridisation assays or gene amplification detection procedures are as set forth above. More or less stringent conditions may also be selected. The skilled artisan is aware of various parameters which may be altered during washing and which will either maintain or change the stringency conditions.

For example, typical high stringency hybridisation conditions for DNA hybrids longer than 50 nucleotides encompass hybridisation at 65° C. in 1×SSC or at 42° C. in 1×SSC and 50% formamide, followed by washing at 65° C. in 0.3×SSC. Examples of medium stringency hybridisation conditions for DNA hybrids longer than 50 nucleotides encompass hybridisation at 50° C. in 4×SSC or at 40° C. in 6×SSC and 50% formamide, followed by washing at 50° C. in 2×SSC. The length of the hybrid is the anticipated length for the hybridising nucleic acid. When nucleic acids of known sequence are hybridised, the hybrid length may be determined by aligning the sequences and identifying the conserved regions described herein. 1×SSC is 0.15M NaCl and 15 mM sodium citrate; the hybridisation solution and wash solutions may additionally include 5×Denhardt's reagent, 0.5-1.0% SDS, 100 μg/ml denatured, fragmented salmon sperm DNA, 0.5% sodium pyrophosphate. Another example of high stringency conditions is hybridisation at 65° C. in 0.1×SSC comprising 0.1 SDS and optionally 5×Denhardt's reagent, 100 μg/ml denatured, fragmented salmon sperm DNA, 0.5% sodium pyrophosphate, followed by the washing at 65° C. in 0.3×SSC. For the purposes of defining the level of stringency, reference can be made to Sambrook et al. (2001) Molecular Cloning: a laboratory manual, 3rd Edition, Cold Spring Harbor Laboratory Press, CSH, New York or to Current Protocols in Molecular Biology, John Wiley & Sons, N.Y. (1989 and yearly updates).

"Identity": "Identity" when used in respect to the comparison of two or more nucleic acid or amino acid molecules means that the sequences of said molecules share a certain degree of sequence similarity, the sequences being partially identical.

Enzyme variants may be defined by their sequence identity when compared to a parent enzyme. Sequence identity usually is provided as "% sequence identity" or "% identity". To determine the percent-identity between two amino acid sequences in a first step a pairwise sequence alignment is generated between those two sequences, wherein the two sequences are aligned over their complete length (i.e., a pairwise global alignment). The alignment is generated with a program implementing the Needleman and Wunsch algorithm (J. Mol. Biol. (1979) 48, p. 443-453), preferably by using the program "NEEDLE" (The European Molecular Biology Open Software Suite (EMBOSS)) with the programs default parameters (gapopen=10.0, gapextend=0.5 and matrix=EBLOSUM62). The preferred alignment for the purpose of this invention is that alignment, from which the highest sequence identity can be determined.

The following example is meant to illustrate two nucleotide sequences, but the same calculations apply to protein sequences:

```
Seq A: AAGATACTG length: 9 bases

Seq B: GATCTGA length: 7 bases
```

Hence, the shorter sequence is sequence B.

Producing a pairwise global alignment which is showing both sequences over their complete lengths results in

```
Seq A: AAGATACTG-
       ||| |||
Seq B: --GAT-CTGA
```

The "|" symbol in the alignment indicates identical residues (which means bases for DNA or amino acids for proteins). The number of identical residues is 6.

The "-" symbol in the alignment indicates gaps. The number of gaps introduced by alignment within the Seq B is 1. The number of gaps introduced by alignment at borders of Seq B is 2, and at borders of Seq A is 1.

The alignment length showing the aligned sequences over their complete length is 10.

Producing a pairwise alignment which is showing the shorter sequence over its complete length according to the invention consequently results in:

```
Seq A: GATACTG-
       ||| |||
Seq B: GAT-CTGA
```

Producing a pairwise alignment which is showing sequence A over its complete length according to the invention consequently results in:

```
Seq A: AAGATACTG
       ||| |||
Seq B: --GAT-CTG
```

Producing a pairwise alignment which is showing sequence B over its complete length according to the invention consequently results in:

```
Seq A: GATACTG-
       ||| |||
Seq B: GAT-CTGA
```

The alignment length showing the shorter sequence over its complete length is 8 (one gap is present which is factored in the alignment length of the shorter sequence).

Accordingly, the alignment length showing Seq A over its complete length would be 9 (meaning Seq A is the sequence of the invention).

Accordingly, the alignment length showing Seq B over its complete length would be 8 (meaning Seq B is the sequence of the invention).

After aligning two sequences, in a second step, an identity value is determined from the alignment produced. For purposes of this description, percent identity is calculated by %-identity=(identical residues/length of the alignment region which is showing the respective sequence of this invention over its complete length)*100. Thus, sequence identity in relation to comparison of two amino acid sequences according to this embodiment is calculated by dividing the number of identical residues by the length of the alignment region which is showing the respective sequence of this invention over its complete length. This value is multiplied with 100 to give "%-identity". According to the example provided above, %-identity is: for Seq A being the sequence of the invention (6/9)*100=66.7%; for Seq B being the sequence of the invention (6/8)*100=75%.

Isolated: The term "isolated" as used herein means that a material has been removed by the hand of man and exists apart from its original, native environment and is therefore not a product of nature. An isolated material or molecule (such as a DNA molecule or enzyme) may exist in a purified form or may exist in a non-native environment such as, for example, in a transgenic host cell. For example, a naturally occurring nucleic acid molecule or polypeptide present in a living cell is not isolated, but the same nucleic acid molecule or polypeptide, separated from some or all of the coexisting materials in the natural system, is isolated. Such nucleic acid molecules can be part of a vector and/or such nucleic acid molecules or polypeptides could be part of a composition, and would be isolated in that such a vector or composition is not part of its original environment. Preferably, the term "isolated" when used in relation to a nucleic acid molecule, as in "an isolated nucleic acid sequence" refers to a nucleic acid sequence that is identified and separated from at least one contaminant nucleic acid molecule with which it is ordinarily associated in its natural source. Isolated nucleic acid molecule is nucleic acid molecule present in a form or setting that is different from that in which it is found in nature. In contrast, non-isolated nucleic acid molecules are nucleic acid molecules such as DNA and RNA, which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs, which encode a multitude of proteins. However, an isolated nucleic acid sequence comprising for example SEQ ID NO: 1 includes, by way of example, such nucleic acid sequences in cells which ordinarily contain SEQ ID NO: 1 where the nucleic acid sequence is in a genomic or plasmid location different from that of natural cells, or is otherwise flanked by a different nucleic acid sequence than that found in nature. The isolated nucleic acid sequence may be present in single- or double-stranded form. When an isolated nucleic acid sequence is to be utilized to express a protein, the nucleic acid sequence will contain at a minimum at least a portion of the sense or coding strand (i.e., the nucleic acid sequence may be single-stranded). Alternatively, it may contain both the sense and anti-sense strands (i.e., the nucleic acid sequence may be double-stranded).

Nitrilase: The term "nitrilase" as used herein refers to an enzyme catalyzing the reaction from meth-acrylonitrile to meth-ammonium acrylate and/or the reaction from acrylonitrile to ammonium acrylate. It also encompasses enzymes that are catalyzing additional reactions despite those mentioned before.

Non-coding: The term "non-coding" refers to sequences of nucleic acid molecules that do not encode part or all of an expressed protein. Non-coding sequences include but are not limited enhancers, promoter regions, 3' untranslated regions, and 5' untranslated regions.

Nucleic acids and nucleotides: The terms "nucleic acids" and "Nucleotides" refer to naturally occurring or synthetic or artificial nucleic acid or nucleotides. The terms "nucleic acids" and "nucleotides" comprise deoxyribonucleotides or ribonucleotides or any nucleotide analogue and polymers or hybrids thereof in either single- or double-stranded, sense or antisense form. Unless otherwise indicated, a particular nucleic acid sequence also implicitly encompasses conservatively modified variants thereof (e.g., degenerate codon substitutions) and complementary sequences, as well as the sequence explicitly indicated. The term "nucleic acid" is used interchangeably herein with "gene", "cDNA, "mRNA", "oligonucleotide," and "nucleic acid molecule". Nucleotide analogues include nucleotides having modifications in the chemical structure of the base, sugar and/or phosphate, including, but not limited to, 5-position pyrimidine modifications, 8-position purine modifications, modifications at cytosine exocyclic amines, substitution of 5-bromo-uracil, and the like; and 2'-position sugar modifications, including but not limited to, sugar-modified ribonucleotides in which the 2'-OH is replaced by a group selected from H, OR, R, halo, SH, SR, NH2, NHR, NR2, or CN. Short hairpin RNAs (shRNAs) also can comprise non-natural elements such as non-natural bases, e.g., ionosin and xanthine, non-natural sugars, e.g., 2'-methoxy ribose, or non-natural phosphodiester linkages, e.g., methylphosphonates, phosphorothioates and peptides.

Nucleic acid sequence: The phrase "nucleic acid sequence" refers to a single- or double-stranded polymer of deoxyribonucleotide or ribonucleotide bases read from the 5'- to the 3'-end. It includes chromosomal DNA, self-replicating plasmids, infectious polymers of DNA or RNA and DNA or RNA that performs a primarily structural role. "Nucleic acid sequence" also refers to a consecutive list of abbreviations, letters, characters or words, which represent nucleotides. In one embodiment, a nucleic acid can be a "probe" which is a relatively short nucleic acid, usually less than 100 nucleotides in length. Often a nucleic acid probe is from about 50 nucleotides in length to about 10 nucleotides in length. A "target region" of a nucleic acid is a portion of a nucleic acid that is identified to be of interest. A "coding region" of a nucleic acid is the portion of the nucleic acid, which is transcribed and translated in a sequence-specific manner to produce into a particular polypeptide or protein when placed under the control of appropriate regulatory sequences. The coding region is said to encode such a polypeptide or protein.

Oligonucleotide: The term "oligonucleotide" refers to an oligomer or polymer of ribonucleic acid (RNA) or deoxyribonucleic acid (DNA) or mimetics thereof, as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. An oligonucleotide preferably includes two or more nucleomonomers covalently coupled to each other by linkages (e.g., phosphodiesters) or substitute linkages.

Overhang: An "overhang" is a relatively short single-stranded nucleotide sequence on the 5'- or 3'-hydroxyl end of a double-stranded oligonucleotide molecule (also referred to as an "extension," "protruding end," or "sticky end").

Polypeptide: The terms "polypeptide", "peptide", "oligopeptide", "polypeptide", "gene product", "expression product" and "protein" are used interchangeably herein to refer to a polymer or oligomer of consecutive amino acid residues.

Promoter: The terms "promoter", or "promoter sequence" are equivalents and as used herein, refer to a DNA sequence which when operably linked to a nucleotide sequence of interest is capable of controlling the transcription of the nucleotide sequence of interest into RNA. A promoter is located 5' (i.e., upstream), proximal to the transcriptional start site of a nucleotide sequence of interest whose transcription into mRNA it controls, and provides a site for specific binding by RNA polymerase and other transcription factors for initiation of transcription. The promoter does not comprise coding regions or 5' untranslated regions. The promoter may for example be heterologous or homologous to the respective cell. A nucleic acid molecule sequence is "heterologous to" an organism or a second nucleic acid molecule sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety). Suitable promoters can be derived from genes of the host cells where expression should occur or from pathogens for this host.

Purified: As used herein, the term "purified" refers to molecules, either nucleic or amino acid sequences that are removed from their natural environment, isolated or separated. "Substantially purified" molecules are at least 60% free, preferably at least 75% free, and more preferably at least 90% free from other components with which they are naturally associated. A purified nucleic acid sequence may be an isolated nucleic acid sequence.

Significant increase: An increase for example in enzymatic activity, gene expression, productivity or yield of a certain product, that is larger than the margin of error inherent in the measurement technique, preferably an increase by about 10% or 25% preferably by 50% or 75%, more preferably 2-fold or -5 fold or greater of the activity, expression, productivity or yield of the control enzyme or expression in the control cell, productivity or yield of the control cell, even more preferably an increase by about 10-fold or greater.

Significant decrease: A decrease for example in enzymatic activity, gene expression, productivity or yield of a certain product, that is larger than the margin of error inherent in the measurement technique, preferably a decrease by at least about 5% or 10%, preferably by at least about 20% or 25%, more preferably by at least about 50% or 75%, even more preferably by at least about 80% or 85%, most preferably by at least about 90%, 95%, 97%, 98% or 99%.

Substantially complementary: In its broadest sense, the term "substantially complementary", when used herein with respect to a nucleotide sequence in relation to a reference or target nucleotide sequence, means a nucleotide sequence having a percentage of identity between the substantially complementary nucleotide sequence and the exact complementary sequence of said reference or target nucleotide sequence of at least 60%, more desirably at least 70%, more desirably at least 80% or 85%, preferably at least 90%, more preferably at least 93%, still more preferably at least 95% or 96%, yet still more preferably at least 97% or 98%, yet still more preferably at least 99% or most preferably 100% (the later being equivalent to the term "identical" in this context). Preferably identity is assessed over a length of at least 19 nucleotides, preferably at least 50 nucleotides, more preferably the entire length of the nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J Mol. Biol. 48: 443-453; as defined above). A nucleotide sequence "substantially complementary" to a reference nucleotide sequence hybridizes to the reference nucleotide sequence under low stringency conditions, preferably medium stringency conditions, most preferably high stringency conditions (as defined above).

Transgene: The term "transgene" as used herein refers to any nucleic acid sequence, which is introduced into the genome of a cell by experimental manipulations. A transgene may be an "endogenous DNA sequence," or a "heterologous DNA sequence" (i.e., "foreign DNA"). The term "endogenous DNA sequence" refers to a nucleotide sequence, which is naturally found in the cell into which it is introduced so long as it does not contain some modification (e.g., a point mutation, the presence of a selectable marker gene, etc.) relative to the naturally-occurring sequence.

Transgenic: The term transgenic when referring to an organism means transformed, preferably stably transformed, with at least one recombinant nucleic acid molecule.

Vector: As used herein, the term "vector" refers to a nucleic acid molecule capable of transporting another nucleic acid molecule to which it has been linked. One type of vector is a genomic integrated vector, or "integrated vector", which can become integrated into the genomic DNA of the host cell. Another type of vector is an episomal vector, i.e., a plasmid or a nucleic acid molecule capable of extra-chromosomal replication. Vectors capable of directing the expression of genes to which they are operatively linked are referred to herein as "expression vectors". In the present specification, "plasmid" and "vector" are used interchangeably unless otherwise clear from the context.

Wild type: The term "wild type", "natural" or "natural origin" means with respect to an organism that said organism is not changed, mutated, or otherwise manipulated by man. With respect to a polypeptide or nucleic acid sequence, that the polypeptide or nucleic acid sequence is naturally occurring or available in at least one naturally occurring organism which is not changed, mutated, or otherwise manipulated by man.

A wild type of a microorganism refers to a microorganism whose genome is present in a state as before the introduction of a genetic modification of a certain gene. The genetic modification may be e.g. a deletion of a gene or a part thereof or a point mutation or the introduction of a gene.

The terms "production" or "productivity" are art-recognized and include the concentration of the fermentation product (for example, dsRNA) formed within a given time and a given fermentation volume (e.g., kg product per hour per liter). The term "efficiency of production" includes the time required for a particular level of production to be achieved (for example, how long it takes for the cell to attain a particular rate of output of a fine chemical).

The term "yield" or "product/carbon yield" is art-recognized and includes the efficiency of the conversion of the carbon source into the product (i.e., fine chemical). This is generally written as, for example, kg product per kg carbon source. By increasing the yield or production of the compound, the quantity of recovered molecules or of useful recovered molecules of that compound in a given amount of culture over a given amount of time is increased.

The term "recombinant microorganism" includes microorganisms which have been genetically modified such that they exhibit an altered or different genotype and/or phenotype (e. g., when the genetic modification affects coding nucleic acid sequences of the microorganism) as compared to the wild type microorganism from which it was derived. A recombinant microorganism comprises at least one recombinant nucleic acid molecule.

The term "recombinant" with respect to nucleic acid molecules refers to nucleic acid molecules produced by man using recombinant nucleic acid techniques. The term comprises nucleic acid molecules which as such do not exist in nature or do not exist in the organism from which the nucleic acid molecule is derived, but are modified, changed, mutated or otherwise manipulated by man. Preferably, a "recombinant nucleic acid molecule" is a non-naturally occurring nucleic acid molecule that differs in sequence from a naturally occurring nucleic acid molecule by at least one nucleic acid. A "recombinant nucleic acid molecules" may also comprise a "recombinant construct" which comprises, preferably operably linked, a sequence of nucleic acid molecules not naturally occurring in that order. Preferred methods for producing said recombinant nucleic acid molecules may comprise cloning techniques, directed or non-directed mutagenesis, gene synthesis or recombination techniques.

An example of such a recombinant nucleic acid molecule is a plasmid into which a heterologous DNA-sequence has been inserted or a gene or promoter which has been mutated compared to the gene or promoter from which the recombinant nucleic acid molecule derived. The mutation may be introduced by means of directed mutagenesis technologies known in the art or by random mutagenesis technologies such as chemical, UV light or x-ray mutagenesis or directed evolution technologies.

The term "directed evolution" is used synonymously with the term "metabolic evolution" herein and involves applying a selection pressure that favors the growth of mutants with the traits of interest. The selection pressure can be based on different culture conditions, ATP and growth coupled selection and redox related selection. The selection pressure can be carried out with batch fermentation with serial transferring inoculation or continuous culture with the same pressure.

The term "expression" or "gene expression" means the transcription of a specific gene(s) or specific genetic vector construct. The term "expression" or "gene expression" in particular means the transcription of gene(s) or genetic vector construct into mRNA. The process includes transcription of DNA and may include processing of the resulting RNA-product. The term "expression" or "gene expression" may also include the translation of the mRNA and therewith the synthesis of the encoded protein, i.e. protein expression.

EXAMPLES

Chemicals and Common Methods

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in M. Green & J. Sambrook (2012) Molecular Cloning: a laboratory manual, 4th Edition Cold Spring Harbor Laboratory Press, CSH, New York; Ausubel et al., Current Protocols in Molecular Biology, Wiley Online Library; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth Enzymol. 68; Wu et al., (Eds.) 1983 Meth. Enzymol. 100 and 101; Grossman and Moldave (Eds.) 1980 Meth. Enzymol. 65; Miller (Ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York.

If not stated otherwise herein, abbreviations and nomenclature, where employed, are deemed standard in the field and commonly used in professional journals such as those cited herein.

Example 1

100 potential nitrilases were screened for activity of conversion acetonitrile to acrylic acid. Donor organism and SEQ ID of the amino acid sequence of 37 of these nitrilases are listed in Table 1. The coding region of the nitrilases were optimized for expression in *E. coli*, these sequences synthesized and cloned in the expression vector pDHE (SEQ ID 75) (Stueckler et al. (2010) Tetrahedron 66(3-2).

The expression vectors were transformed into *E. coli*, expression of the nitrilases induced and the culture harvested and tested for activity as described in WO200132890 and Example 2.

TABLE 1

Donor Organism and SEQ ID of 32 tested nitrilases

| Seq. ID | Donor |
|---|---|
| 2 | Unknown prokaryotic organism |
| 4 | Unknown prokaryotic organism |
| 6 | *Flavihumibacter solisilvae* |
| 8 | *Acidovorax facilis* 72W |
| 10 | *Pseudomonas* sp. RIT357 |
| 12 | *Nocardia brasiliensis* NBRC 14402 |
| 14 | *Pseudomonas fluorescens* |
| 16 | *Agrobacterium rubi* |
| 18 | Unknown prokaryotic organism |
| 20 | *Candidatus Dadabacteria* |
| 22 | Unknown prokaryotic organism |
| 26 | *Tepidicaulis marinus* |
| 28 | Unknown prokaryotic organism |
| 30 | Unknown prokaryotic organism |
| 32 | Unknown prokaryotic organism |
| 34 | *Synechococcus* sp. 009605 |
| 38 | *Aquimarina atlantica* |
| 40 | *Arthrobacter* sp. Soil736 |
| 42 | *Cupriavidus basilensis* |
| 46 | *Sphingomonas wittichii* RW1 |
| 48 | *Pseudomonas mandelii* JR-1 |
| 52 | *Arabidopsis thaliana* |
| 54 | *Brassica oleracea* |
| 56 | *Salinisphaera shabanensis* E1L3A |
| 60 | *Smithella* sp. SDB |
| 62 | *Bradyrhizobium diazoefficiens* |
| 64 | *Actinobacteria bacterium* RBG_13_55_18 |
| 66 | *Rhizobium* sp. YK2 |
| 68 | bacterium YEK0313 |
| 70 | *Paenibacillus darwinianus* |
| 72 | *Haloarcula* sp. CBA1115 |
| 74 | *Hungatella hathewayi* |

Example 2

In a 1.5 mL Eppendorf tube, 20 μL of acrylonitrile were added to a 50 mM phosphate buffer solution at pH 7. To start the screening, 100 μL of *E. coli* cell suspension containing different nitrilases were added and the mixture shaken at 25° C. After 24 hours the reaction mixture was centrifuged and the supernatant injected in a H PLC. The conversion was calculated as reacted acrylonitrile.

TABLE 2

Acrylonitrile conversion of 32 tested nitrilases

| Seq. ID | Substrate | Acrylic acid |
|---|---|---|
| 2 | Acrylonitrile | >99.9% |
| 4 | Acrylonitrile | >99.9% |
| 6 | Acrylonitrile | >99.9% |
| 8 | Acrylonitrile | >99.9% |
| 10 | Acrylonitrile | >99.9% |
| 12 | Acrylonitrile | 95% |
| 14 | Acrylonitrile | >99.9% |
| 16 | Acrylonitrile | 77% |
| 18 | Acrylonitrile | >99.9% |
| 20 | Acrylonitrile | >99.9% |
| 22 | Acrylonitrile | 32% |
| 26 | Acrylonitrile | >99.9% |
| 28 | Acrylonitrile | 90% |
| 30 | Acrylonitrile | 95% |
| 32 | Acrylonitrile | 97% |
| 34 | Acrylonitrile | 96% |
| 38 | Acrylonitrile | >99.9% |
| 40 | Acrylonitrile | >99.9% |
| 46 | Acrylonitrile | 90% |
| 48 | Acrylonitrile | >99.9% |
| 52 | Acrylonitrile | >99.9% |
| 54 | Acrylonitrile | >99.9% |
| 56 | Acrylonitrile | 40% |
| 60 | Acrylonitrile | 65% |
| 62 | Acrylonitrile | 10% |
| 64 | Acrylonitrile | 13% |
| 66 | Acrylonitrile | 72% |
| 68 | Acrylonitrile | >99.9% |
| 42 | Acrylonitrile | >99.9% |
| 44 | Acrylonitrile | >99.9% |
| 70 | Acrylonitrile | 0% |
| 72 | Acrylonitrile | 0% |
| 74 | Acrylonitrile | 0% |

Example 3

Water and 28 g of Acetonitrile (ACN) were placed in a reactor. The amount of water was adjusted so that the total amount of water+biocatalyst was 2798 g.

The biocatalyst was used in the form of a concentrate cell suspension containing BD5220 (Seq. ID N. 2) and it was added to the reactor, whereby the reaction started. During the reaction, 1202 g of additional acrylonitrile was added. The temperature was kept at 26° C. and the ACN concentration was measured by on-line FTIR, and the rate of addition of ACN was adjusted so that the ACN concentration in the reaction mixture was kept constant at 1±0.2% (w/w) until the entire ACN has been added to the reaction. The reaction was stopped after ACN concentration had decreased to <100 ppm. At the end of the reaction, the final concentration of ammonium acrylate was 51.2 wt % (acrylic acid 41.5 wt %).

Example 4

Water and 28 g of ACN were placed in a reactor. The amount of water was adjusted so that the total amount of water+biocatalyst was 3107 g.

The biocatalyst was used in the form of a concentrate cell suspension containing a nitrilase from *Flavihumibacter solisilvae* (Seq. ID N. 6) and it was added to the reactor, whereby the reaction started. During the reaction, 1005 g of additional acrylonitrile was added. The temperature was kept at 30° C. and the ACN concentration was measured by on-line FTIR, and the rate of addition of ACN was adjusted so that the ACN concentration in the reaction mixture was kept constant at 1±0.2% (w/w) until the entire ACN has been added to the reaction. The reaction was stopped after ACN concentration had decreased to <100 ppm. At the end of the reaction, the final concentration of ammonium acrylate was 41.9 wt % (acrylic acid 33.9 wt %).

What is claimed is:

1. A process for producing (meth-) ammonium acrylate comprising the steps of
   a. Providing an aqueous medium comprising water, nitrilase and (meth-) acrylonitrile,
   b. Incubating the aqueous medium and
   c. Optionally isolating the (meth-) ammonium acrylate from the reaction mixture, wherein the nitrilase has at least 80% sequence identity to SEQ ID NO:2 and the amino acid differences between said nitrilase and the nitrilase of SEQ ID NO:2 are conservative amino acid substitutions;
   wherein the polypeptide has an activity of converting (meth-) acrylonitrile to (meth-) ammonium acrylate.

2. The process of claim 1 wherein the (meth-) acrylonitrile is continuously added to the aqueous medium until 10 min before end of the incubation time thereby keeping the (meth-) acrylonitrile concentration at about 1-2% w/w.

3. The process of claim 1 wherein the aqueous medium is incubated for at least 2 h up to 48 h.

4. The process of claim 1 wherein the aqueous medium is incubated between 15 and 50° C.

5. The process of claim 1 wherein the nitrilase is produced by fermentation.

6. The process of claim 3, wherein the nitrilase has the amino acid sequence of SEQ ID NO:2.

* * * * *